(12) United States Patent
Amedi et al.

(10) Patent No.: US 12,579,904 B2
(45) Date of Patent: Mar. 17, 2026

(54) DIGITAL MAZES IN THERAPEUTICS

(71) Applicant: REMEPY HEALTH LTD, Ramat Hasharon (IL)

(72) Inventors: Amir Amedi, Modiin-Macabim Reut (IL); Michal Tsur-Shalev, Zichron Yaacov (IL); Or Shoval, Ramat Hasharon (IL); Shahar Shelly, Herzlyia (IL); Nira Neomi Saporta, Givatayim (IL)

(73) Assignee: REMEPY HEALTH LTD, Ramat Hasharon (IL)

( * ) Notice: Subject to any disclaimer, the term of this patent is extended or adjusted under 35 U.S.C. 154(b) by 17 days.

(21) Appl. No.: 18/646,018

(22) Filed: Apr. 25, 2024

(65) Prior Publication Data

US 2024/0363228 A1     Oct. 31, 2024

Related U.S. Application Data

(60) Provisional application No. 63/567,005, filed on Mar. 19, 2024, provisional application No. 63/557,478, (Continued)

(51) Int. Cl.
| | |
|---|---|
| *G16H 20/70* | (2018.01) |
| *A61B 5/00* | (2006.01) |
(Continued)

(52) U.S. Cl.
CPC ............ *G09B 19/00* (2013.01); *A61B 5/4088* (2013.01); *A61B 5/4848* (2013.01); *A61B 5/7475* (2013.01); *A61M 21/00* (2013.01); *A63F 9/0612* (2013.01); *G16B 40/00*

(2019.02); *G16H 10/20* (2018.01); *G16H 10/60* (2018.01); *G16H 20/10* (2018.01); *G16H 20/17* (2018.01);
(Continued)

(58) Field of Classification Search
None
See application file for complete search history.

(56) References Cited

U.S. PATENT DOCUMENTS

| | | | |
|---|---|---|---|
| 6,632,174 B1 | 10/2003 | Breznitz | |
| 10,943,407 B1 * | 3/2021 | Morgan | ................. G16H 15/00 |
(Continued)

FOREIGN PATENT DOCUMENTS

| | | | |
|---|---|---|---|
| WO | WO2008/052166 | 5/2008 | |
| WO | WO-2008052166 A2 * | 5/2008 | .............. G06F 3/011 |

OTHER PUBLICATIONS

Levy-Tzedek et al., Aging and Sensory Substitution in a Virtual Navigation Task, PLOS ONE 11(3): e0151593 (2016), doi:10.1371/journal.pone.0151593 (Year: 2016).*
(Continued)

*Primary Examiner* — Jason B Dunham
*Assistant Examiner* — Nicholas Akogyeram, II
(74) *Attorney, Agent, or Firm* — Mark S. Cohen; PEARL COHEN ZEDEK LATZER BARATZ LLP

(57) ABSTRACT

The presently disclosed subject matter relates to computer-based methods in the field of digital therapeutics by means of a digital maze. The digital mazes utilize: sensory inhibition, sensory substitution, sensory integration, or a combination thereof. Various digital interventions, their related methods in digital therapeutics and systems are disclosed herein.

16 Claims, 39 Drawing Sheets

Related U.S. Application Data filed on Feb. 24, 2024, provisional application No. 63/591,360, filed on Oct. 18, 2023, provisional application No. 63/498,587, filed on Apr. 27, 2023.

(51) Int. Cl.

| | |
|---|---|
| *A61M 21/00* | (2006.01) |
| *A63F 9/06* | (2006.01) |
| *G09B 19/00* | (2006.01) |
| *G16B 40/00* | (2019.01) |
| *G16H 10/20* | (2018.01) |
| *G16H 10/60* | (2018.01) |
| *G16H 20/10* | (2018.01) |
| *G16H 20/17* | (2018.01) |
| *G16H 20/30* | (2018.01) |
| *G16H 50/30* | (2018.01) |

(52) U.S. Cl.
CPC ............. *G16H 20/30* (2018.01); *G16H 20/70* (2018.01); *G16H 50/30* (2018.01); *A61M 2021/0022* (2013.01); *A61M 2021/0027* (2013.01); *A61M 2021/005* (2013.01); *A63F 2300/10* (2013.01); *A63F 2300/30* (2013.01); *A63F 2300/8094* (2013.01)

(56) References Cited

U.S. PATENT DOCUMENTS

| | | | |
|---|---|---|---|
| 2006/0161218 A1 | 7/2006 | Danilov | |
| 2007/0018989 A1 | 1/2007 | Roberts | |
| 2008/0026359 A1* | 1/2008 | O'Malley | G09B 7/06 |
| | | | 434/323 |
| 2014/0079251 A1 | 3/2014 | O'Grady | |
| 2015/0290454 A1* | 10/2015 | Tyler | G06F 3/012 |
| | | | 607/134 |
| 2016/0008364 A1 | 1/2016 | Alam | |
| 2017/0113046 A1 | 4/2017 | Fried et al. | |
| 2018/0126117 A1 | 5/2018 | Bar Haim et al. | |
| 2018/0292888 A1 | 10/2018 | Slepian | |
| 2019/0333496 A1 | 10/2019 | Amedi et al. | |
| 2020/0402643 A1 | 12/2020 | Trees et al. | |
| 2022/0005366 A1* | 1/2022 | Nedivi | H04L 67/535 |
| 2022/0139250 A1 | 5/2022 | Yanchurevich | |
| 2024/0069363 A1 | 2/2024 | Caspari | |
| 2024/0363019 A1 | 10/2024 | Amedi | |

OTHER PUBLICATIONS

Abboud S, Hanassy S, Levy-Tzedek S, Maidenbaum S, Amedi A. EyeMusic: Introducing a "visual" colorful experience for the blind using auditory sensory substitution. Restor Neurol Neurosci. 2014;32(2):247-257.

Aggius-Vella E, Chebat DR, Maidenbaum S, Amedi A. Activation of human visual area V6 during egocentric navigation with and without visual experience. Curr Biol. 2023;33(7):1211-1219.e5.

Agrawal T, Schachner A. Hearing water temperature: Characterizing the development of nuanced perception of sound sources. Dev Sci. May 2023;26(3):e13321.

Amedi A, Floel A, Knecht S, Zohary E, Cohen LG. Transcranial magnetic stimulation of the occipital pole interferes with verbal processing in blind subjects. Nat Neurosci. Nov. 2004;7(11):1266-1270.

Amedi A, Raz N, Pianka P, Malach R, Zohary E. Early 'visual' cortex activation correlates with superior verbal memory performance in the blind. Nat Neurosci. Jul. 2003;6(7):758-766.

Amedi A. Remepy: The Software-Drug Combination Platform for Pharma Companies. Presentation for eHealth Ventures at MIXiii conference. Nov. 10, 2022.

Bach-y-Rita P, Kercel SW. Sensory substitution and the human-machine interface. Trends Cogn Sci. 2003;7(12):541-546.

Ballesio A, Zagaria A, Vacca M, Pariante CM, Lombardo C. Comparative efficacy of psychological interventions on immune biomarkers: A systematic review and network meta-analysis (NMA). Brain Behav Immun. Jul. 2023;111:424-435.

Balthazar J, Schöwe NM, Cipolli GC, Buck HS, Viel TA. Enriched Environment Significantly Reduced Senile Plaques in a Transgenic Mice Model of Alzheimer's Disease, Improving Memory. Front Aging Neurosci. Sep. 2018;10:288.

Buchs G, Maidenbaum S, Amedi A. Obstacle Identification and Avoidance Using the 'EyeCane': a Tactile Sensory Substitution Device for Blind Individuals. In: Auvray M, Duriez C, eds. EuroHaptics 2014, Part II. LNCS 8619. 2014:96-103.

Chebat DR, Harrar V, Kupers R, Maidenbaum S, Amedi A, Ptito M. Sensory substitution and the neural correlates of navigation in blindness. In: Mobility of Visually Impaired People: Fundamentals and ICT Assistive Technologies. 2018:167-200.

Chebat DR, Maidenbaum S, Amedi A. Navigation using sensory substitution in real and virtual mazes. PLoS One. 2015;10(6):e012630.

Chebat DR, Schneider FC, Kupers R, Ptito M. Navigation with a sensory substitution device in congenitally blind individuals. Neuroreport. 2011;22(7):342-347.

Chebat DR, Schneider FC, Ptito M. Spatial competence and brain plasticity in congenital blindness via sensory substitution devices. Front Neurosci. 2020;14:815.

Cieśla K, Wolak T, Lorens A, Heimler B, Skarżyński H, Amedi A. Immediate improvement of speech-in-noise perception through multisensory stimulation via an auditory to tactile sensory substitution. Restor Neurol Neurosci. 2019;37(2):155-166.

Cieśla K, Wolak T, Lorens A, Mentzel M, Skarżyński H, Amedi A. Effects of training and using an audio-tactile sensory substitution device on speech-in-noise understanding. Sci Rep. 2022;12(1):3206.

Clemenson GD, Stark CEL. Virtual environmental enrichment through video games improves hippocampal-associated memory. J Neurosci. 2015;35(49): 16116-16125.

Clemenson GD, Stark SM, Rutledge SM, Stark CEL. Enriching hippocampal memory function in older adults through video games. Behav Brain Res. 2020;390: 112667.

Creswell JD, Taren AA, Lindsay EK, Greco CM, Gianaros PJ, Fairgrieve A, Marsland AL, Brown KW, Way BM, Rosen RK, Ferris JL. Alterations in resting state functional connectivity link mindfulness meditation with reduced interleukin-6: a randomized controlled trial. Biol Psychiatry. 2016;80(1):53-61.

Deroy O, Auvray M. A crossmodal perspective on sensory substitution. In: Stokes D, Matthen M, Biggs S, eds. Perception and its modalities. Oxford University Press; 2014:327-349.

Hadamitzky M, Schedlowski M. Harnessing associative learning paradigms to optimize drug treatment. Trends Pharmacol Sci. 2022;43(6):464-472.

Heimler B, Amedi A. Are critical periods reversible in the adult brain? Insights on cortical specializations based on sensory deprivation studies. Neurosci Biobehav Rev. 2020;116:494-507.

Herring A, Ambrée O, Tomm M, Habermann H, Sachser N, Paulus W, Keyvani K. Environmental enrichment enhances cellular plasticity in transgenic mice with Alzheimer-like pathology. Exp Neurol. 2009;216(1):184-192.

Kobayashi S, Ohashi Y, Ando S. Effects of enriched environments with different durations and starting times on learning capacity during aging in rats assessed by a refined procedure of the Hebb-Williams maze task. J Neurosci Res. 2002;70(3):340-346.

Maidenbaum S, Chebat DR, Amedi A. Human navigation without and with vision—the role of visual experience and visual regions. BioRxiv. 2018:480558.

Maidenbaum S, Hanassy S, Abboud S, Buchs G, Chebat DR, Levy-Tzedek S, Amedi A. The "EyeCane", a new electronic travel aid for the blind: Technology, behavior & swift learning. Restor Neurol Neurosci. 2014;32(6):813-824.

Maidenbaum S, Levy-Tzedek S, Chebat DR, Amedi A, Patterson RL. Increasing accessibility to the blind of virtual environments, using a virtual mobility aid based on the "EyeCane": feasibility study. PLoS One. 2013;8(8):e72555.

Maimon A, Wald IY, Ben Oz M, Codron S, Netzer O, Heimler B, Amedi A. The Topo-Speech sensory substitution system as a method

(56)          References Cited

OTHER PUBLICATIONS of conveying spatial information to the blind and vision impaired. Switzerland: Frontiers Research Foundation; Front Hum Neurosci. 2023;16:1058093.

Netzer O, Heimler B, Shur A, Behor T, Amedi A. Backward spatial perception can be augmented through a novel visual-to-auditory sensory substitution algorithm. Sci Rep. 2021;11(1):11944.

Pascual-Leone A, Amedi A, Fregni F, Merabet LB. The plastic human brain cortex. Annu Rev Neurosci. Jan. 2005;28(1):377-401.

Sampedro-Piquero P, Begega A. Environmental enrichment as a positive behavioral intervention across the lifespan. Curr Neuropharmacol. 2017;15(4):459-470.

Schwartz M, Cahalon L. The vicious cycle governing the brain-immune system relationship in neurodegenerative diseases. Curr Opin Immunol. 2022;76:102182.

Schwartz M, Peralta Ramos JM, Ben-Yehuda H. A 20-year journey from axonal injury to neurodegenerative diseases and the prospect of immunotherapy for combating Alzheimer's disease. J Immunol. 2020;204(2):243-250.

Shields GS, Spahr CM, Slavich GM. Psychosocial interventions and immune system function: A systematic review and meta-analysis of randomized clinical trials. JAMA Psychiatry. 2020;77(10):1031-1043.

Striem-Amit E, Amedi A. Visual cortex extrastriate body-selective area activation in congenitally blind people "seeing" by using sounds. Curr Biol. 2014;24(6):687-692.

Striem-Amit E, Cohen L, Dehaene S, Amedi A. Reading with sounds: sensory substitution selectively activates the visual word form area in the blind. Neuron. 2012;76(3):640-652.

Tekampe J, van Middendorp H, Meeuwis SH, van Leusden JWR, Pacheco-López G, Hermus ARM, Evers AWM. Conditioning immune and endocrine parameters in humans: a systematic review. Psychother Psychosom. 2017;86(2):99-107.

International Search Report from PCT/IL2024/050406 dated Aug. 27, 2024.

* cited by examiner

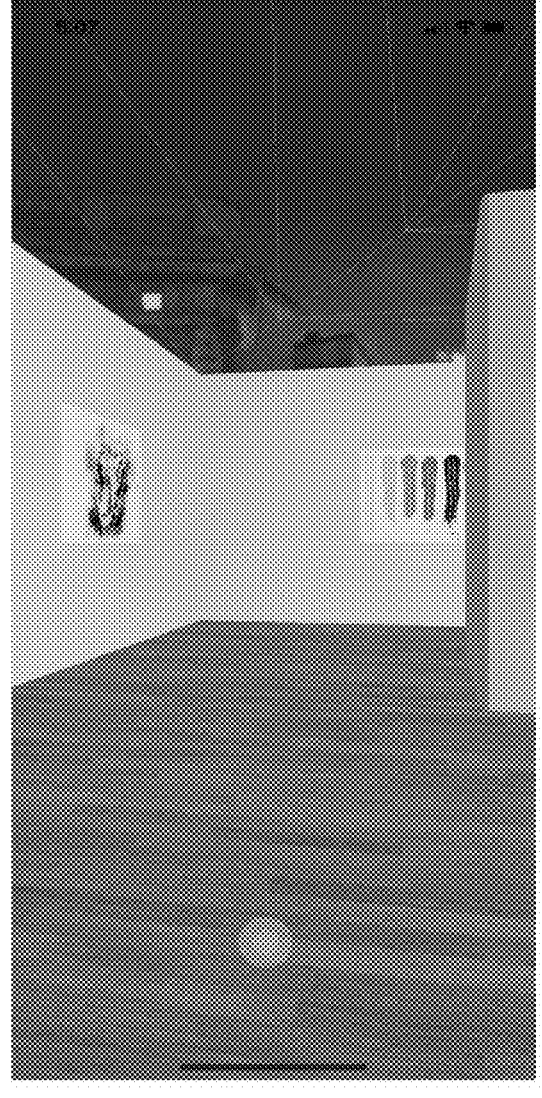
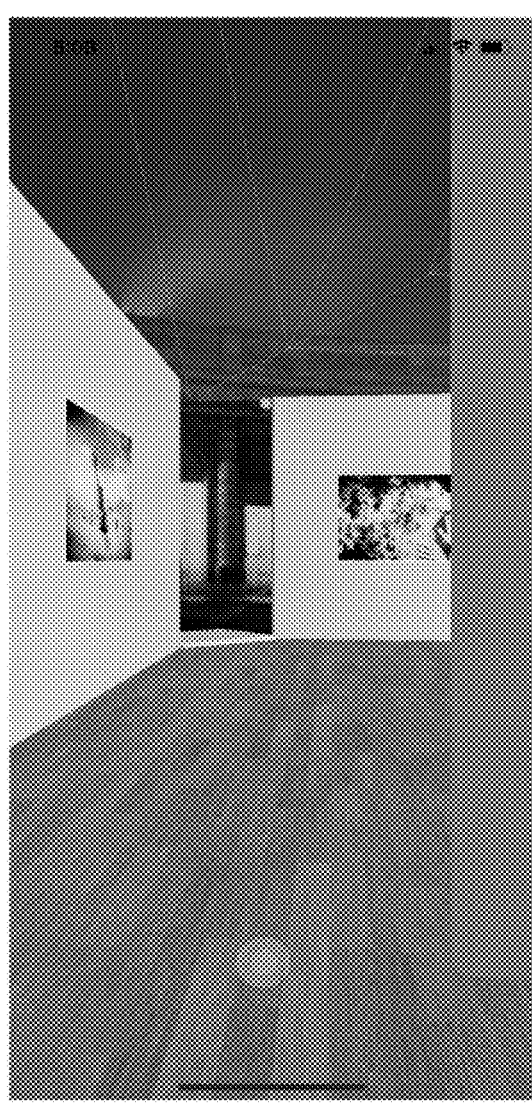
Figure 1A          Figure 1B

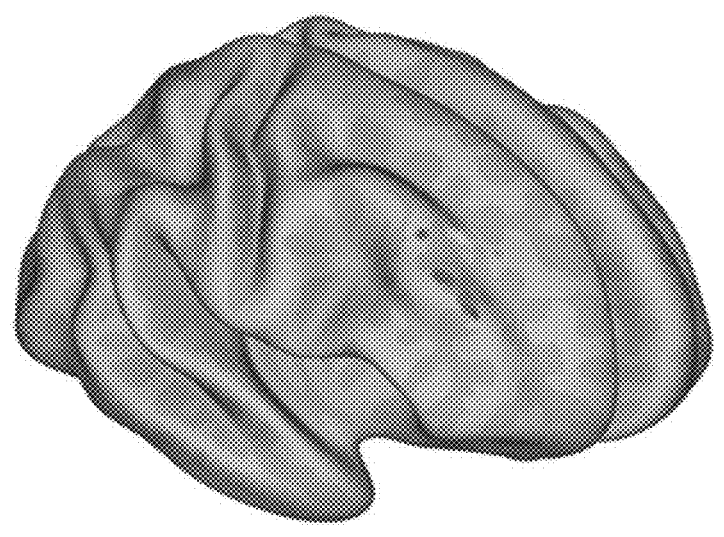
Figure 9C
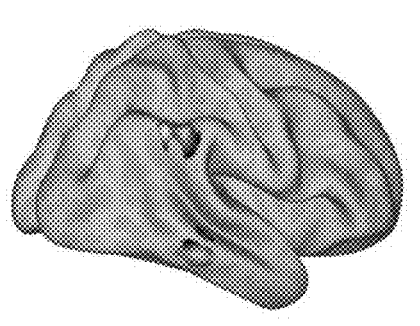  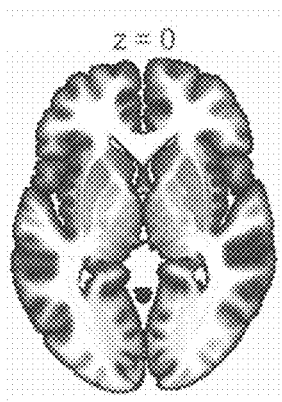
Figure 9D            Figure 9E            Figure 9F $F(1,100) = 5.41, p = .022, \eta_p^2 = .051$ $t(32) = 2.30, p = .028$          $t(68) = 6.91, p < .001$ $F(1,100) = 5.03, p = .027, \eta_p^2 = .048$ $t(32) = .80, p = .428$          $t(68) = 5.34, p < .001$ $F(1,100) = 5.21, p = .025, \eta_p^2 = .049$ $t(32) = .23, p = .821$          $t(68) = 4.34, p < .001$ $F(1,100) = 4.19, p = .043, \eta_p^2 = .040$ $t(32) = .34, p = .733$          $t(68) = 4.28, p < .001$ $F(1,100) = 2.88, p = .093, \eta_p^2 = .028$ $t(32) = 3.21, p = .003$          $t(68) = 7.66, p < .001$ $F(1,100) = 3.54, p = .063, \eta_p^2 = .034$ $t(32) = 1.01, p = .322$          $t(68) = 4.38, p < .001$ $$F(1,82) = 3.67, p = .058, \eta_p^2 = .043$$

$r_T = -0.53$
$p_T < 0.004$ $r_C = -0.38$
$p_C$ N.S

Fitted curve
95% Prediction bounds
● TEST group
● CONTROL group

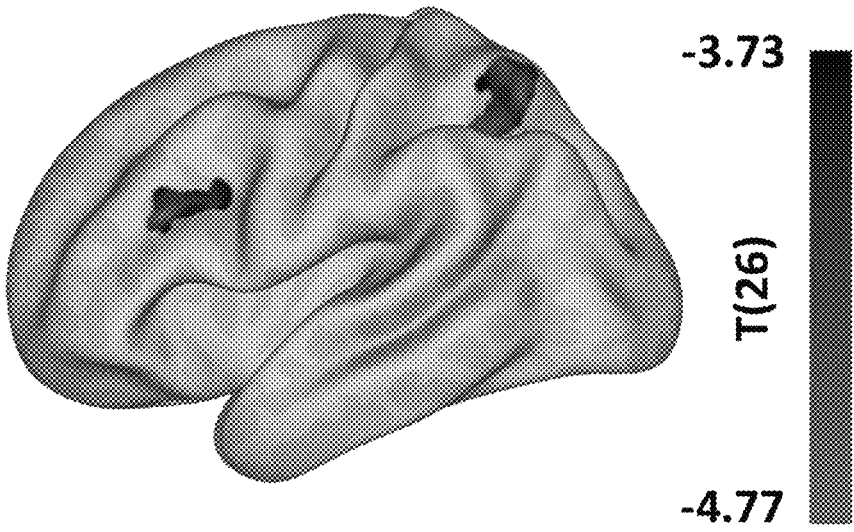
Figure 14A
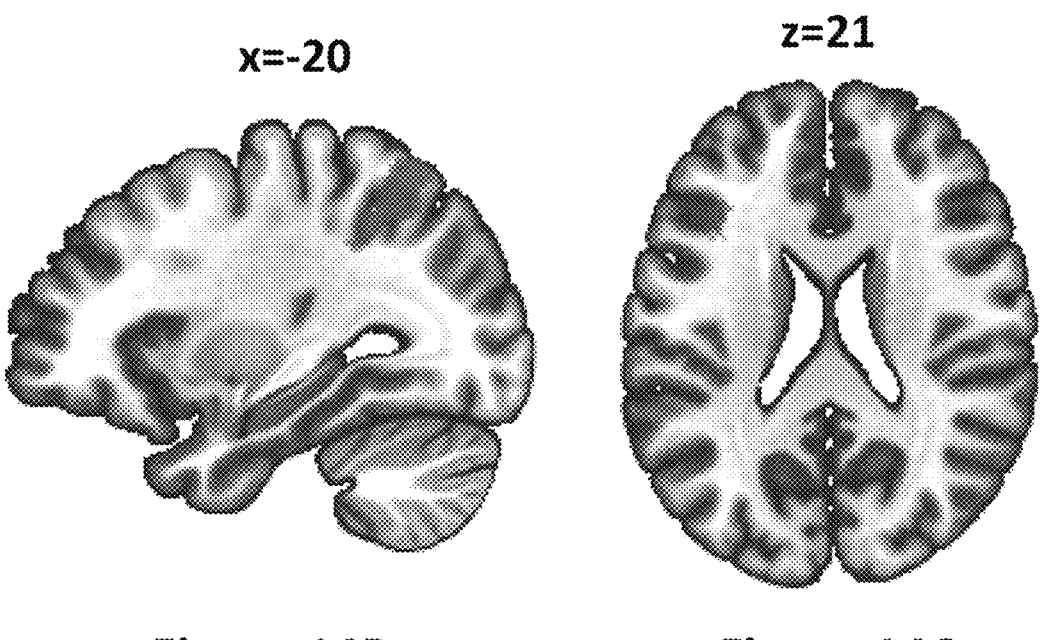
Figure 14B          Figure 14C

● Patient state of mind    ● Remsapy – Digital Intervention 3-7 days prior to treatment initiation

Figure 16A:
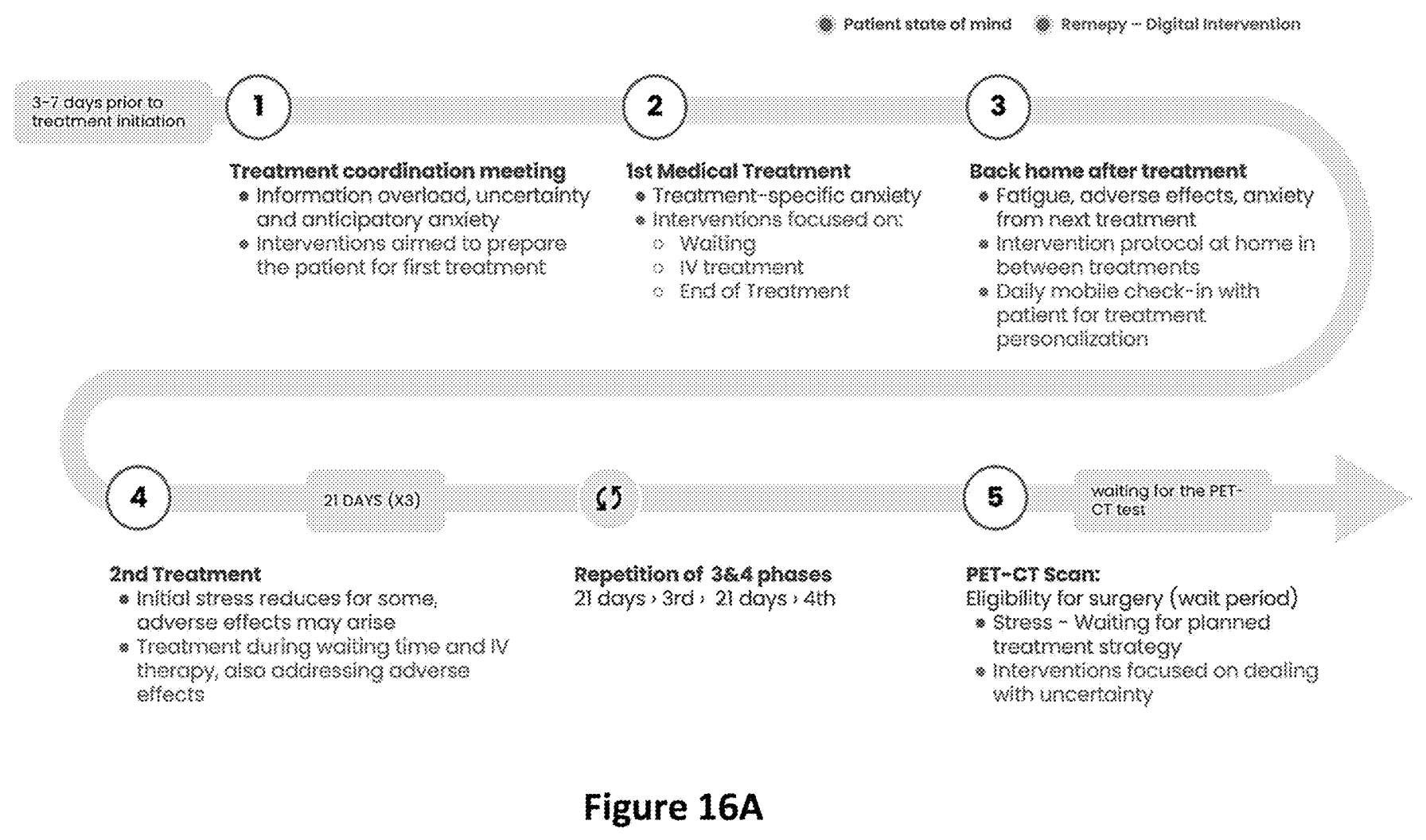

①

Treatment coordination meeting
- Information overload, uncertainty and anticipatory anxiety
- Interventions aimed to prepare the patient for first treatment

②

1st Medical Treatment
- Treatment-specific anxiety
- Interventions focused on:
  - Waiting
  - IV treatment
  - End of Treatment

③

Back home after treatment
- Fatigue, adverse effects, anxiety from next treatment
- Intervention protocol at home in between treatments
- Daily mobile check-in with patient for treatment personalization 21 DAYS (x3)

④

2nd Treatment
- Initial stress reduces for some, adverse effects may arise
- Treatment during waiting time and IV therapy, also addressing adverse effects

↺

Repetition of 3&4 phases
21 days › 3rd › 21 days › 4th

⑤ waiting for the PET-CT test

PET-CT Scan:
Eligibility for surgery (wait period)
- Stress – Waiting for planned treatment strategy
- Interventions focused on dealing with uncertainty

15:34
Skip          Stockholm Maze        >
Level 20
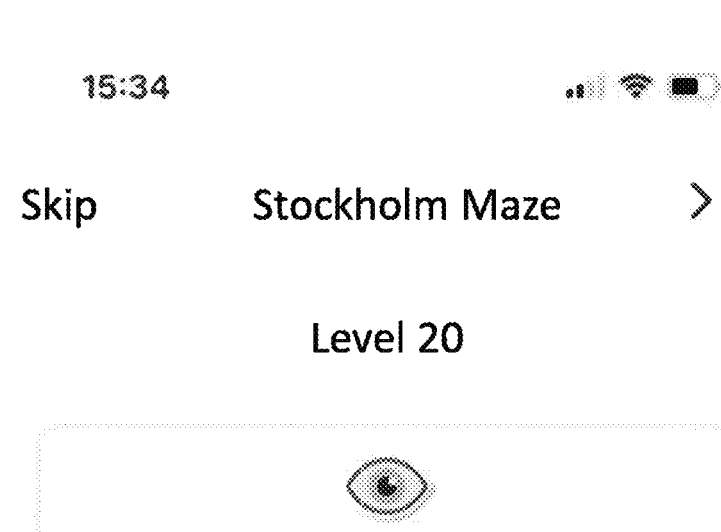
Difficulty level – full sight
Try to remember the path you traverse
Map of the Maze
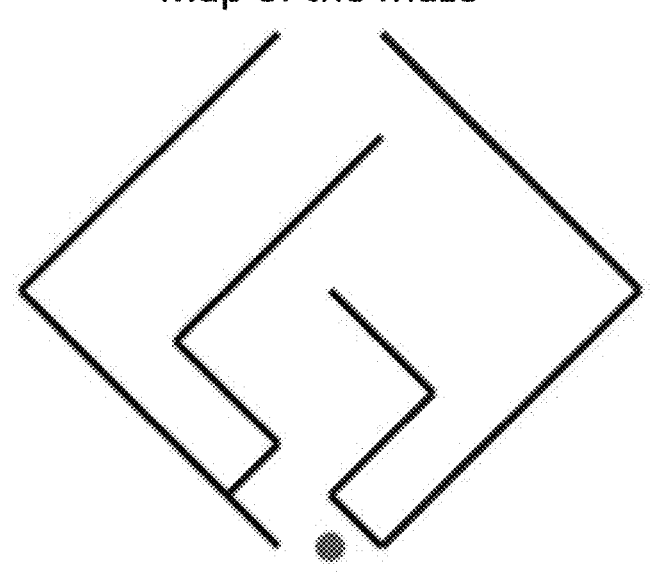
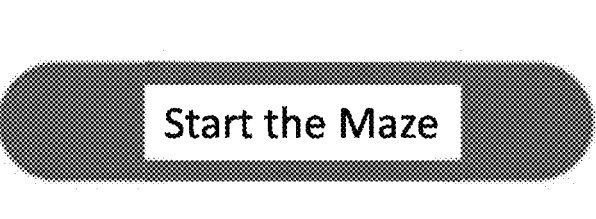
Figure 18I

DIGITAL MAZES IN THERAPEUTICS

FIELD OF INVENTION

The presently disclosed subject matter relates to computer-based methods in the field of digital therapeutics by means of a digital maze. The digital mazes utilize: sensory inhibition, sensory substitution, sensory integration, or a combination thereof. Various digital interventions, their related methods in digital therapeutics and systems are disclosed herein.

BACKGROUND

In today's digital age, the role of digital therapy in supporting brain function is gaining recognition and importance. With smartphones, tablets, and computers becoming ubiquitous in our lives, digital therapy offers convenient and accessible avenues for improving mental well-being. Scientific research indicates that these digital interventions can have significant effects on brain function, from reducing symptoms of anxiety and depression to enhancing cognitive abilities. As more people turn to digital platforms for mental health support, understanding the impact of digital therapy on brain function becomes increasingly crucial.

For ease of demonstrating the utility of the present invention, the description focuses primarily on neuro-degenerative diseases such as Alzheimer's Disease ("AD"), the most common type of dementia. However, the principal approach and tools for treating AD described herein can be implemented with mild cognitive impairment (MCI), which is an early stage of memory loss or other loss of cognitive ability in an individual who maintains the ability to independently perform most activities of daily living, as well as with other types of dementia and neurodegenerative disorders that involve cognitive decline.

Remepy is company which develops digital therapy platforms. Remepy's Digital Molecule™ (DM) is based on cognitive and psychological digital interventions. The DM triggers physiological processes that balance the immune system and boost brain neuroplasticity.

Aims of the present invention include:

Study medical conditions with unmet needs.

Identify psychological, cognitive and physical interventions with proven desired outcomes.

Validate effect via MRI imaging and advanced blood sample analysis.

Digitize the interventions and treatment protocol a platform and mobile app e.g., "Remepy" platform.

Design tailored treatment protocols and interventions.

Enhancing medicine with software:

activates brain mechanisms that modulate the immune system and increase synaptic connectivity & neuroplasticity to improve drug efficacy.

Alzheimer's disease (AD) is a complex neurodegenerative disease characterized by cognitive decline, memory loss, and impaired ability to perform daily activities. AD is the most common form of dementia, affecting millions worldwide. Hallmarks of AD are primarily the accumulation of abnormal protein deposits in the brain, including β-amyloid plaques and neurofibrillary tangles composed of tau amyloid fibrils. These hallmarks may be present up to 20 years before the patient exhibits changes in memory, thinking or behavior. The exact pathogenesis of AD is yet to be fully understood, but it is currently suggested, at least by some scientists, that beta amyloid protein, abnormal tau protein or possibly both play key roles in the development of the disease.

β-amyloid plaques are believed to be a major contributor to the development of the disease, as they can trigger inflammation and oxidative stress, leading to damage and death of brain cells. The accumulation of plaques can also trigger the formation of neurofibrillary tangles and activate microglial cells.

Neurofibrillary tangles are formed by the accumulation of hyperphosphorylated tau protein in brain cells. Tau protein has a critical role in maintaining the structural integrity of the neurons. The presence of tau protein in neurofibrillary tangles results in a loss of its normal function (leading to the dysfunction and death of neurons) and can also lead to activation of microglia.

Neuroinflammation has a prominent role in the pathogenesis of AD. Numerous studies show that microglial cells, a population of innate immune cells that reside in the CNS as the first line of defense against invading pathogens, are causing persistent neuroinflammation and drive irreversible tissue damage in neurodegenerative disorders. Microglial cells are activated by the presence of amyloid plaques and neurofibrillary tangles. Microglial activation can contribute to the progression of the disease by producing proinflammatory molecules and reactive oxygen species, which can result in synaptic dysfunction, neuronal death, and inhibition of neurogenesis. Notably, in people with Alzheimer's disease, reactive microglia have been shown to colocalize closely with amyloid plaques, suggesting an interaction between these two important pathological hallmarks. It has been suggested that microglial activation acts as a bridge leading to the pathological phosphorylation and aggregation of tau protein due to the sequential rise of amyloid plaques, microglial activation and neurofibrillary tangles.

The changes described above in the brain of an AD patient result in synapse loss and neurodegeneration, which leads to a general and progressive loss of cognitive functions. At first, Alzheimer's disease typically destroys neurons and their connections in parts of the brain involved in memory, including the entorhinal cortex and hippocampus. It later affects areas in the cerebral cortex responsible for language, reasoning, and social behavior. Altogether, AD is characterized by disconnectivity between brain areas and the death of neurons, alongside a deficit in multisensory integration and connections between the senses, as well as memory loss and spatial perception.

On the molecular level, AD manifests in downregulation of synaptic genes across multiple brain regions and widespread proteomic signs of synaptic stress or decay in the cerebrospinal fluid (CSF) or blood.

According to the World Health Organization (WHO), dementia is the 7th leading cause of death worldwide, causing 1.6 million deaths in 2019 with a staggering global cost of $1.3 trillion in 2019. Even more strikingly, this figure is growing rapidly, making dementia the number one fastest growing cause of death worldwide. Annual per-patient costs increase with disease severity, meaning that aging populations reaching later stages of dementia are putting additional strain on the system. As a result, the global cost of dementia is predicted to reach $2.8 trillion by 2030.

There is currently no treatment that can prevent or cure cognitive disease. Treatment of Alzheimer's disease currently involves managing patient symptoms and wellbeing. No widely used therapies can prevent or slow down disease progression, but several drugs targeting cognitive symptoms can reduce or stabilize a patient's condition for a limited timeframe. These include cholinesterase inhibitors such as donepezil or the glutamate regulator memantine (an NMDA antagonist), all of which were first approved around two decades ago. Since the cholinesterase inhibitors were approved, there have been numerous attempts to target disease progression with novel therapeutics. However, the failure of large scale Phase 3 clinical trials, often following mixed signals in Phase 2, has become a regular occurrence.

In 2021, the US Food and Drug Administration (FDA) granted approval to aducanumab, an antiamyloid antibody for early-stage Alzheimer's disease, despite a lack of clear clinical evidence demonstrating the drug's cognitive benefits. A second antiamyloid antibody, Lecanemab, was approved in 2023. However, the Centers for Medicare and Medicaid Services (CMS) recently announced that they will only cover individuals enrolled in clinical trials and will limit coverage of future antiamyloid antibodies, based on the high risk-benefit profile of the drugs.

In July of 2023, Lecabemab became the first amyloid beta-directed antibody to be converted by the FDA from an accelerated approval to a traditional approval for the treatment of Alzheimer's disease, following determination that a confirmatory trial verified clinical benefit. Lecanemab is approved for patients with mild cognitive impairment or mild dementia stage of Alzheimer's disease, the population in which treatment was studied in clinical trials. The treatment is now eligible for Medicare/Medicaid coverage under certain conditions.

As such, the present disclosure provides methods for increasing neuroplasticity in an individual, primarily with a digital platform. Data is provided throughout to demonstrate the effectiveness of the digital therapy plans of the invention. As will become clear, the benefits to digital therapy interventions reach beyond merely neurological, but are also relevant for immune-related diseases and their corresponding interventions. The invention discloses aspects of personalization and combination with drug therapies to improve patient outcomes.

SUMMARY

In one embodiment the invention provides a computer-implemented method for digital therapy for an individual, said method comprising:
  presenting the individual with a digital maze on a personal electronic device;
  wherein the personal electronic device provides sensory modality inputs selected from: visual, auditory, tactile, or a combination thereof, to enable the individual to navigate the digital maze from a starting point to a finishing point.

In one embodiment the digital maze comprises at least one obstacle selected from: outer wall, inner wall, dead end, object, turn, interconnected paths, or a combination thereof.

In one embodiment the sensory modality inputs are configured to assist said individual in completing said digital maze in the shortest time, shortest path, with fewest obstacle impacts, or a combination thereof. In one embodiment the digital maze is presented to the individual to be repeated at least once. In one embodiment the method further comprises generating a performance score upon completion of each repeat of said digital maze by taking into consideration the time taken, path taken, the number of obstacle impacts of the individual, or a combination thereof, when navigating said at least one digital maze.

In one embodiment the method further comprises generating a threshold performance score for the digital maze, above which the individual is no longer presented with the digital maze to complete. In one embodiment the method further comprises the personal electronic device providing a plurality of the digital mazes wherein an increase in sensory substitution is exhibited for each digital maze in the plurality of the digital mazes, following the completion of each digital maze and/or the threshold performance score being achieved; and
  wherein the sensory substitution comprises the personal electronic device providing the at least partial substitution of at least one of the sensory modality inputs with at least one other of the sensory modality inputs.

In one embodiment the method further comprising the complete substitution of one of said sensory modality inputs with at least one other of said sensory modality inputs selected from:
  visual to auditory and/or tactile;
  auditory to visual and/or tactile;
  tactile to visual and/or auditory.

In one embodiment the personal electronic device is configured to enable the individual to carry out the navigation by means of touch gesture, motion gesture, voice commands, text input, camera and media interaction, sensor-based interactions, or a combination thereof. In one embodiment the touch gesture is selected from: tapping, swiping, scrolling, pinching, dragging, double-tapping, or a combination thereof. In one embodiment the motion gesture is selected from: tilting, shaking, rotating, body motion, waving, or a combination thereof. In one embodiment the auditory input is selected from: a change in pitch, change in loudness, change in tone, change in melody, change in rhythm, change in music or a combination thereof.

In one embodiment the method further comprises at least one additional device selected from: haptic device, external speakers, headphones, virtual reality set, augmented reality glasses/devices, biofeedback sensors, wearable activity trackers, smartphone, personal computational device, smart speakers, voice assistants, motion tracking sensor, virtual assistant systems, internet hub, or a combination thereof; wherein said at least one additional device is configured to transfer data between said individual, said personal electronic device, or a combination thereof.

In one embodiment the personal electronic device, said at least one additional device, or a combination thereof, are configured to provide said sensory modality inputs. In one embodiment the tactile cue is a vibration. In one embodiment the method further comprises the personal electronic device providing a plurality of digital mazes of increasing difficulty following the completion and/or achievement of said threshold performance score, for each digital maze.

In one embodiment the method further comprises the personal electronic device providing an increase in sensory substitution exhibited for each of said digital maze of increasing difficulty;
  wherein the sensory substitution comprises the personal electronic device providing the at least partial substitution of at least one of the sensory modality inputs with at least one other of said sensory modality inputs.

In one embodiment the method further comprises the complete substitution of one of said sensory modality inputs with at least one other of said sensory modality inputs selected from:
  visual to auditory and/or tactile;
  auditory to visual and/or tactile;
  tactile to visual and/or auditory.

In one embodiment the increasing difficulty is achieved by: randomly generating a digital maze of a different structure, increasing the path length, increasing the number of turns, increasing the number of obstacles, diversifying the types of obstacles, decreasing the path width, incorporating a time challenge, increasing the performance threshold score, changing the sensory modality inputs, adding interactive elements, incorporating distractions, incorporating tasks, incorporating moving obstacles, or a combination thereof.

In one embodiment the digital maze comprises between 1 and 1,000,000,000 obstacles. In one embodiment the obstacles are stationary, moving, or a combination thereof. In one embodiment the method further comprises delivering instructions to said individual before, during, after, or a combination thereof, said digital maze. In one embodiment the personal electronic device is selected from: smartphones, tablets, wearable device, smart TVs, computers, laptops, E-readers, gaming consoles, smartwatches, fitness trackers, portable media players, digital cameras, virtual reality (VR) headsets, augmented reality (AR) device, portable GPS devices, portable Bluetooth devices, portable digital assistant, smart glasses and audio device or any combinations thereof. In one embodiment the method is for use in a digital therapy intervention.

In one embodiment the digital therapy intervention comprises: sensory inhibition, sensory substitution, sensory integration, or a combination thereof, to said individual. In one embodiment the digital therapy comprises at least one digital therapy intervention comprising: sensory inhibition, sensory substitution, sensory integration, or a combination thereof. In one embodiment the sensory inhibition comprises the at least partial suppression of at least one sensory modality input. In one embodiment the at least one sensory modality input is selected from: visual, auditory, and tactile. In one embodiment the sensory substitution comprises the at least partial replacement of at least one sensory modality input with at least one other sensory modality input. In one embodiment the at least partial replacement of at least one sensory modality input with at least one other sensory modality input is selected from:

visual to auditory and/or tactile;

auditory to visual and/or tactile; and tactile to visual and/or auditory.

In one embodiment the sensory integration comprises the at least partial combination of at least two sensory modality inputs. In one embodiment the at least two sensory modality inputs are selected from: visual, auditory, and tactile.

In one embodiment the method further comprises gamification elements. In one embodiment the gamification elements are selected from: badges, scores, leader-boards, ranking, game currencies, quests or missions, characters or avatars, virtual goods, social media features, experience points (XP), or a combination thereof.

In one embodiment the invention provides a digital therapy system comprising:

at least one processor of at least one personal electronic device, said at least one personal electronic device comprising an internal storage system; and a software application for a digital therapy intervention which performs the computer-implemented method of claim 1.

In one embodiment the digital therapy intervention comprises a plurality of intervention sessions. In one embodiment the system further comprises digitally stored instructions for said digital therapy intervention;

wherein said at least one processor is configured to perform said digitally stored instructions causing said software application to perform functions on said personal electronic device, and wherein said software application is further configured to:

receive user inputs via a plurality of interactive elements;

process said user inputs and transfer data between said internal storage system and said software application to carry out said plurality of intervention sessions; and display a graphical user interface (GUI) on said personal electronic device related to said digital therapy intervention.

In one embodiment the system further comprises at least one analysis tool based on machine learning, artificial intelligence (AI), statistical modeling, or a combination thereof, configured to analyze said data for analysis and personalization of said digital therapy intervention.

In one embodiment the system further comprises at least one external storage system. In one embodiment the at least one external storage system is selected from: databases, USB storage, network-attached storage (NAS), cloud server, online repositories, or a combination thereof. In one embodiment the plurality of interactive elements are selected from: user commands, user selections, data input, or a combination thereof. In one embodiment the GUI is presented to said user in a format selected from: text, images, video, audio, or vibration, in response to user interactions and/or information regarding said software application. In one embodiment the GUI is configured to adapt its presentation format based on the individual's device type, accessibility settings, past user interactions, or a combination thereof.

In one embodiment the system is further configured to perform a plurality of background tasks. In one embodiment the plurality of background tasks are selected from: maintaining application functionality, data synchronization, updates, notification delivery to the user, system monitoring, error logging, cache management, security checks, data encryption, or a combination thereof. In one embodiment the at least one processor is configured to onboard, transfer, analyze, or a combination, data selected from: user interactions, user preferences, user demographics, user usage patterns, user feedback, timestamps, data from said plurality of intervention sessions, or a combination thereof. In one embodiment the system further comprises at least one wireless network device configured to transfer data wirelessly.

In one embodiment the at least one wireless network device is selected from: Wi-Fi adapter, cellular modem, Bluetooth module, near field communication chip (NFC), wireless local area network (LAN) card, wireless router, and wireless access point. In one embodiment the system is further configured to carrying out said digital therapy intervention in any of the following formats: instructional video, interactive video comprising input and feedback from the individual, game, instructional prompts, question and answer survey with feedback, virtual reality, augmented reality, or a combination thereof.

In one embodiment the system further comprises at least one additional device selected from: health monitoring system, medical device, haptic device, external speakers, headphones, virtual reality set, augmented reality glasses/devices, biofeedback sensors, wearable activity trackers, smartphone, personal computational device, smart speakers, voice assistants, motion tracking sensor, virtual assistant systems, internet hub, or a combination thereof; wherein said at least one additional device is configured to transfer data between said individual, said personal electronic device, or a combination thereof.

In one embodiment the system is further configured to transfer data between said at least one additional device and said system to personalize said digital therapy intervention.

In one embodiment the health monitoring system is selected from: wearable fitness trackers, remote patient monitoring (RPM) systems, telemedicine platforms, smart health devices, health and wellness apps and hospital information systems (HIS).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A-1B depicts screenshots of a digital maze. FIG. 1A and FIG. 1B show different angles of first-person perspective of the same maze.

FIG. 2A shows six mazes with the same start-finish positions but with internal walls in different positions. FIG. 2B shows another set of twelve mazes with varying complexity. FIG. 2C shows a digital maze configuration where the user needs to navigate along a corridor where the width of the corridor changes (entry and exit points are marked with an arrow). FIG. 2D shows a digital maze configuration where more than one path can be taken to arrive at the finishing point (entry and exit points are marked with an arrow).

FIG. 4A, shows the left hippocampus seed map. FIG. 4B shows the right parahippocampal area seed map. (POST>PRE-intervention of the resting state brain imaging data—group level, n=17, $P_{FDR}$<0.05, parametric stats, two sided). FIG. 4C shows the correlation between the changes in training score and increased PHA3-dACC post training connectivity. PHA-Parahippocampal area, dACC-dorsal anterior cingulate cortex.

FIG. 5A shows the retro splenial complex (RSC) seed which integrates both egocentric and allocentric spatial information streams. Improved post-training rsFC was found in both egocentric and allocentric networks (k=211, $P_{FDR}$<0.002 and k=175, $P_{FDR}$<0.004 respectively); (POST>PRE-intervention of the resting state brain imaging data—group level, n=17, $P_{FDR}$<0.05, parametric stats, two sided). FIG. 5B shows bar graphs of cluster Fisher's Z effect size connectivity values, error bars, CI.

FIG. 8A shows the default mode network (DMN), and salience network (SN) are anticorrelated in the healthy non-depressed brain. Intra-network connections and inter-network connections are presented as lines. FIG. 8B shows decreased post-intervention intra-network connectivity (z-score: 0.64±0.28 to 0.59±0.23, p<0.002) within the DMN. FIG. 8C shows the improved CES-D depression score (negative change mark improvement in the depression state for the post vs. pre assessment) was correlated with increased negative internetwork DMN-SN rsFC. This suggests correlation between how much individuals subjects improved in the depression and how much their connectivity pattern is healthier (i.e. reflect more anti-correlation between DMN and SN (as in depressed subjects this anticorrelation is lost).

FIG. 9C shows how digital therapy enhances rsFC of the basal ganglia (seed: Globus pallidus internalis) and frontal brain regions, known to be impaired in Parkinson's disease. FIG. 9D-9F shows improved connectivity within the basal ganglia network and between somatosensory brain regions (seed: Putamne) (POST>PRE-intervention of the resting state brain imaging data—group level, n=17, $P_{FDR}$<0.05, parametric stats, two sided).

FIG. 12A shows a graphical representation of the reduction in IL-17 with the digital therapy interventions of the present invention in blood samples. FIG. 12B shows a graphical representation of the reduction in IL-18 with the digital therapy interventions of the present invention in saliva samples.

FIGS. 13A and 13B show brain scans showing increased post-intervention connectivity between the amygdala and the left and the right mPFC (POST>PRE-intervention of the resting state brain imaging data—group level, n=27, $P_{FDR}$<0.05, parametric stats, two sided). FIG. 13C shows bar graphs of cluster Fisher's Z effect size connectivity values, error bars, CI. FIG. 13D shows a graphical representation showing significant correlation between the Amygdala—mPFC rsFC and improvement in psychological scores for depression, compared to controls. FIG. 13E shows a graphical representation showing significant correlation between the Amygdala—mPFC rsFC and improvement in psychological scores for well-being, compared to controls. FIG. 13F shows a graphical representation for significant correlation between the Amygdala—mPFC rsFC and improvement in psychological scores for stress, compared to controls.

FIGS. 14A-14D shows further results for significant functional connectivity changes, in correlation with psychological improvement. FIG. 14A shows brain scans of decreased post-intervention connectivity between the right amygdala and the left precuneus/Superior Parietal Lobule. FIGS. 14B and 14C show cross-sections of the brain scan of FIG. 14A (POST>PRE-intervention of the resting state brain imaging data—group level, n=27, $P_{FDR}$<0.05, parametric stats, two sided). FIG. 14D shows a graphical representation showing significant correlation between the Amygdala—Precuneus rsFC and improvement in psychological scores for stress, compared to controls.

FIG. 15A and FIG. 15A shows an rsFC regression analysis showing significant correlation between post-intervention increase between the Hippocampus—dACC rsFC and improvement in IL-18 levels. FIG. 15C and FIG. 15D shows an rsFC regression analysis showing significant correlation between post-intervention increase between the ParaHippocampus—mPFC rsFC and improvement in IL-18 levels.

Figure 16C:
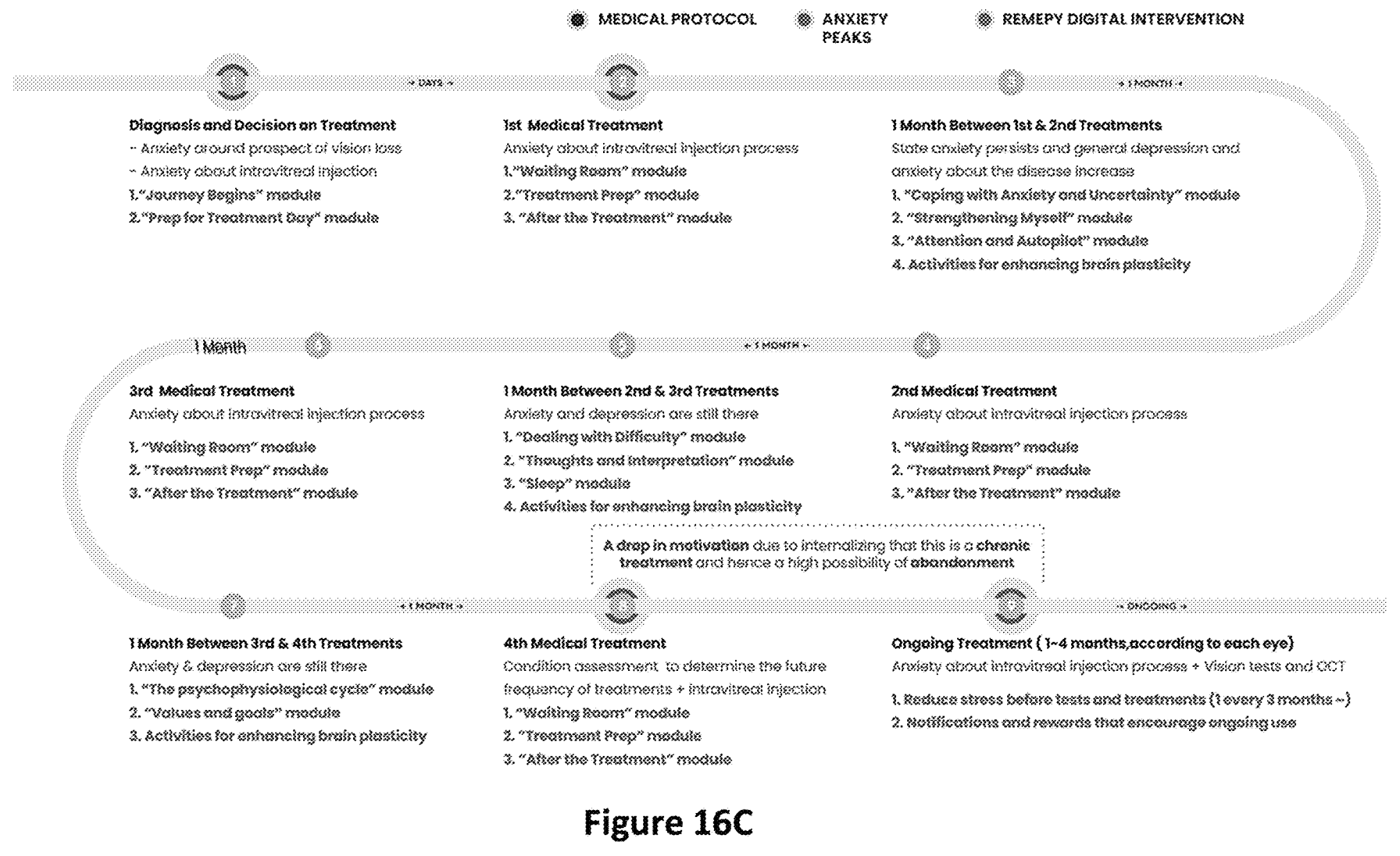

FIGS. 16A-16C shows an example of a tailor-made treatment protocol for perioperative ICB treatment in the form of a flow chart. The sequence of the treatment protocol is shown in FIG. 16A and then FIG. 16B. FIG. 16C shows a separate treatment protocol, also referred to as patient journey from diagnosis and decision on treatment to ongoing treatment.

FIG. 17A shows a start-screen on a mobile phone app showing the path required for the digital maze. FIG. 17B shows a first-person screenshot of a user navigating a digital maze. FIG. 17C shows a screenshot of a digital maze which is partly clouded, one way of decreasing reliance on visual cues for navigation in the maze. FIG. 17D shows a screen-shot of a digital maze which is heavily clouded. FIG. 17E shows a screenshot of an instructional video, on the platform of the mobile phone application.

FIGS. 18A-18I shows screenshots from a mobile phone app developed by Remepy. FIG. 18A shows a home screen on a mobile phone app. FIG. 18B shows a 'welcome' screen. FIG. 18C shows an 'explore' tab to browse categories. FIG. 18D shows tabs to access different digital interventions. FIG. 18E shows a wellness 'range slider' feature. FIG. 18F shows a symptoms prompt menu. FIG. 18G shows features in a "safe place" tab. FIG. 18H shows a landing screen on a mobile phone app. FIG. 18I shows a start screen before a user carries out a digital maze.

Figure 2A:
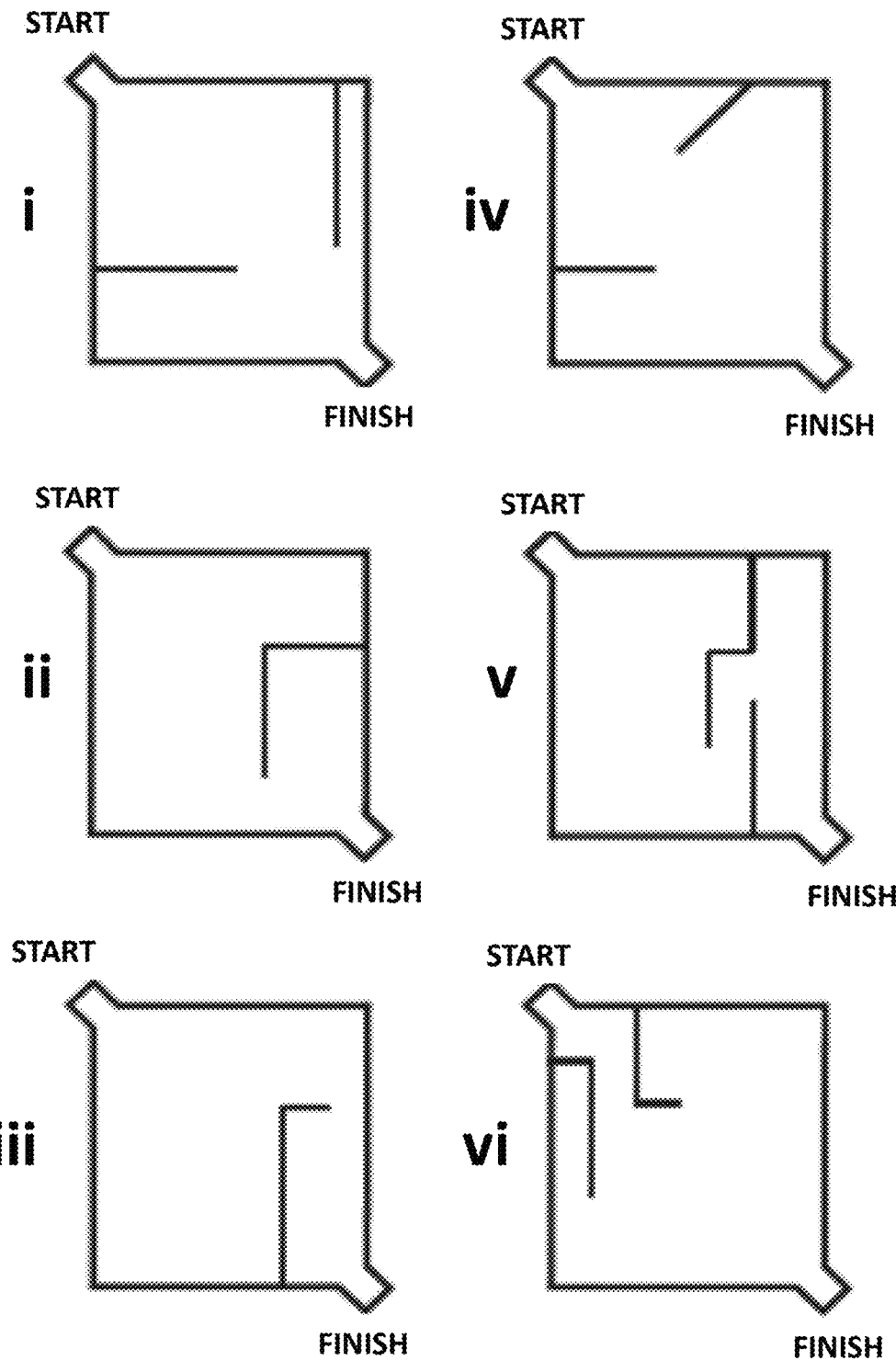
FIGS. 2A-2D illustrate schematic representations of digital mazes of varying complexity.

For simplicity and clarity of illustration, elements shown in the figures are not necessarily drawn to scale, and the dimensions of some elements may be exaggerated relative to other elements. In addition, reference numerals may be repeated among the figures to indicate corresponding or analogous elements.

DETAILED DESCRIPTION

To provide a thorough understanding of the present invention, specific configurations, and details are set forth below. However, it will also be apparent to one skilled in the art that the present invention may be practiced without the specific details presented herein. Various examples, which are given throughout this description, are merely descriptions of specific embodiments of the invention, but the scope of the invention is not limited to such examples. Any brand names of drugs mentioned throughout this description are solely for demonstrative purposes.

As used in this description of the present invention, the terms "drug" or "drug therapy" shall encompass treatment with any medication, whether approved or not by the relevant regulatory authorities (such as the FDA).

For ease of demonstrating the utility of the present invention, the description focuses primarily on neuro-degenerative diseases such as Alzheimer's Disease ("AD"), the most common type of dementia. However, the principal approach and tools for treating AD described herein can be implemented with mild cognitive impairment (MCI), which is an early stage of memory loss or other loss of cognitive ability in an individual who maintains the ability to independently perform most activities of daily living, as well as with other types of dementia and neurodegenerative disorders that involve cognitive decline.

Neuro-degenerative disorders form a broad category of diseases characterized by the progressive degeneration and/or dysfunction of nerve cells (neurons) in the brain or peripheral nervous system. These disorders typically result in a gradual decline in cognitive function, movement control, or other neurological processes over time. Examples of neurodegenerative disorders include Alzheimer's disease, Parkinson's disease, Huntington's disease, amyotrophic lateral sclerosis (ALS), and multiple sclerosis (MS). While the specific causes and mechanisms underlying each disorder does vary, they often involve the accumulation of abnormal protein aggregates, oxidative stress, inflammation, and genetic factors, or combinations of those factors.

Digital Therapy to Improve Neuro-Connectivity

The present invention provides a method for improving neuro-connectivity in an individual. In some embodiments, the terms "neuro-connectivity" and "neuro-plasticity" are used interchangeably since their effects are correlated. "Neuro-plasticity" generally refers to the brain's ability to reorganize itself by forming new neural connections in response to interventions, learning, experience, and environmental changes, etc. "Neuro-connectivity" generally refers to the interconnectedness and communication pathways between different regions of the nervous system, particularly the brain. As will become clear, the interventions aim to improve neuro-connectivity, neuro-plasticity, or a combination thereof. As used herein, "neuro-connectivity" is also referred to as "synaptic connectivity", "brain connectivity" or the likes. As used herein, the terms "increase", "improve" and "modulate" are used interchangeably when the effect is the same. For example, if increasing neuro-connectivity also improves neuro-connectivity then the terms are considered interchangeable. However, of the various markers disclosed here, an 'increase' in a particular marker refers to a 'decrease' in a particular effect.

In one embodiment the invention provides a method for increasing neuro-connectivity in an individual, the method comprising:

the individual carrying out at least one digital intervention comprising: sensory inhibition, sensory substitution, sensory integration, or a combination thereof.

In one embodiment the invention provides a method for increasing neuro-connectivity in an individual, the method comprising:

the individual carrying out a digital therapy intervention plan comprising at least one digital intervention comprising: sensory inhibition, sensory substitution, sensory integration, or a combination thereof.

In one embodiment the at least one digital intervention is comprised within a digital therapy intervention plan.

In one embodiment the invention provides a method for increasing neuro-connectivity in an individual, the method comprising: carrying out at least one digital intervention comprising sensory inhibition. In one embodiment the invention provides a method for increasing neuro-connectivity in an individual, the method comprising: carrying out at least one digital intervention comprising sensory substitution. In one embodiment the invention provides a method for increasing neuro-connectivity in an individual, the method comprising: carrying out at least one digital intervention comprising sensory integration. As understood herein, sensory inhibition, substitution and integration can be used separately or in any combination, for carrying out digital interventions. Personalization of an individual's digital therapy intervention plan will be tailored to the individual person, although general guiding principles can be used to design an intervention plan. As will be described, digital intervention plans can be generally utilized using the three principles of sensory inhibition, substitution and integration, via a plurality of digital interventions; some being based on cognitive interventions, psychological interventions, physcail interventions, or combinations thereof.

As used herein, the subject using or undergoing the digital therapy interventions is referred to in a number of ways. For example, a "user" can also be referred to, and understood interchangeably, as a "patient", "individual", "subject", "participant", "recipient".

In one embodiment the method of increasing neuro-connectivity in an individual comprises at least one cognitive intervention. In one embodiment the method of increasing neuro-connectivity in an individual comprises at least one psychological intervention. In one embodiment the method of increasing neuro-connectivity in an individual comprises at least one physical intervention. In one embodiment the digital intervention comprises: at least one psychological intervention, at least one cognitive intervention, at least one physical intervention, or a combination thereof. In one embodiment the digital intervention comprises at least one cognitive intervention and at least one psychological intervention. In one embodiment the digital intervention comprises at least one cognitive intervention and at least one physical intervention. In one embodiment the digital intervention comprises at least one psychological intervention and at least one physical intervention.

As referred to herein, "digital interventions" refer to the at least partial use of a digital platform to carry out a therapeutic intervention. "Digital interventions" is understood in a similar manner, no matter what digital intervention, or combination intervention, is described e.g., the term can be used for methods to increase neuro-connectivity, improve immune function, etc. In various embodiments digital interventions refer to the use of digital technologies, such as mobile applications, web-based platforms, virtual reality, or wearable devices, to deliver therapeutic interventions aimed at improving mental health, physical well-being, managing medical conditions, or a combination thereof. These interventions can include cognitive-behavioral therapy, mindfulness exercises, guided meditation, remote monitoring of health metrics, personalized health coaching, and other forms of support or treatment delivered through digital channels, as will be described. In various embodiments, the terms "digital therapy" and "digital intervention" are understood interchangeably in that both refer to the use of digital technologies to deliver therapeutic interventions aimed at improving mental health, physical well-being, or managing medical conditions. Correspondingly, phrases such as "digital therapy plan", "digital therapy intervention plan", "digital therapy course" and "digital therapy schedule" are to be understood interchangeably in view of the definitions disclosed herein. In one embodiment the "digital therapy intervention plan" refers to a plurality of digital therapy interventions. In one embodiment the digital therapy intervention plan comprises at least one digital intervention. In one embodiment the digital therapy intervention plan comprises a plurality of digital interventions. In some embodiments, the digital therapy intervention plan comprises not only digital interventions, but also comprises non-digital therapy interventions.

Digital therapy interventions are also referred to herein as 'sessions'. In one embodiment the plurality of sessions ranges between 1 and 10 digital therapy interventions. In one embodiment the plurality of sessions ranges between 1 and 100 digital therapy interventions. In one embodiment the plurality of sessions ranges between 1 and 1000 digital therapy interventions. In one embodiment the plurality of sessions ranges between 1 and 10,000 digital therapy interventions. In one embodiment the plurality of sessions ranges between 1 and 100,000 digital therapy interventions. In one embodiment the plurality of sessions ranges between 1 and 1,000,000 digital therapy interventions.

In one embodiment the digital intervention comprises, at least one psychological intervention, at least one cognitive intervention, at least one physical intervention, or a combination thereof. As used herein "cognitive" interventions are generally directed towards interventions that utilize tasks that affect cognition, brain function, etc. As such, cognitive interventions are generally related to reasoning tasks, memory improvement interventions, sensory interventions, and the likes, as will be described. In various embodiments the cognitive interventions may be understood as 'neuro-cognitive'; a key idea being that some interventions are psychological in nature and often geared towards reducing stress and other types of discomfort whereas others are geared towards enhancing connectivity. It is noted that any new learning provides new neuro-connectivity.

As used herein "psychological" interventions are generally directed towards interventions that affect psychological and/or behavioral aspects of an individual. As such, psychological interventions are generally related to behavioral, social and psychological tasks, as will be described. As used herein "physical" interventions are generally directed towards interventions that improve motor functions in an individual.

All of the psychological, cognitive, physical interventions, or a combination thereof, utilize any of the following: sensory inhibition, sensory substitution, sensory integration, or a combination thereof, on a digital platform. This is also referred to as the 'sensory principles' i.e., interventions that rely on sensory inhibition, sensory substitution, sensory integration, or a combination thereof. Thus, the 'sensory principles' utilized for different purposes in various embodiments of the invention are used in an equivalent manner, in one embodiment. For example, the psychological interventions that utilize the sensory principles can also be used for cognitive and/or physical interventions. However, the particular implementation of the sensory principles for each intervention, or plurality of interventions, will vary from individual to individual and/or from disease/disorder to disease/disorder.

The various embodiments the digital interventions are carried out on a personal electronic device. As will become clear, the digital interventions may also be carried out on at least one personal electronic device, depending on the type of intervention and/or intervention plan. These personal electronic devices can be used in any of the digital therapy intervention plans disclosed in the present invention and for any of the stated purposes e.g., increasing neuro-connectivity, improving immune function, improving motor skills, etc. As used herein, the term "personal electronic device" is understood to be any electronic device used by a user to carry out any part of the digital intervention. Thus, although it is often a 'personal' device, it is also understood to include devices that are not directly owned by the user, but those that are used/synced for the user to implement the digital intervention. The following are examples of personal electronic device, but are not limited to: smartphones, tablets, wearable device, smart TVs, computers, laptops, E-readers, gaming consoles, smartwatches, fitness trackers, portable media players, digital cameras, virtual reality (VR) headsets, augmented reality (AR) device, portable GPS devices, portable Bluetooth devices, portable digital assistant, smart glasses and audio device or any combinations thereof. In various embodiments the personal electronic device is a mobile computing device.

The data utilized by the presently described methods include a whole variety of data types to implement the digital therapy interventions. These data, corresponding analyzes, and adaptation plans, are thus used for any of the digital therapy intervention plans disclosed herein, for any of the stated purposes e.g., increasing neuro-connectivity, improving immune function, improving motor skills, etc. In various embodiments it is understood that the methods described herein are carried out on corresponding systems, devices, over networks, and the likes, to carry out the data transfer and data analysis required to carry out the methods of the invention. As understood herein, the term "transfer of data" includes any of the following selected from: sending, receiving, sharing, syncing, backing up, restoring, importing/exporting data by any means. As such, the method further comprises the transfer of data for an individual wherein the data is selected from: personal, demographic, medical, biomarker information, medicinal agent intake and dosage regimen, geographic, environmental, lifestyle, health and wellbeing, biometric, behavioral, digital intervention related data, goal setting, medical considerations, health and wellbeing, preferences, availability, time constraints, scheduling, individual's strengths and weaknesses, cultural considerations, communication channel preference, feedback from said individual, feedback from healthcare provider, or a combination thereof.

In various embodiments, the data inputs for the digital therapy can be in any form. Examples of data include, but are not limited to: name, age, sex, gender, marriage status, ethnicity, race, children, socioeconomic status, occupation, geographic location, pain location, pain frequency, pain intensity, pain type, disability status, anxiety rating, type of medical intervention, medicine dosage, date, time, sleep cycle, calendar entry, side effects, allergies, concurrent medications, symptoms or changes thereof, diet, lifestyle factors, laboratory test results, medical intervention schedule, weight, height, mental health, general medical health, medication list, diet, exercise regimen, existing medical conditions, genetic information, lifestyle factors, daily activities, adherence to protocols, medical appointment schedule or any combinations thereof. Each one of these data categories will be related to other data categories. For example, an anxiety score (or 'rating') will be related to any of the following, but not limited to: elevated pulse rate, tightness in the chest, shortness of breath, choking feeling, shuddering, sweating, dizziness, nausea, reflux, tingling, stomach ache, body ache, lack of appetite, elevated temperature, or combinations thereof.

The data can be received before, during and/or after any of the interventions described herein. The data can also be in-built into the corresponding digital therapy programs or input by the individual him/herself or an administrator, or other.

As such, methods of the invention further comprises analyzing the data, in any of its forms, to adapt the digital intervention (and/or its corresponding plan) to that individual. In one embodiment the method comprises analyzing the data by means of machine learning, artificial intelligence (AI), statistical modeling, or a combination thereof, to adapt said at least one digital intervention to said individual at the outset of said method producing a digital therapy intervention plan. In one embodiment the method comprises analyzing the data by means of machine learning, artificial intelligence (AI), statistical modeling, or a combination thereof, to adapt the digital therapy intervention plan. As understood herein, the "digital therapy intervention plan" relates to a plan comprising at least one digital intervention for an individual. The terms "digital therapy intervention plan", "intervention plan", "digital therapy plan", and the likes, are used interchangeably. For example, a digital therapy intervention plan can comprise a plurality of digital interventions. Digital interventions are also referred to herein as "sessions". A digital therapy plan is a structured program comprising a series of digital interventions/sessions designed to address specific mental health or wellbeing need of an individual. As will be shown, the digital therapy intervention plan takes various factors into consideration such as any of the following: initial assessment, goal setting, intervention selection, timing, dosage and frequency, regimen, schedule, progress tracking, adjustments and adaptations, support resources, integration with other treatments, etc. For example, the initial intervention plan for a particular disease may be generic and will adapt according to the individual's progression through the intervention plan. Different individuals will perform and react differently to an initial standardized plan. As such, in one embodiment, the digital intervention plan is standardized at the outside. In other embodiments, the data onboarded is used to personalize a digital intervention plan at the outset. Furthermore, the digital intervention itself may be personalized as well as the digital intervention plan, all in accordance to the individual's needs and goals, as will be explained.

In one embodiment the analyzing determines a degree of improvement to be achieved by the individual carrying out said digital therapy intervention plan. In one embodiment the analyzing is for adapting the digital intervention. In one embodiment the method further comprises delivering instructions to the individual before, during and/or after any stage of the digital therapy intervention plan. The analysis function applies to any of the digital therapy intervention plans, for any of the stated purposes e.g., increasing neuro-connectivity, improving immune function, improving motor skills, etc.

In one embodiment the digital interventions comprise at least one psychological intervention. As understood herein, a variety of psychological interventions can be used for the digital intervention; the lists provided are examples of many of them, however, different combinations are used according to the aims and purposes of the intervention. Therefore, although lists of interventions are provided, it is understood that some of those specific interventions may be excluded, if not relevant for a particular individual's digital intervention. Examples of psychological interventions include, but are not limited to: guided imagery, psychoeducation, psychotherapy, cognitive behavioral therapy, stress and anxiety management training, mindfulness-based interventions, body scanning training, sleep hygiene, fatigue training, acceptance and commitment therapy (ACT), dialectical behavior therapy (DBT), psychodynamic therapy, solution-focused brief therapy (SFBT), narrative therapy, pain therapy, addiction therapy, gestalt therapy, behavioral activation therapy, telepsychiatry and teletherapy or a combination thereof. In one embodiment the psychological intervention is attention training.

Figure 19:
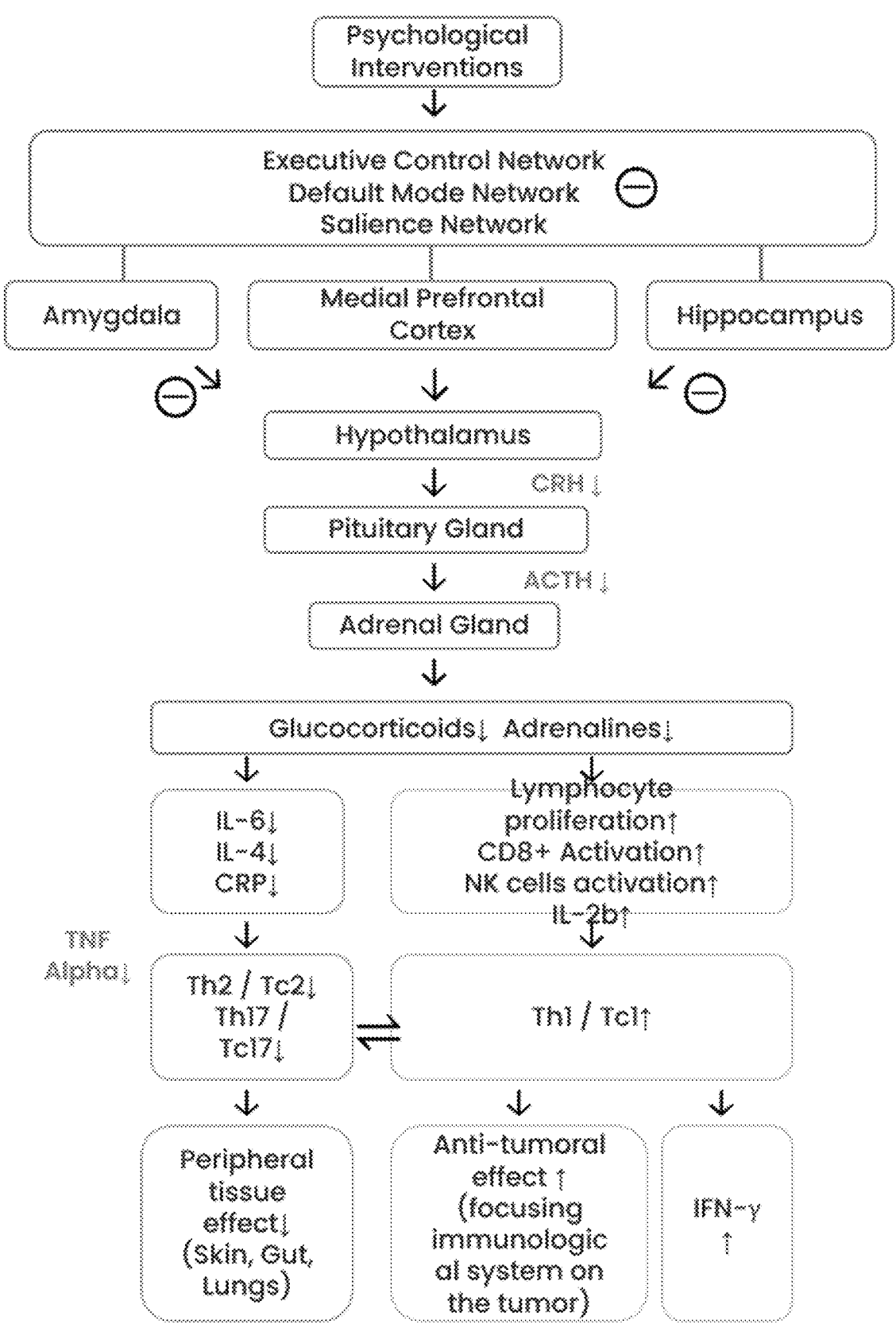
FIG. 19 shows various bodily networks that are affected by psychological interventions, together with a selection of biomarkers that are affected correspondingly.

FIG. 19 shows various bodily networks that are affected by psychological interventions, together with a selection of biomarkers that are affected correspondingly. The Figure shows the interconnectedness of these biomarkers and whether they increase or decrease in response to psychological interventions.

In various embodiments "psychoeducation" is an intervention that provides individuals with information and tools to better understand and manage their mental health conditions or concerns. "Body scanning training" typically refers to a mindfulness practice where individuals systematically focus their attention on different parts of their body, often starting from the toes and moving upward to the head. This practice aims to increase awareness of bodily sensations, promote relaxation, and cultivate a deeper connection between mind and body. It is commonly used as a technique in mindfulness-based stress reduction (MBSR) programs and other mindfulness-based interventions.

In one embodiment the digital interventions comprise at least one cognitive intervention. As understood herein, a variety of cognitive interventions can be used for the digital intervention; the lists provided are examples of many of them, however, different combinations are used according to the aims and purposes of the intervention. Therefore, although lists of interventions are provided, it is understood that some of those specific interventions may be excluded, if not relevant for a particular individual's digital intervention. Examples of cognitive interventions include, but are not limited to: navigation in a maze, spatial navigation, magic-7 training, memory enhancement techniques, attention training, problem-solving, sonification exercise, data visualization, geometric puzzles, shape and pattern matching, visual perception tasks, spatial reasoning games, face detection training, drawing game, focus training, reading training, or any combination thereof.

Magic-7 training refers to a cognitive exercise or game designed to challenge and improve memory recall skills. In this game, participants are presented with a list of seven random items or pieces of information to memorize. After a brief period of time to study the list, the items are hidden or removed, and participants are asked to recall as many items from the list as possible. As understood herein, the sensory principles may be applied for magic-7 memory training e.g., a user is asked to recall seven items on a screen, after which, some items are replaced with auditory cues which the user needs to remember, etc.

In one embodiment the digital intervention comprises at least one physical intervention. As understood herein, a variety of physical interventions can be used for the digital intervention; the lists provided are examples of many of them, however, different combinations are used according to the aims and purposes of the intervention. Examples of physical interventions include, but are not limited to: physiotherapy, voice therapy, speech therapy, swallow therapy, breathing training, saliva and drooling therapy, chewing therapy, facial expression training, tremor management, mobility training, freezing and rigidity exercises, tapping training, limb agility exercises, volume-duration-pitch training, training for freezing of gait, motor function therapy, dance therapy, handwriting training, balance exercises, postural stability training, strength training, stretching exercises, coordination training, metronome training, fine motor skills training, or a combination thereof.

Metronome training refers to a therapeutic technique that utilizes rhythmic auditory stimulation to improve various cognitive or motor functions e.g., motor coordination, attention/concentration, timing/rhythm perception, anxiety/stress.

The maze interventions described herein are digital mazes. This includes digital mazes on a 2D screen, or virtual reality and/or augmented reality experiences. Examples of mazes are included, but are not limited to: Hebb-Williams maze, Morris water maze, Barnes maze, radial arm maze, T-maze and elevated plus maze. As used herein "digital maze" refers to any maze carried out at least partially in a digital format. Therefore, the examples provided of mazes such as Hebb-Williams maze are understood as at least partially digital implementations of these mazes. For example, the mazes can be navigated on a software application on a personal electronic device. It is noted that these digital mazes can be 'at least partially' implemented in a digital space since embodiments show that mazes that utilize augmented reality and virtual reality are at least partially implemented in physical, as well as digital, space.

As stated herein, and in various embodiments, the digital intervention comprises: sensory inhibition, sensory substitution, sensory integration, or a combination thereof. Any of the individual interventions described herein can comprise sensory inhibition, sensory substitution, sensory integration, or a combination thereof. As such, it is understood that when referring to a particular digital intervention the sensory principles apply. The "senses" referred to herein any of the following: visual, auditory, tactile, olfactory, and gustatory. In various embodiments, the senses refer to visual, auditory, and tactile. Examples of the sensory modalities and their corresponding inputs include: visual, auditory, tactile, gustatory, olfactory, proprioceptive and vestibular; all of which can be understood to be included in the sensory principles outlined in the present invention. "Senses" are also referred to "human sensory modality", "sensory modality" or "modality" and can be used and understood interchangeably. The 'inputs' and 'cues' that correspond to these sensory modalities are understood interchangeably. Furthermore, when referring to the various modalities, different expressions can be used to describe them. For example: an image can be described as a visual cue/stimulus/image, and auditory cues can be referred to as 'sounds'. An expert will understand that the use of these words are interchangeable according to the context in which they are referred to. In one embodiment "sensory inhibition" refers to the at least partial suppression of at least one human sensory modality input. Suppression refers to the implementation of where one modality is decreased or at least partially removed, e.g., covering one eye suppresses the visual capability of the individual; or lowering the volume of a melody reduces/suppresses the auditory input to the individual. In one embodiment the at least one human sensory modality input is selected from: visual, auditory, and tactile. As understood herein "sensory substitution" refers to the at least partial replacement of at least one human sensory modality input with at least one other human sensory modality input. For example, a person may be presented with a visual video clip with no audio after which the visual cues become more blurred and auditory cues replace the visual ones in a manner that is corresponding. One example is sounds directly related to the image e.g., the visible appearance of waves breaking on the coast and the sound of waves breaking on the coast. Training the individual with sensory substation leads to improvements in neuro-connectivity, in various embodiments. In one embodiment the at least partial replacement of at least one sensory modality input with at least one other sensory modality input is selected from:

visual to auditory and/or tactile;

auditory to visual and/or tactile; and tactile to visual and/or auditory.

The integration of more than one sensory modality input is achieved by combining sensory modality inputs. As understood herein, and in one embodiment, "integration" regarding the sensory modalities refers to the integration of the input of the modalities e.g., using visual cues and auditory cues together. In one embodiment sensory integration refers to the at least partial combination of at least two sensory modality inputs. In one embodiment the personal electronic device, the at least one additional device, or a combination thereof, are configured to provide sensory modality inputs to carry out the sensory inhibition, sensory substitution, sensory integration, or a combination thereof. In various embodiments the integration of the sensory modality inputs includes the following modalities: visual, auditory, and tactile. For example, a visual and auditory cue can be experienced together e.g., a particular sound (auditory) corresponding to a particular image (visual), and these can further be integrated with a vibration (tactile) sensation coupled with the auditory and visual cues such that the same event in time is experienced by the individual but with different modalities.

In one embodiment the digital intervention comprises the individual interacting with a personal electronic device using any of the following means selected from: touch gesture, motion gesture, voice commands, text input, camera and media interaction, sensor-based interactions, or a combination thereof. In one embodiment the at least one psychological intervention, at least one cognitive intervention, at least one physical intervention, or a combination thereof comprises the individual interacting with a personal electronic device using any of the following means selected from: touch gesture, motion gesture, voice commands, text input, camera and media interaction, sensor-based interactions, or a combination thereof. Examples of the touch gestures include, but are not limited to: tapping, swiping, scrolling, pinching, dragging, double-tapping, or a combination thereof. Examples of motion gestures include, but are not limited to: tilting, shaking, rotating, body motion, waving, or a combination thereof. Examples of camera and/or media interactions include, but are not limited to: taking photos, recording videos, uploading/downloading images, uploading/downloading audio, uploading/downloading video, augmented reality, or a combination thereof.

In various embodiments the sensor-based interactions are carried out by means of any of the following selected from: global positioning system (GPS) system, accelerometer, gyroscope, proximity sensor, or a combination thereof.

A variety of digital formats can be used to carry out the digital interventions of the invention. In one embodiment the at least one digital intervention is performed in any of the following formats: instructional video, interactive video comprising input and feedback from the individual, game, instructional prompts, question and answer survey with feedback, virtual reality, augmented reality, or a combination thereof.

The length of time that each intervention is carried out depends on the particular application, schedule, regimen, etc. of the individual. The following embodiments regarding the duration of the digital interventions apply for all digital interventions mentioned herein, and for any purpose, as mentioned herein. In one embodiment the at least one psychological intervention, at least one cognitive intervention, at least one physical intervention, or a combination thereof, spans a duration ranging from 1 second to 60 minute. In one embodiment the at least one psychological intervention, at least one cognitive intervention, at least one physical intervention, or a combination thereof, spans a duration ranging from 1 second to 30 minutes. In one embodiment the at least one psychological intervention, at least one cognitive intervention, at least one physical intervention, or a combination thereof, spans a duration ranging from 1 second to 10 minutes. In one embodiment the at least one psychological intervention, at least one cognitive intervention, at least one physical intervention, or a combination thereof, spans a duration ranging from 1 second to 5 minutes. In one embodiment the at least one psychological intervention, at least one cognitive intervention, at least one physical intervention, or a combination thereof, spans a duration ranging from 1 second to 1 minute. In one embodiment the at least one psychological intervention, at least one cognitive intervention, at least one physical intervention, or a combination thereof, spans a duration ranging from 1 minute to 5 minutes. In one embodiment the at least one psychological intervention, at least one cognitive intervention, at least one physical intervention, or a combination thereof, spans a duration ranging from 5 minutes to 10 minutes. In one embodiment the at least one psychological intervention, at least one cognitive intervention, at least one physical intervention, or a combination thereof, spans a duration ranging from 10 minutes to 30 minutes. In one embodiment the at least one psychological intervention, at least one cognitive intervention, at least one physical intervention, or a combination thereof, spans a duration ranging from 30 minutes to 60 minutes.

The embodiments delineating the duration of the digital therapy intervention plan applies for all digital therapy intervention plans disclosed herein, for any of the stated purposes e.g., to improve neuro-connectivity, improve immune function, etc. In some embodiments the digital therapy intervention plan is carried out over the course of between 1 day to 10 years. In some embodiments the digital therapy intervention plan is carried out over the course of between 1 day to 5 years. In some embodiments the digital therapy intervention plan is carried out over the course of between 1 day to 1 years. In some embodiments the digital therapy intervention plan is carried out over the course of between 1 day to 6 months. In some embodiments the digital therapy intervention plan is carried out over the course of between 1 day to 3 months. In some embodiments the digital therapy intervention plan is carried out over the course of between 1 day to 2 months. In some embodiments the digital therapy intervention plan is carried out over the course of between 1 day to 1 month. In some embodiments the digital therapy intervention plan is carried out over the course of between 1 day to 3 weeks. In some embodiments the digital therapy intervention plan is carried out over the course of between 1 day to 1 week.

The digital intervention plan requires personalization, tailored to the individual carrying out the plan. As such, the methods of the invention comprise an adaptation plan built into the digital intervention plan. The adaptation plan applies to all digital intervention plans disclosed herein, for any of the stated purposes e.g., improving neuro-connectivity, improving immune, etc. In one embodiment the methods of the invention further comprise an adaptation plan, during the course of the digital therapy intervention plan, comprising:

receiving the data;

receiving updated data in response to the at least one psychological intervention, the at least one cognitive intervention, the at least one physical intervention, or a combination thereof;

analyzing the data and the updated data by means of machine learning, artificial intelligence (AI), or statistical modeling; and generating an updated digital therapy intervention plan for the individual in response to the analyzing of the updated data.

Therefore, all of the data gathered at any point during the course of the digital intervention plan is stored and analyzed to provide personalization to the individual.

In one embodiment the adaptation comprises a change in any of the following selected from: type of intervention, intervention sequence, frequency of intervention, intensity of intervention, length of intervention, difficulty of intervention, sensory modality inputs used, level of interaction, or a combination thereof. For example, if an individual completes tasks relatively quickly, a particular intervention can be adapted to be more intense, longer, more difficult, etc. Or, if an individual provides feedback that they are overwhelmed by the amount of time spent carrying out the digital intervention sessions or the digital intervention plan itself, then intervention plan can adapt such that fewer sessions are carried out over a period of time. Another examples is that when an individual finds one particular session boring and/or uninteresting (and yet it is an important element in the individual's intervention plan), it may be scheduled for a different time of the day, or that particular intervention is carried out less frequently, or for less time. For example, the adaptation can include a change in any of the sensory modality inputs used, separately, or in combination.

As well as the digital intervention plan itself, a number of external devices can be used together with the methods of the invention to further advance the goals of providing digital therapy interventions (and their associated plans) for an individual. The additional devices utilized for the digital therapy intervention plan applies to any of the digital therapy intervention plans, and for any stated purpose e.g., increasing neuro-connectivity, improving immune, improving motor skills, etc. In one embodiment the methods of the invention further comprise at least one additional device selected from: health monitoring system, medical device, haptic device, external speakers, headphones, virtual reality set, augmented reality glasses/devices, biofeedback sensors, wearable activity trackers, smartphone, personal computational device, smart speakers, voice assistants, motion tracking sensor, virtual assistant systems, internet hub, or a combination thereof. In one embodiment the at least one additional device is configured to transfer data between the individual, the personal electronic device, or a combination thereof. Examples of health monitoring systems include, but are not limited to: wearable fitness trackers, remote patient monitoring (RPM) systems, telemedicine platforms, smart health devices, health and wellness apps and hospital information systems (HIS).

These additional devices are configured to provide at least one of: real-time feedback to the individual based on gathered data and interaction, measuring a health parameter, output a signal to the individual, customize the digital therapy intervention plan in real time, monitor the individual's engagement and adherence to therapy protocols, provide remote monitoring, cross-device cloud syncing and data sharing, or a combination thereof. Providing real-time feedback can include interactions with any of the digital platforms and digital therapy intervention sessions e.g., a questionnaire in the middle of a series of interventions.

In one embodiment, the personal electronic device, at least one additional device, or a combination thereof, are configured to provide the sensory modality inputs.

Although the digital interventions of the invention provide methods of treating, preventing, or alleviating symptoms in an individual affected by various diseases, the methods can also be utilized by someone who is otherwise not affected by these diseases. For example, a person who aims at increasing his/her general wellbeing by improving neuro-logical function. Furthermore, any of the digital therapy interventions, and their corresponding aims (e.g., increasing neuro-connectivity, improving immune function, etc.) can be understood as used to either treat, prevent, alleviate symptoms, or a combination thereof. Therefore "treat, prevent, alleviate symptoms" can be understood as doing each of them separately, or in combination, in various embodiments. Since the methods of the present invention are effective in any of those areas, their capability to treat/prevent/alleviate symptoms, are often considered together.

In one embodiment the invention provides a method for increasing neuro-connectivity, for treating, preventing, or alleviating symptoms in an individual affected by a neuro-degenerative disease. Examples of neuro-degenerative diseases include, but are not limited to: Alzheimer's disease, Parkinson's disease, multiple sclerosis (MS), amyotrophic lateral sclerosis (ALS), frontotemporal dementia, chronic traumatic encephalopathy (CTE), Lewy body dementia (LBD), progressive supranuclear palsy (PSP), multiple system atrophy (MSA), corticobasal degeneration (CBD), Huntington's disease, Creutzfeldt-Jakob disease, and Wilson's disease.

In one embodiment the invention provides a method for increasing neuro-connectivity, for treating, preventing, or alleviating symptoms in an individual affected by a neuro-logic disorder. Examples of neurologic disorders include, but are not limited to: Mild cognitive impairment (MCI), sleep disorders, migraine and headache disorders, neuropathies, epilepsy, traumatic brain injury, spinal cord injury, and cerebrovascular diseases.

In one embodiment the method for increasing neuro-connectivity is for treating, preventing, or alleviating symptoms in an individual affected by a psychological disorder. Examples of psychological disorders include, but are not limited to: depression, anxiety, bipolar disorder, obsessive-compulsive disorder (OCD), post-traumatic stress disorder (PTSD), attention-deficit/hyperactivity disorder (ADHD), eating disorders, substance use disorder, sleep disorders, autism spectrum disorder (ASD), personality disorders, schizophrenia, and dissociative disorders.

Combined Digital Therapy to Improve Neuro-Connectivity

The invention provides a combined therapy to improve neuro-connectivity comprising administering at least one digital therapy and carrying out at least one non-digital medical intervention. In one embodiment the combined therapy to improve neuro-connectivity comprises administering at least one digital therapy and at least one medicinal agent. The term "combined" (or "combined method") is used to describe any intervention that includes at least one digital therapy intervention and at least one non-digital therapy intervention. Thus, for any of the methods disclosed herein, the 'stand-alone' methods that utilize digital therapy interventions alone, are used to be comprised within 'combined' interventions, equally. Therefore, all the methods directed towards improving neuro-connectivity that utilize digital interventions alone, can be understood to be used in combination with the various non-digital interventions that are disclosed. The same applies for other methods that affect other biological processes e.g., improving immune function and improving motor function. One of the benefits of the present invention is in its combination with known drug therapies, to help improve outcomes.

In various embodiments, and as used herein, the terms "drug", "medication", "medicinal agent", "pharmaceutical", "medicine" or the likes are to be understood interchangeably. Namely, these refer to any substance used to diagnose, prevent, treat, or alleviate symptoms of a medical condition. They can also refer to substances that are generally aimed at maintaining or improving an individual's well-being without specifically targeting a disease. Thus, in various embodiments, the 'medicinal agent' can refer to a nutritional supplement, as will be detailed. As used herein, and in various embodiments, the "treatment" of any disease includes any intervention that alleviates symptoms or causes at least one marker of that disease to improve. Therefore, "treatment", as understood herein, also refers to delayed onset or prevention of a disease, in various embodiments.

In one embodiment the invention provides a method of increasing neuro-connectivity in an individual, the method comprising:

the individual carrying out at least one digital intervention comprising: sensory inhibition, sensory substitution, sensory integration, or a combination thereof; and administering at least one non-digital medical intervention before, during, after, or a combination thereof, said at least one digital intervention.

In some embodiment the non-digital medical intervention is selected from: medicinal agent, medical procedures, physiotherapy, psychotherapy, psychiatry, rehabilitation, lifestyle interventions, nutritional supplement, mineral supplement, and physical exercise.

As understood for 'combination' therapies, the administration of non-digital medical interventions is before at least one digital intervention, in one embodiment. In another embodiment, the administration of non-digital medical interventions is during at least one digital intervention. In another embodiment, the administration of non-digital medical interventions is after the at least one digital intervention. It has been stated that a digital intervention plan comprises a plurality of sessions and/or digital interventions, thus not every administration of non-digital medical intervention as part of a plan necessarily needs to be coupled with the same digital intervention for each combined therapy intervention. For example, in one digital therapy intervention plan, a particular drug is administered to an individual once a month; but each month, the digital intervention will not be necessarily the same e.g., during the first administration the individual may undergoes a psychological-based therapy for 5 mins, whereas upon the second administration the individual undergoes a cognitive-based therapy. The type of digital intervention, as coupled with the administration of the drug, can change each time the drug is administered. This applies equally to the particular dosage of the drug, the intensity/frequency/type of digital intervention, etc. As also disclosed, the combined therapy can be used as a means to condition the individual to improve functioning of the drug itself. Conditioning an individual in such a way can be carried out by positive re-enforcement by digital cues and interventions described herein. For example, concurrent administration of the medicinal agent alongside a digital therapy can modulate immune responses, improve motor function, improve neuro-connectivity/plasticity, improve treatment outcomes, or reduce treatment-associated toxicity. Administering the medicinal agent during digital therapy can also take the form of continuous infusion or periodic dosing of the medicinal agent during the course of a therapy to maintain an optimal function or target specific markers in real-time i.e., in response to carrying out digital therapy. The administration of medical agents can also occur after a digital therapy. Post-treatment administration of the medicinal agent can support immune recovery, reduce the risk of infection, or prevent disease recurrence following completion of a digital therapy. Administration of the medicinal agent as part of a maintenance regimen to sustain immune/neurological function or prolong treatment benefits after the conclusion of the digital therapy.

Another example of coupling digital therapy with medical interventions is coupling the administration together with a particular point along the patient journey, e.g., at the peak of a particular marker. Administering the medicinal agent can be timed to be carried out at the peak expression or activity of a specific marker (e.g., immune/neurological) to capitalize on heightened responsiveness or target pathological processes most effectively. Or timing the administration of the medicinal agent to coincide with the peak inflammatory response or immune activation associated with a particular marker to maximize therapeutic efficacy. Thus, the timing of the administration of any digital intervention, non-digital medical intervention, or a combination thereof, is considered within the scope of the present invention.

The administering of a digital intervention and/or medicinal agent can be done at various points in the treatment plan of an individual. For some medicinal agents the medicinal agent is administered before the therapy and/or treatment. Administering the medicinal agent prior to the initiation of a specific therapy to prime the immune system or enhance the effectiveness of subsequent treatments, is one such example. Pre-treatment with the medicinal agent to mitigate potential side effects or adverse reactions associated with the therapy, is another example.

A whole host of medicinal agents are available for improving neuro-connectivity in humans. Examples of medicinal agents include, but are not limited to: dopaminergic agent, anti-amyloid beta antibody, opioids, immune checkpoint inhibitors, NMDA receptor antagonist, triptans, acetylcholinesterase inhibitor, neuro-steroids, anti-inflammatory agents, neuroprotective agents, mitochondrial support agents, metabolic therapy, hormone therapy, Tau-targeted therapy, beta-secretase inhibitors, gamma-secretase modulators, or a combination thereof.

In one embodiment the dopaminergic agent is selected from: dopamine precursor, dopamine agonist, monoamine oxidase inhibitors (MAOIs), or a combination thereof. In one embodiment the dopamine precursor is selected from: levodopa, levodopa, levodopa-carbidopa, levodopa-benserazide, levodopa-cabidopa-entacapone and foslevodopa-foscarbidopa. In one embodiment the dopamine agonist is selected from: pramipexole, ropinirole, rotigotine, apomorphine, bromocriptine, cabergoline, pergolide, and lisuride. In one embodiment the monoamine oxidase inhibitors is selected from: selegiline, rasagiline, safinamide. In one embodiment the anti-amyloid beta antibody is selected from: lecabemab, aducanumab, solanezumab, gantenerumab, crenezumab, donanemab, or a combination thereof. In one embodiment the opioids are selected from: morphine, fentanyl, oxycodone, hydrocodone, buprenorphine, codeine, hydromorphone, meperidine, tapentadol, butorphanol, pethidine, levorphanol, methadone, dextropropoxyphene, tramadol, ketobemidone, or a combination thereof. In one embodiment the PD-1 inhibitors, pembrolizumab, nivolumab, cemiplimab, PD-L1 inhibitors, avelumab, atezolizumab, durvalumab, CTLA-4 inhibitors, ipilimumab, tremelimumab, LAG-3 inhibitors, relatlimab, TIM-3 inhibitors, sabatolimab, TIGIT inhibitors, tiragolumab, domvanalimab, CD40 agonists, selicrelumab, OX40 agonists, utomilumab, GITR agonists, tiragolumab, IDO1 inhibitors, VISTA inhibitors, B7-H3 inhibitors, or a combination thereof. In one embodiment the NMDA receptor antagonist is selected from: SAGE-718, memantine, dextromethorphan (DXM), phencyclidine (PCP), methoxetamine (MXE), and nitrous oxide ($N_2O$), ketamine, or a combination thereof. In one embodiment the acetylcholinesterase inhibitor is selected from: donepezil, rivastigmine, galantamine, or a combination thereof. In one embodiment the neuro-steroids are selected from: allopregnanolone, dehydroepiandrosterone, pregnenolone, progesterone, androstenediol, estradiol, testosterone, or a combination thereof. In one embodiment the anti-inflammatory agent is selected from: nonsteroidal anti-inflammatory drugs (NSAIDs), corticosteroids, biologic drugs, or a combination thereof. In one embodiment the anti-inflammatory agent is selected from: ibuprofen, naproxen, aspirin, celecoxib, diclofenac, prednisone, hydrocortisone, dexamethasone, prednisolone, methylprednisolone, tumor necrosis factor (TNF) inhibitors, interleukin (IL) inhibitors, Janus Kinase (JAK) inhibitors, interleukin-1 (IL-1) receptor antagonists, interleukin-6 (IL-6) inhibitors, interleukin-17 (IL-17) inhibitors, biologic disease-modifying antirheumatic drugs (DMARDs), colchicine, or a combination thereof. In one embodiment the neuroprotective agent is selected from: allopregnanolone, dehydroepiandrosterone, pregnenolone, progesterone, androstenediol, estradiol, testosterone, ketamine, riluzole, antioxidants, vitamin e, vitamin c, alpha-lipoic acid, omega-3 fatty acids, coenzyme q10 (CoQ10), *Ginkgo biloba* extract, melatonin, resveratrol, nerve growth factor (NGF), brain-derived neurotrophic factor (BDNF), glutathione, magnesium, 1-carnitine, carnosine, n-acetylcysteine (NAC), curcumin, quercetin, green tea extract, bacopa monnieri, ginseng, huperzine A, or a combination thereof. In one embodiment the nutritional supplement is selected from: vitamin B, vitamin B12, omega-3 fatty acids, magnesium, zinc, iron, folate, vitamin c, vitamin e, probiotics, *Ginkgo biloba*, curcumin, coenzyme q10, acetyl-l-carnitine, alpha-lipoic acid, phosphatidylserine, bacopa monnieri, ashwagandha, *Rhodiola rosea*, l-theanine, melatonin, or a combination thereof.

In one embodiment the medicinal agent is administered by: injection, orally, topically, inhalation, transdermal, intranasal, intravenous, intramuscular, subcutaneous, or a combination thereof.

In one embodiment the combined method for improving neuro-connectivity is further configured such that said digital therapy intervention plan is configured to account for said individual's medicinal intake, dosage regimen and non-digital medical intervention schedule, to achieve said increase in neuro-connectivity. In one embodiment the medicinal agent is administered together with a conditioning stimulus selected from: visual, auditory, tactile, or a combination thereof. Other examples of conditioning stimuli include, but are not limited to: smell and taste.

Digital Therapy to Improve Immune Function

It is noted that the terms used for methods of digital therapies are used consistently throughout apply to any of the digital therapies and their related interventions. In one embodiment the method is for treating, preventing, or alleviating symptoms in an individual affected by Parkinson's disease, Alzheimer's disease, or mild cognitive impairment (MCI).

The present invention provides a method for improving immune function in an individual. As used herein, "immune function" refers to the body's defense mechanisms against pathogens. Pathogens can include: bacteria, viruses, fungi, protozoa, parasites, prions, etc. Thus, improved immune function can refer to a whole host of markers that improve as a result of carrying out the methods of the present invention. Biological markers that indicate an improving immune function are selected from any of the following, but not limited to: white blood cell count, cytokines, antibody types, antibody levels, complement proteins, inflammatory markers, T cells, natural killer (NK) cell activity, phagocytic activity, etc. Thus "improving immune function" is defined as improving, or modulating, even partially, any of the markers associated with improving the immune system.

In one embodiment the invention provides a method for improving immune function in an individual, the method comprising:

the individual carrying out at least one digital intervention comprising: sensory inhibition, sensory substitution, sensory integration, or a combination thereof.

In one embodiment the invention provides a method for increasing neuro-connectivity in an individual, the method comprising:

the individual carrying out a digital therapy intervention plan comprising at least one digital intervention comprising: sensory inhibition, sensory substitution, sensory integration, or a combination thereof.

In one embodiment the at least one digital intervention is comprised within a digital therapy intervention plan. In one embodiment the method for improving immune function comprises a digital intervention comprising: at least one psychological intervention, at least one cognitive intervention, at least one physical intervention, or a combination thereof. Examples of psychological, cognitive and physical interventions are already provided herein. In one embodiment the at least one psychological intervention, the at least one cognitive intervention, the at least one physical intervention, or a combination thereof, spans a duration ranging from 1 second to 60 minutes. Other embodiments for the duration are already provided herein. Furthermore, embodiments regarding the length of the course have already been provided herein e.g., 1 day to 10 years.

In one embodiment the invention provides a method for improving immune function in an individual, the method comprising: carrying out at least one digital intervention comprising sensory inhibition. In one embodiment the invention provides a method for improving immune function in an individual, the method comprising: carrying out at least one digital intervention comprising sensory substitution. In one embodiment the invention provides a method for improving immune function in an individual, the method comprising: carrying out at least one digital intervention comprising sensory integration. As understood herein, sensory inhibition, substitution and integration can be used separately or in any combination, for carrying out digital interventions. Personalization of an individual's digital therapy intervention plan will be tailored to the individual person, although general guiding principles can be used to design an intervention plan. As will be described, digital intervention plans can be generally utilized using the three principles of sensory inhibition, substitution and integration, via a plurality of digital interventions; some being based on cognitive interventions, psychological interventions, or combinations thereof.

In one embodiment the method for improving immune function further comprises an adaptation plan, during the course of the digital therapy intervention plan, comprising:
receiving any of the data disclosed herein;
receiving updated data in response to the at least one psychological intervention, the at least one cognitive intervention, the at least one physical intervention, or a combination thereof;
analyzing the data and the updated data by means of machine learning, artificial intelligence (AI), or statistical modeling; and
generating an updated digital therapy intervention plan for the individual in response to the analyzing of the updated data.

The types of adaptations have been disclosed herein e.g., type of intervention, intervention sequence, frequency of intervention, intensity of intervention, length of intervention, difficulty of intervention, sensory modality input used, level of interaction, or a combination thereof.

In one embodiment the method of improving immune function in an individual comprises at least one cognitive intervention. In one embodiment the method of increasing improving immune function in an individual comprises at least one psychological intervention. In one embodiment the digital intervention comprises at least one cognitive intervention and at least one psychological intervention. In one embodiment the digital intervention comprises at least one cognitive intervention, at least one psychological intervention, at least one physical intervention, or a combination thereof.

Although the digital interventions of the invention provide methods of treating, preventing, or alleviating symptoms in an individual affected by various diseases, the methods can also be utilized by someone who is otherwise not affected by these diseases. For example, a person who aims at increasing his/her general wellbeing by improving immune function. Maintenance of a strong immune provides a good basis for maintaining an individual's health and wellbeing for longer periods of time. Therefore, the methods are used as a preventative measure as well as ones to treat and/or alleviate symptoms.

In one embodiment the invention provides a method for treating, preventing, or alleviating symptoms in an individual affected by an immune-related disorder. General categorization of immune-related disorders are: autoimmune disorder and immunodeficiency disorder. Examples of autoimmune disorder include, but are not limited to: alopecia areata, autoimmune angioedema, autoimmune progesterone dermatitis, autoimmune urticaria, bullous pemphigoid, cicatricial pemphigoid, dermatitis herpetiformis, dermatomyositis, discoid lupus erythematosus, epidermolysis bullosa acquisita, gestational pemphigoid, hidradenitis suppurativa, lichen planus, lichen sclerosus, linear IgA disease, morphea, psoriasis, pemphigus vulgaris, scleroderma (systemic sclerosis), vitiligo, autoimmune enteropathy, autoimmune hepatitis, celiac disease, Crohn's disease, pernicious anemia, ulcerative colitis, rheumatoid arthritis, systemic lupus erythematosus, rheumatic heart disease, Kawasaki disease, giant cell arteritis, Takayasu's arteritis, Behçet's disease, eosinophilic granulomatosis with polyangiitis (EGPA), granulomatosis with polyangiitis (GPA), IgA vasculitis (IgAV), leukocytoclastic vasculitis, lupus vasculitis, rheumatoid vasculitis, microscopic polyangiitis (MPA), polyarteritis nodosa (PAN), polymyalgia rheumatica, urticarial vasculitis, vasculitis, Goodpasture syndrome, IgA nephropathy, membranous nephropathy, lupus nephritis, primary sclerosing cholangitis, acute disseminated encephalomyelitis, acute motor axonal neuropathy, anti-NMDA receptor encephalitis, autoimmune encephalitis, Balo concentric sclerosis, Bickerstaffs encephalitis, chronic inflammatory demyelinating polyneuropathy, Guillain-Barré syndrome, Hashimoto's encephalopathy, idiopathic inflammatory demyelinating diseases, Lambert-Eaton myasthenic syndrome, multiple sclerosis, myasthenia gravis, neuromyelitis optica (devic's disease)/NMOSD, stiff-person syndrome, Sydenham's chorea, undifferentiated connective tissue disease (UCTD), Addison's disease, autoimmune oophoritis, autoimmune orchitis, autoimmune pancreatitis, autoimmune polyendocrine syndrome type 1 (APS1), autoimmune polyendocrine syndrome type 2 (APS2), autoimmune polyendocrine syndrome type 3 (APS3), diabetes mellitus type 1, graves' disease, hashimoto's thyroiditis, ord's thyroiditis, sjögren syndrome, rheumatoid lung disease, sarcoidosis, autoimmune hemolytic anemia, immune thrombocytopenia, thrombotic thrombocytopenic purpura, antiphospholipid syndrome, paroxysmal nocturnal hemoglobinuria, autoimmune retinopathy, autoimmune uveitis, cogan syndrome, graves' ophthalmopathy, mooren's ulcer, opsoclonus myoclonus syndrome, optic neuritis, susac's syndrome, sympathetic ophthalmia, inclusion body myositis, myositis, autoimmune neuromyotonia, paraneoplastic cerebellar degeneration, and polymyositis.

Examples of immunodeficiency disorder include, but are not limited to: severe combined immunodeficiency (SCID), DiGeorge syndrome, hyperimmunoglobulin E syndrome (Job's syndrome), common variable immunodeficiency (CVID), chronic granulomatous disease (CGD), Wiskott-Aldrich syndrome (WAS), autoimmune lymphoproliferative syndrome (ALPS), hyper IgM syndrome, leukocyte adhesion deficiency (LAD), NF-κB essential modifier (NEMO) mutations, selective immunoglobulin A deficiency, X-linked agammaglobulinemia (XLA), X-linked lymphoproliferative disease (XLP), and ataxia-telangiectasia.

Combined Digital Therapy to Improve Immune Function

The invention provides a combined therapy to improve immune function comprising administering at least one digital therapy and carrying out at least one non-digital medical intervention. In one embodiment the combined therapy to improve immune function comprises administering at least one digital therapy and at least one medicinal agent. As stated above, the term "combined" (or "combined method") is used to describe any intervention that includes at least one digital therapy intervention and at least one non-digital therapy intervention. Thus, for any of the methods disclosed herein, the 'stand-alone' methods that utilize digital therapy interventions alone, are used to be comprised within 'combined' interventions, equally. Therefore, all the methods directed towards improving immune function that utilize digital interventions alone, can be understood to be used in combination with the various non-digital interventions that are disclosed. One of the benefits of the present invention is in its combination with known drug therapies, to help improve outcomes. In one embodiment the combined method is for treating, preventing, or alleviating symptoms in an individual affected by Parkinson's disease, Alzheimer's disease, or mild cognitive impairment (MCI).

In one embodiment the invention provides a method for improving immune function in an individual, the method comprising:

the individual carrying out at least one digital intervention comprising: sensory inhibition, sensory substitution, sensory integration, or a combination thereof; and administering at least one non-digital medical intervention before, during, after, or a combination thereof, said at least one digital intervention.

In one embodiment the combined method for improving immune function is for treating, preventing, or alleviating symptoms in an individual affected by an immune-related disorder. The immune-related disorders are disclosed hereinabove.

In various embodiments the at least one non-digital medical intervention for the combined method for improving immune function, is selected from: medicinal agent, medical procedures, physiotherapy, psychotherapy, psychiatry, rehabilitation, lifestyle interventions, nutritional supplement, mineral supplement, and physical exercise.

In one embodiment the medicinal agent is selected from: immunosuppressants, biologic immune therapies, psychedelic drug, and immune checkpoint inhibitors. In one embodiment the immunosuppressants are selected from: steroids, colchicine, hydroxychloroquine, sulfasalazine, dapsone, methotrexate, mycophenolate mofetil, azathioprine, cyclosporine, or a combination thereof. Examples of psychedelic drugs include, but are not limited to: LSD (Lysergic acid diethylamide), Psilocybin (Magic mushrooms), MDMA (Ecstasy or Molly), DMT (Dimethyltryptamine), Peyote, Ayahuasca, Ketamine, Mescaline, PCP (Phencyclidine), *Salvia divinorum*, etc.

In one embodiment the biologic immune therapies are selected from: anakinra, canakinumab, rilonacept, infliximab, adalimumab, golimumab, Etanercept, Certolizumab, tocilizumab, sarilumab, eculizumab, rituximab, belimumab, abatacept, secukinumab, ixekizumab, brodalumab, guselkumab, ustekinumab, dupixent, vedolizumab, tofacitinib, upadacitinib, baricitinib, mepolizumab, reslizumab, benralizumab, or a combination thereof.

In one embodiment the immune checkpoint inhibitors are selected from: PD-1 inhibitors, PD-L1 inhibitors, CTLA-4 inhibitors, LAG-3 inhibitors, TIM-3, TIGIT inhibitors, CD40 agonists, OX40 agonists, GITR agonists, IDO1 inhibitors, VISTA inhibitors, B7-H3 inhibitors, or a combination thereof. Examples of PD-1 inhibitors include, but are not limited to: pembrolizumab, nivolumab and cemiplimab. Examples of PD-L1 inhibitors include but are not limited to: avelumab, atezolizumab and durvalumab. Examples of CTLA-4 inhibitors include, but are not limited to: ipilimumab and tremelimumab. A non-exhaustive example of LAG-3 inhibitors is relatlimab. A non-exhaustive example of TIM-3 inhibitors is sabatolimab. Examples of TIGIT inhibitors includes, but is not limited to: tiragolumab and domvanalimab. A non-exhaustive example of CD40 agonists is selicrelumab. A non-exhaustive example of OX40 agonists is utomilumab. A non-exhaustive example of a GITR agonists is tiragolumab.

In one embodiment the immune checkpoint inhibitors are selected from: PD-1 inhibitors, pembrolizumab, nivolumab, cemiplimab, PD-L1 inhibitors, avelumab, atezolizumab, durvalumab, CTLA-4 inhibitors, ipilimumab, tremelimumab, LAG-3 inhibitors, relatlimab, TIM-3 inhibitors, sabatolimab, TIGIT inhibitors, tiragolumab, domvanalimab, CD40 agonists, selicrelumab, OX40 agonists, utomilumab, GITR agonists, tiragolumab, IDO1 inhibitors, VISTA inhibitors, B7-H3 inhibitors, or a combination thereof.

In one embodiment the combined method is further configured such that the digital therapy intervention plan accounts for said individual's medicinal intake, dosage regimen and non-digital medical intervention schedule, to achieve said improved immune function.

Digital Therapy to Improve Motor Skills

The invention provides digital-based therapies to improve motor skills. Generally, "motor skills" refer to the ability to perform physical movements e.g., manipulate objects with precision and coordination. These skills involve the integration of sensory information, muscle control, and cognitive processes to execute specific actions effectively. Motor skills can be broadly categorized into two main types: gross motor skills, and fine motor skills. Due to the physical nature of motor skills, the associated interventions are often referred to as "physical interventions". As will be shown, the principles of sensory inhibition, substitution and, integration, apply to improving motor skills, in a similar manner that they have to increasing neuro-connectivity and improving immune function.

Thus "improving" with regards to motor skills refers to even a minimal improvement, or modulation, of at least one gross motor skill, at least one fine motor skill, or a combination thereof. The terms "improving" and "increasing" motor skills are used interchangeably. Typically, gross motor skills involve the use of large muscle groups to perform activities such as walking, running, jumping, and throwing. These skills are essential for activities that require strength, balance, and coordination of the entire body. Fine motor skills involve the use of smaller muscle groups, particularly those in the hands and fingers, to perform tasks that require dexterity, precision, and hand-eye coordination. Examples of fine motor skills include writing, drawing, tying shoelaces, and using utensils.

In one embodiment the invention provides a method of improving motor skills in an individual on a digital platform. In one embodiment the method comprises:

the individual carrying out at least one digital intervention comprising a physical intervention based on: sensory inhibition, sensory substitution, sensory integration, or a combination thereof.

In one embodiment the at least one digital intervention is comprised within a digital therapy intervention plan. In one embodiment the at least one digital intervention is at least partially carried out on a personal electronic device.

In one embodiment the at least one physical interventions is selected from: physiotherapy, voice therapy, speech therapy, swallow therapy, breathing training, saliva and drooling therapy, chewing therapy, facial expression training, tremor management, mobility training, freezing and rigidity exercises, tapping training, limb agility exercises, volume-duration-pitch training, training for freezing of gait, motor function therapy, dance therapy, handwriting training, balance exercises, postural stability training, strength training, stretching exercises, coordination training, metronome training, fine motor skills training, or a combination thereof.

All of the physical interventions utilize any of the following: sensory inhibition, sensory substitution, sensory integration, or a combination thereof, on a digital platform. Thus, the sensory principles utilized for other purposes are used for physical interventions in an equivalent manner. For example, voice therapy utilizes proprioception which refers to the sense of body position and movement. Proprioceptive feedback is used to control the muscles involved in vocal production, such as the vocal cords, diaphragm, and mouth, to produce specific pitches and modulate the quality of their voice. Thus, auditory (voice) and tactile (proprioception) are two senses used together for voice therapy and training. The sensory principles employed for other methods of the invention can be used equivalently for the purpose of improving motor skills.

In various embodiments, voice therapy includes digital versions of speech therapy techniques for patients that suffer from speech-related problems, as a result of a medical condition e.g., Parkinson's disease. As used herein, "voice therapy" also refers to "voice exercises".

The voice exercises utilize the principles of sensory integration, deprivation and substitution. In one embodiment voice therapy comprises amplitude training. In amplitude training the patient's volume is emphasized, as in some medical conditions the voice becomes softer and weaker. Initially a personal electronic device detects the normal and maximum volumes produced by the patient, and establishes the practice volume starting point. The patient is then asked to say a specific syllable ("Aha", "Bha", "Boo", etc.), word or phrase, and is asked to maintain a certain volume for an amount of time while the digital platform (e.g., an app, a software application) provides real time feedback on how close the detected volume is to the required volume. Regarding personalization the volume level and duration requested are based on the initial levels recorded as well as can increase/decrease based on the patient's performance, asking the patient to maintain a higher volume for a longer period of time as they progress in the exercise, within a specific session and also across sessions continuously. While speaking, the app provides a feedback as:

A visual meter that indicates the required volume and when the patient is speaking above or below it;

A visual animation signifying going up or down (e.g. a ski lift);

An auditory feedback for reaching the desired volume and time;

A haptic feedback for reaching the desired volume and time.

In addition the application may offer the patient to record themselves and then playback the recording for additional feedback. Various embodiments of voice therapy are implemented such that the exercises are built in a transition from visual feedback along with auditory and/or haptic feedback, to auditory and/or haptic feedback only (depriving the visual feedback) i.e., using the sensory principles. In a corresponding manner, amplitude and pitch can be used for voice therapy i.e., by addition of a voice pitch aspect.

In one embodiment voice exercises comprises reading training. Reading training is similar to the amplitude exercise, however the patient is asked to read words, sentences and/or paragraphs. The digital therapy system focuses on measures of volume, modulation and clarity, in various embodiments. In one embodiment of reading training, the patient is asked to read a list of words, and then is asked to recall them. In one embodiment the patient is asked to read a list of words, and then is asked to recall them while in blindfold. In one embodiment the word is not shown on the screen but is played, and the patient is blindfolded also during the introduction of the word/sentence.

In one embodiment the voice therapy comprises speaking training. Speaking training is carried out in a similar manner to the amplitude exercise, however the patient is prompted with a cue and is asked to respond in speech. Cues can include: portions of conversation (e.g., "hi, how are you today?"), sentence completions (e.g., "what I love most about weekends is . . . "), questions about experiences (e.g., "tell me about one good moment you experienced last week") or informational questions (e.g., "tell me the 4 directions on a map"). Furthermore, the terms "input" and "cue" can be understood interchangeably in terms of the sensory modalities. For example, when a sensory modality input or cue is provided by the personal electronic device.

As understood herein, and in one embodiment, "suppression" of a modality refers to the suppression of the input of the modality. Regarding improving motor skills, sensory inhibition comprises the at least partial reduction of at least one sensory modality input. In one embodiment, the at least one sensory modality input is selected from: visual, auditory, and tactile. As understood herein, and in one embodiment, "replacement" regarding sensory modalities refers to the replacement of the input of the modality e.g., replacing a visual with an auditory cue. In one embodiment the sensory substitution comprises the at least partial replacement of at least one sensory modality input with at least one other sensory modality input. In one embodiment the at least partial replacement of at least one sensory modality input with at least one other sensory modality is selected from:

visual to auditory and/or tactile;

auditory to visual and/or tactile; and tactile to visual and/or auditory.

Regarding improving motor skills, sensory integration comprises the at least partial combination of at least two sensory modality inputs. In one embodiment the at least two sensory modalities are selected from: visual, auditory, and tactile. In one embodiment the at least one digital intervention comprises the individual interacting with the personal electronic device using any of the following means selected from: touch gesture, motion gesture, voice commands, text input, camera and media interaction, sensor-based interactions, or a combination thereof. The details of these means are provided hereinabove.

Regarding improving motor skills, the at least one digital intervention is performed in any of the following formats: instructional video, interactive video comprising input and feedback from the individual, game, instructional prompts, question and answer survey with feedback, virtual reality, augmented reality, or a combination thereof. The details of these formats are provided hereinabove.

In one embodiment the methods of improving motor skills is used for treating, preventing, or alleviating symptoms in an individual affected by a movement disorder. In one embodiment the methods of improving motor skills is used for treating, preventing, or alleviating symptoms in an individual affected by a movement disorder.

Examples of movement disorders include, but are not limited to: motor disorder is selected from: Parkinsonism, ataxia, dystonia, tremor, chorea, tics, spasticity, gait disorders, multiple system atrophy (MSA), progressive supranuclear palsy (PSP), Lewy body dementia (LBD), corticobasal degeneration, Huntington's disease, Friedreich's ataxia, essential tremor, myoclonus, Tourette syndrome, restless leg syndrome, tardive dyskinesia, and Wilson's disease.

Digital Mazes of the Invention

The "digital mazes" of the present invention relate to mazes at least partially carried out in a digital format. They are primarily used for digital therapy interventions and utilize the 'sensory principles'. Namely, carrying out a digital intervention comprising: sensory inhibition, sensory substitution, sensory integration, or a combination thereof. The digital mazes are therefore typically carried out on a system, which includes a software application. Such a system comprises a personal electronic device, but can also include any number of additional devices, as will be explained.

FIGS. 1A-1B and FIGS. 2A-2D show some examples of the digital mazes of the invention. FIG. 1A shows a screen show on a mobile phone application; the user is positioned such that he can view the floor, walls, and paintings on the wall. FIG. 1B shows a different digital maze where the exit point (otherwise referred to as 'finishing point') is in view. Paintings on the wall can be used for 'recall' exercises once the user has completed the digital maze. Such items placed within the digital maze can be used for memory exercises.

Figure 2B:
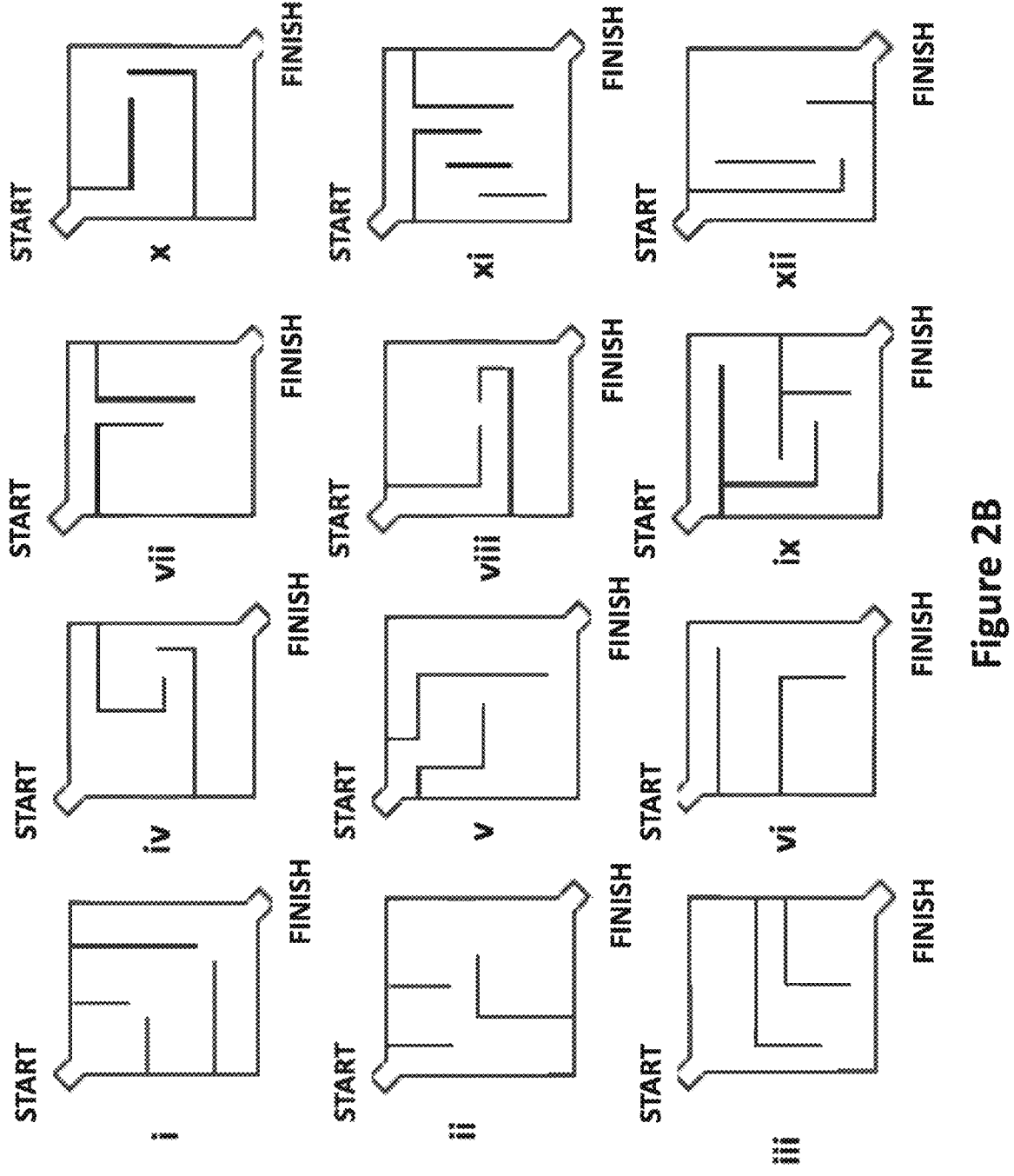

FIG. 2A shows a birds eye view of six mazes of varying complexity. The user needs to navigate around obstacles (in this case 'walls' and 'dead ends') to navigate from start to finish. FIG. 2B shows further complexity in a series of digital mazes. Some of the digital mazes can be completed by the user along different paths. In various embodiments, the user must find the quickest path to the exit.

Figure 2C:
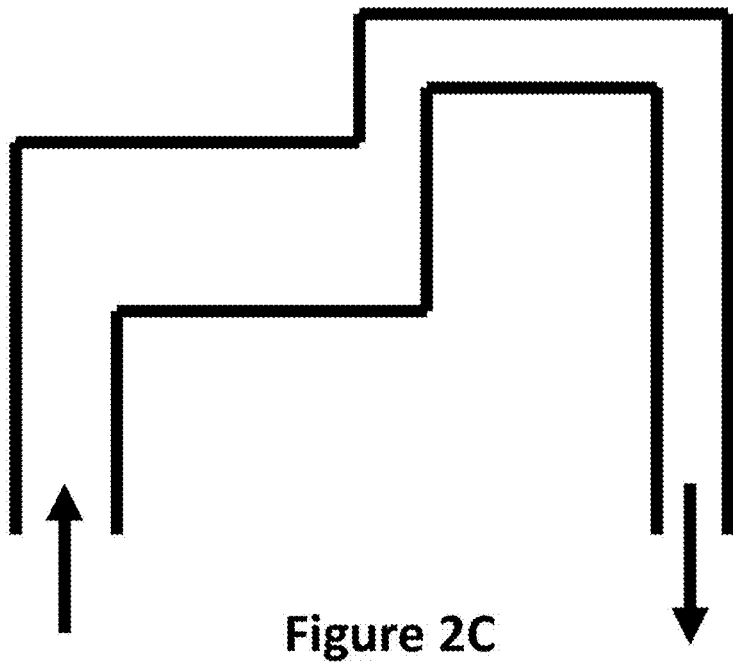
Figure 2D:
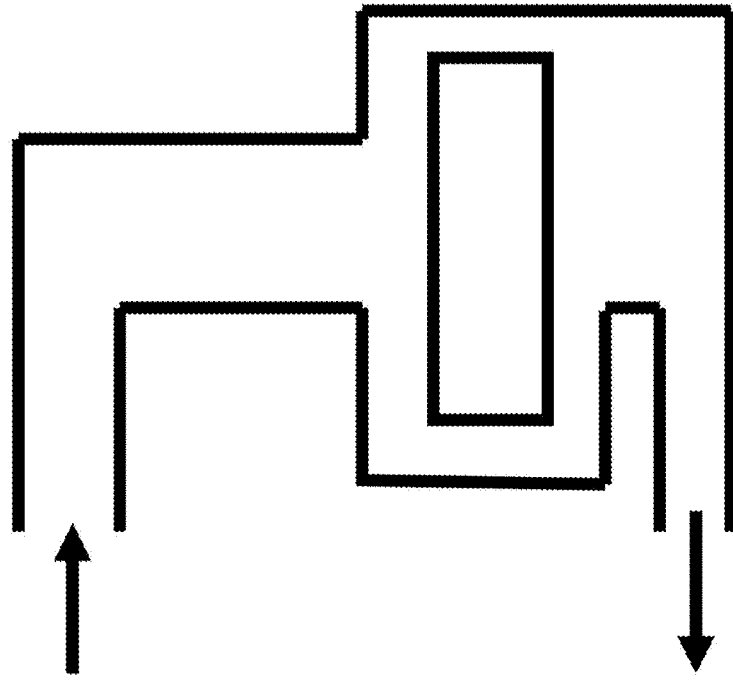

FIG. 2C and FIG. 2D show different mazes along which a user must navigate from start to finish. Namely, the digital maze can be any structure. The digital maze can also be a 3D structure, such as one that incorporates stairs that requires the user to move from one floor to another. FIG. 2C shows a corridor with several turns, where the corridor width changes along the path to the finish. FIG. 2D shows another digital maze with several paths along which the user can move from start to finish. FIG. 2D shows a rectangular obstacle placed in the middle of the digital maze.

Figure 18A:
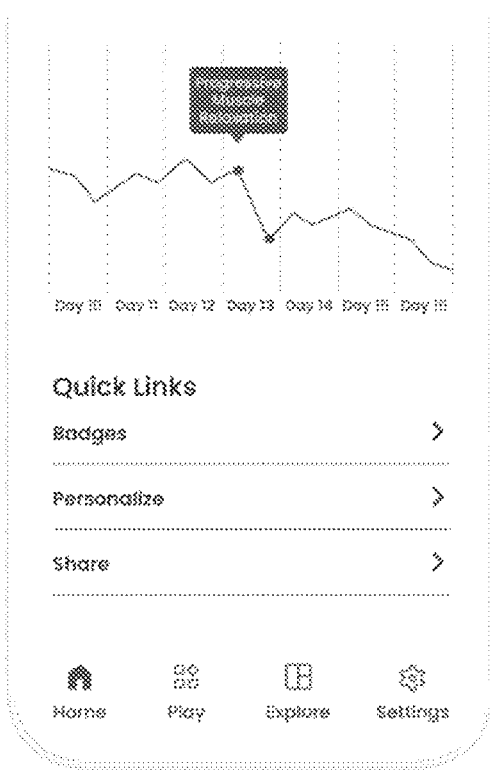
Figure 18B:
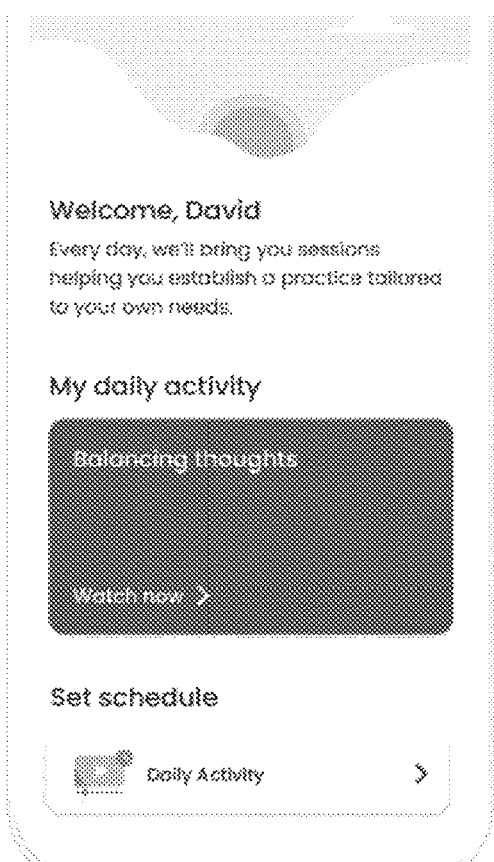
Figure 18C:
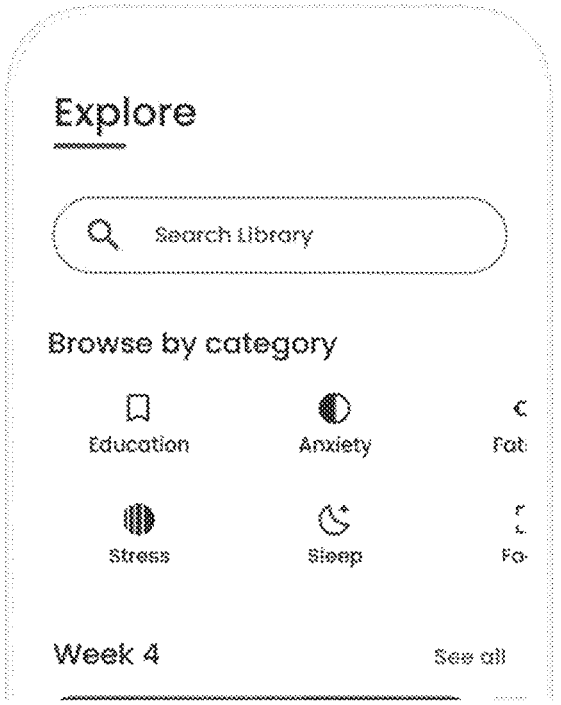
Figure 18D:
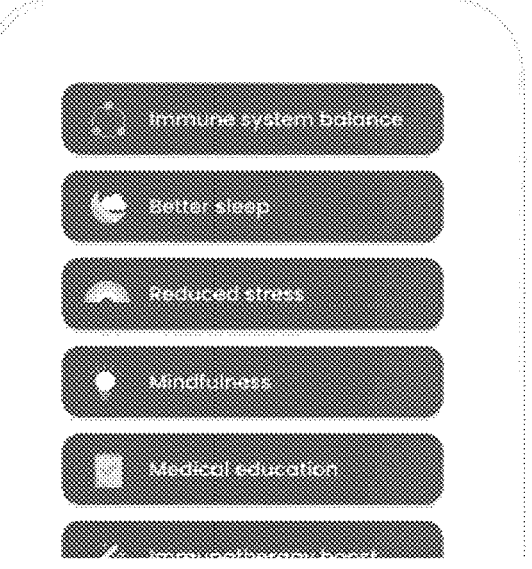
Figure 18E:
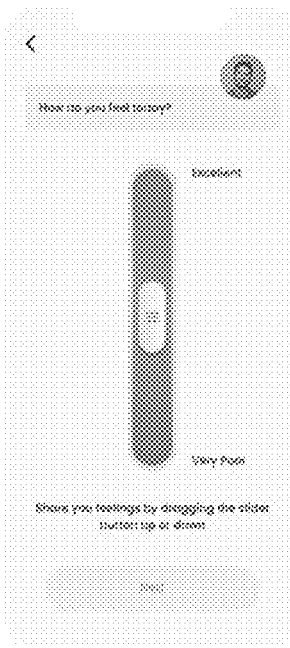
Figure 18F:
Figure 18G:
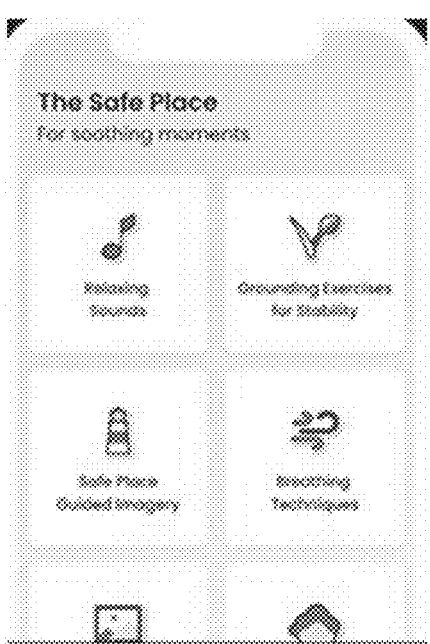
Figure 18H:
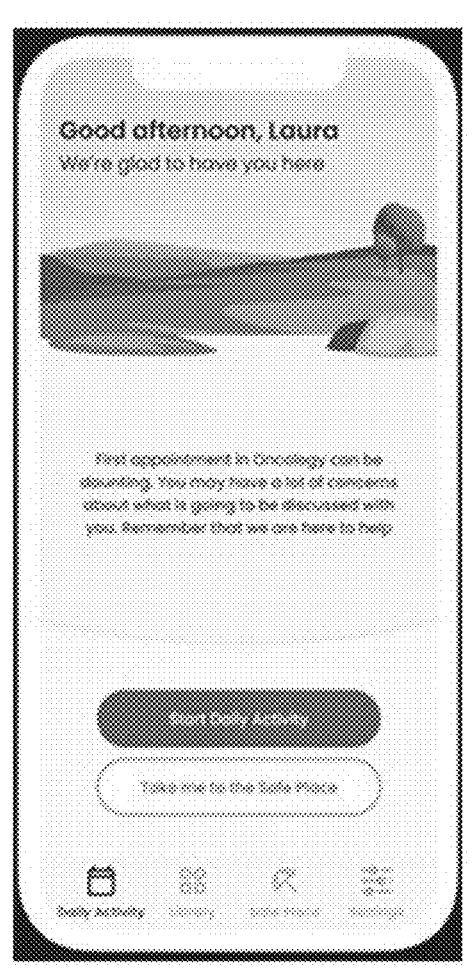

FIGS. 18A-18I shows various screenshots from the digital therapy intervention platform e.g., a mobile phone application. FIG. 18A shows a progression chart for muscle relaxation. Any of the data described herein is graphically available on the digital interface. The display shows a number of scroll-tabs that the user can select e.g., badges, personalize, share, etc. Tabs are present at the bottom of the display allowing the user to navigate other options e.g., settings. FIG. 18B shows an example of a personalized welcome screen. The screen shows what the daily activity will be and provides options for reminders to sync with the user's schedule. FIG. 18C shows options in the "Explore" tab. This provides the user with further options to navigate various aspects of the digital therapy intervention plan e.g., education, anxiety, stress, sleep management, etc. FIG. 18D shows another screenshot providing the user with options in the form of tabs, to navigate the digital platform. FIG. 18E shows a screenshot of a slide-rule feature where the user provides an answer to "how do you feel today". The user's answer is stored and used to plan and personalize their digital therapy. Other questions can be asked to the user in this manner. FIG. 18F shows a screenshot where the user can select various symptoms that they feel; this can be done on a daily basis, or intervention by intervention basis, to prime the digital therapy platform to personalize the interventions accordingly. As with all data received by the software application (e.g., the app) it can be stored and used for analysis and implementation purposes. FIG. 18G shows one feature whereby a user can enter a 'safe place' and select a variety of interventions, primarily to reduce stress and improve wellbeing. FIG. 18H shows a screenshot of a welcome screen where a user can select, before their daily activity, whether they want to go to their 'safe place' (to carry out pre-intervention exercises) to get the user in a better frame of mind before undertaking a daily task.

FIG. 18HI shows a screen shot of a mobile phone application prior to a user undertaking a digital maze. The user is given information about the difficulty level, shown a schematic of the maze, and informed about which sensory modes may be involved in this particular navigation of the digital maze. For example, the screenshot shows "difficulty level— full sight". This means that there is no 'clouding' to impair the visual cues. In various embodiments the digital mazes are named. This provides another mode by which the user's memory can be incorporated into the learning experience.

The digital mazes of the invention comprise allocentric elements, egocentric elements, or a combination thereof, in various embodiments. In an "allocentric" frame of reference, directions and locations are defined relative to external landmarks or a global coordinate system, independent of the observer's position or orientation. In the context of a digital maze, an allocentric maze is designed such that the layout and structure remain consistent regardless of the perspective of the observer. The maze's walls, paths, and landmarks would be fixed in relation to each other, and the observer navigates by referencing these fixed features. For example, in a digital allocentric maze, a path might be described as "turn right at the T-junction" or "go straight until you reach the blue door. In contrast, an "egocentric" frame of reference defines directions and locations relative to the observer's own position and orientation. In a digital egocentric maze, the layout and structure of the maze would appear differently depending on the observer's perspective. For example, if the observer turns left, the maze's layout would shift accordingly, and what was previously on the left might now be on the right. Directions within an egocentric maze would be described in relation to the observer's current position and orientation. For instance, a direction might be given as "turn left" or "move forward two steps". Both aspects can be incorporated into the digital mazes of the invention.

Methods and processes that carry out digital mazes are referred to as a "computer-implemented" method. It refers to any method or process that uses a device to carry out a computation. For example, the computer-implemented method uses at least one electronic device, which can compute, to perform tasks, manipulate data, process digital information, execute algorithms, support software. The computer-implemented method encompasses any functionality that relies on the computational power, storage capabilities, and processing abilities of electronics devices, as described herein. The computer-implemented method can execute instructions or algorithms, by processors or computing devices. Instructions may be stored in a computer-readable memory, such as random-access memory (RAM), read-only memory (ROM), or storage devices such as hard drives or solid-state drives. In various embodiments, the methods of the invention provide such computer-implemented methods, by means of a personal electronic to carry out various tasks, including a digital maze that an individual navigates.

In one embodiment the invention provides a computer-implemented method for digital therapy for an individual, said method comprising:

presenting the individual with a digital maze on a personal electronic device; wherein the personal electronic device provides sensory modality input selected from: visual, auditory, tactile, or a combination thereof, to enable the individual to navigate the digital maze from a starting point to a finishing point.

In one embodiment the invention provides a computer-implemented method comprising:

navigation of an individual in a digital maze on a personal electronic device;

wherein the individual uses sensory modality inputs selected from: visual, auditory, tactile, or a combination thereof, to complete said digital maze from a starting point to a finishing point.

In one embodiment the digital maze comprises at least one obstacle selected from: outer wall, inner wall, dead end, object, turn, interconnected paths, or a combination thereof. "Obstacles" are defined as any individual item comprised in the digital maze. In its simplest form the maze can have no obstacles, and the individual needs to navigate from a starting point to a finishing point. In some embodiments the finishing point is viewable from the starting point. However, the digital maze can be of any shape, such as a winding corridor, where the user needs to navigate from start to finish. Obstacles are generally placed in the digital maze to add complexity and/or difficulty to the maze, however, as will become clear, the mere placement of objects in the maze isn't the only factor that can add to the complexity and difficulty of the maze.

In one embodiment the sensory modality inputs are configured to assist said individual in completing said digital maze in the shortest time, shortest path, with fewest obstacle impacts, or a combination thereof. For example, a user may see the maze in a digital format (e.g., on a phone application) and can swipe the phone to navigate through the maze. Additionally, the user may receive auditory cues to, for example, inform the user how close he is to an obstacle. In some embodiments each obstacle will have its unique sensory cue e.g., vibration, melody, sound, etc. In one embodiment the user is at least partially blindfolded when navigating the digital maze.

In one embodiment digital maze is presented to the individual to be repeated at least once. In one embodiment the digital maze is repeated between 1 and 10 times. In one embodiment the digital maze is repeated between 1 and 50 times. In one embodiment the digital maze is repeated between 1 and 100 times. As the user familiarizes himself/herself with the maze, they will become more proficient in completing the maze. The user may repeat the maze of the same difficulty. Otherwise, the user may return to easier mazes, as will be explained. One aspect of the digital mazes is that they become increasingly more challenging to the user. Since the digital mazes are used in digital therapy interventions, the element of progression through mazes of increasing difficulty is added, in various embodiments.

In one embodiment the method further comprises generating a performance score upon completion of each digital maze by taking into consideration the time taken, path taken, the number of obstacle impacts of the individual, or a combination thereof, when navigating said at least one digital maze. Each maze may have different elements that need to be considered in order to generate a performance score. The examples provided to generate a performance score are for the purposes of example alone. Each performance score can be personalized according to the user's needs and requirements. For example, the performance score for a simple maze may be the same as for a difficult maze, but they are weighted differently, because the difficult maze was more challenging to complete. This is taken into account when assessing the user's general performance in the digital mazes. It is also particularly relevant in tracking the user's progress through the digital maze exercises, and deciding how next to proceed. In one embodiment the method further comprises generating a threshold performance score for the digital maze, above which the individual is no longer presented with the digital maze to complete. The examples provided to generate a threshold performance score are for the purposes of example alone. Each threshold performance score can be personalized according to the user's needs and requirements. Thus, in various embodiments, the method comprises repeating the digital maze until a threshold performance score is achieved. In one embodiment, even if a threshold performance score is achieved, the user can decide to continue repeating that digital maze. In one embodiment the threshold performance score is changed to make the completion of a maze more challenging. For example, a simple maze can be made more challenging by increasing the threshold performance score. This would mean that the user would, for example, need to complete the maze quicker, or along a more efficient path, etc.

In one embodiment the method further comprises the personal electronic device providing a plurality of the digital mazes wherein an increase in sensory substitution is exhibited for each digital maze in the plurality of said digital mazes, following the completion of each digital maze and/or said threshold performance score being achieved; and wherein the sensory substitution comprises the personal electronic device providing the at least partial substitution of at least one of said sensory modality inputs with at least one other of said sensory modality inputs.

In one embodiment the method further comprises repeating a plurality of said digital mazes, wherein following the completion of each digital maze and/or said threshold performance score is achieved, an increase in sensory substitution is exhibited for each subsequent digital maze in the plurality of said digital mazes;

wherein the sensory substitution comprises the at least partial substitution of at least one of the sensory modality inputs with at least one other of the sensory modality inputs.

As mentioned above, and in one embodiment, the user can decide to repeat a digital maze even if he has completed it previously and/or he has achieved the threshold performance score.

In one embodiment the method further comprises the complete substitution of one of the sensory modality inputs with at least one other of the sensory modality inputs selected from:

visual to auditory and/or tactile;

auditory to visual and/or tactile;

tactile to visual and/or auditory.

In one embodiment the personal electronic device is configured to execute the navigation by means of touch gesture, motion gesture, voice commands, text input, camera and media interaction, sensor-based interactions, or a combination thereof. In one embodiment the touch gesture comprises: tapping, swiping, scrolling, pinching, dragging, double-tapping, or a combination thereof. In one embodiment the motion gesture comprises: tilting, shaking, rotating, body motion, waving, or a combination thereof.

As the individual navigates the maze, the sensory cues can change to direct him through. In one embodiment the audio cues are selected from: a change in pitch, change in loudness, change in tone, change in melody, change in rhythm, change in music or a combination thereof. For example, if the individual gets closer to a wall the sound may get louder, or change pitch. This is true if the individual moves closer to the wall, but it can also occur for a moving obstacle which moves towards or away from the individual. The auditory cue can change for each object, e.g., a particular melodic phrase for each individual object. The individual can then be asked about the presence of various objects in the maze. For example, once the digital maze is completed, the user can be asked to identify the objects (and how many of them there were) in the maze by use of auditory cues alone. As the individual progresses through the digital mazes, incorporating sensory principles, the user will recognize that specific sounds corresponding to specific objects. The user may be asked to draw a sketch of the maze afterwards, based on the user's navigation through it, using auditory cues alone. The same principle applies to tactile cues. For example, a particular tactile cue can correspond to different events in the digital maze e.g., approaching an obstacle, hitting an obstacle, nearing the finishing point, etc. A particular vibration can correspond to these digital maze events e.g., double-vibration, short vibration, long vibration, a particular vibration rhythm, etc.

In one embodiment the method further comprises at least one additional device selected from: health monitoring system, medical device, haptic device, external speakers, headphones, virtual reality set, augmented reality glasses/devices, biofeedback sensors, wearable activity trackers, smartphone, personal computational device, smart speakers, voice assistants, motion tracking sensor, virtual assistant systems, internet hub, or a combination thereof; wherein the at least one additional device is configured to transfer data between said individual, said personal electronic device, or a combination thereof. In one embodiment the personal electronic device, the at least one additional device, or a combination thereof, are configured to provide said sensory modality inputs. In one embodiment the tactile input is a vibration.

In one embodiment the individual completes a plurality of digital mazes of increasing difficulty following the completion and/or achievement of a threshold performance score, for each digital maze. In one embodiment the method further comprises the personal electronic device providing a plurality of digital mazes of increasing difficulty following the completion and/or achievement of said threshold performance score, for each digital maze.

As will be understood, an individual can complete and repeat a single digital maze any number of times. That same digital maze can then be repeated using the 'sensory principles' of sensory inhibition, sensory substitution, sensory integration, or a combination thereof. This also applies to any maze of any difficulty. Thus, once an individual has completed a simple maze, and gone through the sensory inhibition/substation/integration, of varying levels, the individual can then do the same for other digital mazes, but of increased difficulty. The individual can also return to any of the digital mazes that were previously attempted and/or completed. For example, if the individual had taken a break from carrying out the digital interventions, the individual can return to the easier digital mazes which were easier to complete.

In one embodiment the method further comprises the personal electronic device providing an increase in sensory substitution exhibited for each of the digital maze of increasing difficulty:

wherein said sensory substitution comprises the personal electronic device providing the at least partial substitution of at least one of the sensory modality inputs with at least one other of the sensory modality inputs.

In one embodiment the method further comprises the complete substitution of one of the sensory modality inputs with at least one other of the sensory modality inputs selected from:

visual to auditory and/or tactile;
auditory to visual and/or tactile;
tactile to visual and/or auditory Modifying the difficulty of the digital maze can come in many forms. It will be understood that the difficulty level of a particular maze is dependent on the individual navigating the digital maze. For example, different obstacles or different sensory substitutions will be more challenging to some individuals than others. However, guiding principles can be used to generally design the digital maze to be increasingly more difficult. In one embodiment the increasing of the difficulty is achieved by: randomly generating a digital maze of a different structure, increasing the path length, increasing the number of turns, increasing the number of obstacles, diversifying the types of obstacles, decreasing the path width, incorporating a time challenge, increasing the performance threshold, changing the sensory modality inputs, adding interactive elements, incorporating distractions, incorporating tasks, incorporating moving obstacles, or a combination thereof "Turns" refers to changing the path direction within the digital maze e.g., with a wall, or an obstacle. "Diversifying the types of obstacles" refers to the different types of obstacles e.g., placing more of one type of obstacle compared with another. Increasing the performance threshold means that the individual needs to complete the digital maze more effectively, in a shorter time, with fewer crashes into obstacles, etc. Changing the sensory modality inputs refers to using the sensory principles to add complexity to the digital maze. For example, using clouding of the digital maze, means that the user must rely on auditory/tactile cues rather than vision. Or an auditory cue can be changed so that the user must figure out how to next proceed in the maze, given that change. The digital maze can be made into a game where the user needs to interact with an element in the digital maze. For example, the user needs to reach a particular location within the digital maze, before the user proceeds to the finishing point. The user may be asked to interact with various elements in the maze. For example, the user can be instructed to 'carry' one item at one point in the maze, and transfer it to another location in the maze. In various embodiments, these interactive tasks may rely on auditory cues alone, whereas navigation in the maze is visual. For example, a task may require the user to pick up an object and place it on the other side of the maze, but the only cue that the user receives about the object is a louder sound when the user is close to the object, a different sound when the user picks up the object, and another sound to direct the user to place the object at a particular location. These principles can be applied to any configuration of the digital mazes and the examples provided herein are not intended to be limiting in scope. In various embodiments, the digital mazes provide a platform from which to execute the sensory principles, primarily for digital interventions. Digital mazes are designed to test a user's memory and aims to improve it. As such, a user can be asked to recall elements that were experienced during navigation in the digital maze e.g., a portrait on a wall, or the position of an obstacle, etc.

The digital interventions described herein can be designed as games, and treatment plans can include gamification elements such as badges, scores, leader-boards, ranking, game currencies, and similar elements all triggering user's reward system, resulting in dopamine production and release. This outcome is beneficial on multiple fronts. It improves adherence to the digital interventions themselves as well as to the treatment plan as a whole. It also carries several therapeutic benefits. An increase in dopamine can modulate the immune system. In addition, in some diseases such as Parkinson's disease, where patients suffer from reduction in dopamine in the brain, and many patients are in fact treated with dopaminergic drugs, the increase in dopamine in the brain triggered by the digital interventions, might have a therapeutic effect on its own or in combination with such drugs. In one embodiment the method further comprises gamification elements. In one embodiment the gamification elements are selected from: badges, scores, leader-boards, ranking, game currencies, quests or missions, characters or avatars, virtual goods, social media features, experience points (XP), or a combination thereof.

In one embodiment the digital maze comprises between 1 and 1,000,000,000 obstacles. In one embodiment the digital maze comprises between 1 and 1,000,000 obstacles. In one embodiment the digital maze comprises between 1 and 1,000 obstacles. In one embodiment the digital maze comprises between 1 and 100 obstacles. In one embodiment the digital maze comprises between 1 and 10 obstacles. In one embodiment the digital maze comprises between 1 and 5 obstacles.

In one embodiment the obstacles are stationary, moving, or a combination thereof. In one embodiment the obstacles and stationary. In one embodiment the method further comprises delivering instructions to the individual before, during, after, or a combination thereof, said digital maze.

The digital mazes can be executed by an individual on any number of platforms and with any number of devices e.g., a personal electronic device. In one embodiment the personal electronic device is selected from: smartphones, tablets, wearable device, smart TVs, computers, laptops, E-readers, gaming consoles, smartwatches, fitness trackers, portable media players, digital cameras, virtual reality (VR) headsets, augmented reality (AR) device, portable GPS devices, portable Bluetooth devices, portable digital assistant, smart glasses and audio device or any combinations thereof.

In one embodiment the computer-implemented method is for use in a digital therapy. In one embodiment the computer-implemented method carries out at least one digital therapy intervention. In one embodiment the computer-implemented method is for use in a digital therapy intervention plan. Therefore, use of the digital mazes of the invention are incorporated into any of the digital therapy interventions disclosed herein.

In one embodiment the digital therapy comprises at least one digital therapy intervention comprising: sensory inhibition, sensory substitution, sensory integration, or a combination thereof, to said individual. Thus, the sensory principles employed for executing the digital mazes, and the implementation of sensory inhibition, sensory substitution, sensory integration, or a combination thereof, are understood as disclosed elsewhere herein.

Digital Therapy Systems of the Invention

The digital therapy interventions of the present disclosure are carried out on digital therapy systems. Digital therapy systems will now be outlined in their various embodiments.

In one embodiment the invention provides a digital therapy system comprising:

at least one processor of at least one personal electronic device, said at least one personal electronic device comprising an internal storage system; and a software application for a digital therapy intervention which performs the computer-implemented method of the invention.

As understood herein "software application" is a program that runs on a device. In various embodiment the "software application" is a computer program which performs specific tasks or functions on a device.

In one embodiment the digital therapy intervention comprises a plurality of intervention sessions. In one embodiment the system further comprises digitally stored instructions for the digital therapy intervention;

wherein said at least one processor is configured to perform said digitally stored instructions causing said software application to perform functions on said personal electronic device, and wherein said software application is further configured to:

receive user inputs via a plurality of interactive elements;

process said user inputs and transfer data between said internal storage system and said software application to carry out said plurality of intervention sessions; and display a graphical user interface (GUI) on said personal electronic device related to said digital therapy intervention.

In one embodiment the system further comprises at least one analysis tool based on machine learning, artificial intelligence (AI), statistical modeling, or a combination thereof, configured to analyze said data for analysis and personalization of said digital therapy intervention.

In one embodiment the system further comprises an external storage system. In one embodiment the system further comprises at least one external storage system. Examples of external storage systems include, but are not limited to: databases, USB storage, network-attached storage (NAS), cloud server, online repositories, or a combination thereof. In various embodiments the analysis tools are based on real-time or historical analysis of user data, adjusting the interventions, therapeutic content, and/or interaction modalities according to the user requirements. In one embodiment the machine learning tool employs deep learning algorithms to predict user responses and optimize therapy sessions preemptively. The deep learning methods are also incorporated into the methods disclosed herein.

In one embodiment the plurality of interactive elements are selected from: user commands, user selections, data input, or a combination thereof. In one embodiment the GUI is presented to the user in a format selected from: text, images, video, audio, or vibration, in response to user interactions and/or information regarding the software application. In one embodiment GUI adapts its presentation format based on the user's device type, accessibility settings, or past user interactions. In one embodiment the system is further configured to perform a plurality of background tasks. Examples of background tasks include, but are not limited to: maintaining application functionality, data synchronization, updates, notification delivery to the user, system monitoring, error logging, cache management, security checks, data encryption, or a combination thereof. In one embodiment the at least one processor is configured to onboard, transfer, analyze, or a combination, data selected from: user interactions, user preferences, user demographics, user usage patterns, user feedback, timestamps, data from said plurality of intervention sessions, or a combination thereof. In one embodiment the GUI is configured to adapt its presentation format based on the individual's device type, accessibility settings, past user interactions, or a combination thereof.

In one embodiment the system further comprises at least one wireless network device configured to transfer data wirelessly. Examples of wireless network devices include, but are not limited to: Wi-Fi adapter, cellular modem, Bluetooth module, near field communication chip (NFC), wireless local area network (LAN) card, wireless router, and wireless access point. In one embodiment the system is further configured to carry out the digital therapy intervention in any of the following formats: instructional video, interactive video comprising input and feedback from the individual, game, instructional prompts, question and answer survey with feedback, virtual reality, augmented reality, or a combination thereof.

In one embodiment the system further comprises at least one additional device selected from: health monitoring system, medical device, haptic device, external speakers, headphones, virtual reality set, augmented reality glasses/devices, biofeedback sensors, wearable activity trackers, smartphone, personal computational device, smart speakers, voice assistants, motion tracking sensor, virtual assistant systems, internet hub, or a combination thereof; wherein said at least one additional device is configured to transfer data between said individual, said personal electronic device, or a combination thereof. In one embodiment the at least one additional device is a health monitoring system.

In one embodiment the system is configured to transfer data between said at least one additional device and said system to personalize said digital therapy intervention. Thus, the system sends/receives/incorporates/transfers data from the at least one additional device or other health monitoring systems for enhanced personalization and accuracy of therapy.

Digital Therapeutics for Treatment of Neuro-Degenerative Diseases Like AD

The present invention pertains to the field of digital therapeutics (DTx), which is primarily software-based and aimed at delivering care to patients.

Digital therapeutics digitize already accepted disease management techniques, such as cognitive stimulation therapy (CST). Digital therapeutics provides nonpharmacological interventions, such as psychosocial interventions, which are effective in preventing, reducing or treating non-cognitive symptoms. Similarly, rehabilitative interventions such as cognitive stimulation therapy, cognitive rehabilitation, physical exercise and gait/balance training can improve cognition, function, stability and/or the quality of life of people with dementia. Cognitive abilities and functions such as attention, memory, executive functions, planning and perception are typical components targeted with digital therapy interventions.

The present invention provides a digital platform to carry out at least one of the following for a disease or disorder: treat, modify symptoms of, alleviate, ameliorate, reduce the progression of, delay the onset of, prevent the worsening of, or improve the quality of life in individuals suffering from a disorder. As understood here, the terms "disease", "disorder", "condition", "syndrome", "ailment", "affliction", "malady", "pathology" and "sickness" are used interchangeably in various embodiments as they pertain to the functions carried out by the digital therapy.

In one embodiment DTx is used to treat neuro-degenerative diseases. As such, and in some embodiments at least two principal mechanisms (or modes) of action are employed, which are complementary to each other. A first aspect is comprised of digital interventions that aim to directly affect the brain to improve spatial and verbal memory and cognition and increase synaptic connectivity. A second aspect is comprised of digital interventions that modulate the immune system (through the application of a top-down approach), in order to improve the way it functions in protecting the brain from the harmful effects of neuro-degenerative diseases. As will be detailed below, each of these modes can be employed on a standalone basis or in combination with certain drugs used to treat neuro-degenerative diseases. In one embodiment the digital therapy comprises at least one cognitive intervention. In one embodiment the digital therapy comprises at least one psychological intervention. In one embodiment the digital therapy comprises at least one cognitive intervention and at least one psychological intervention. In one embodiment the digital therapy comprises at least one cognitive intervention, at least one psychological intervention, or a combination thereof. Altogether, the interventions improve synaptic connectivity in the brain and improve brain elasticity in patients suffering from neuro-degenerative diseases and other neurodegenerative diseases, such as Parkinson's disease, as detailed herein. The digital interventions are ultimately expected to slow or halt the cognitive decline associated with neuro-degenerative diseases.

The specific protocols for digital interventions described herein are provided merely as exemplary embodiments and are not intended to limit the scope of the present invention, as various alternative protocols for digital interventions can be designed based on the same underlying principles.

Digital Interventions Aimed at Improving Synaptic Connectivity

The digital interventions included in this mode operate directly on the brain, improving synaptic connectivity and brain elasticity and strengthen spatial and verbal memory.

It is noted that sensory and multisensory stimulations can effectively ameliorate the pathology of neuro-degenerative diseases (e.g., Alzheimer's disease (AD)), arouse memory, and improve cognition and behaviors. Moreover, digital therapy causes brain nerve oscillation, enhance brain plasticity, and regulate regional cerebral blood flow. In addition, evidence is provided showing neuro-plasticity throughout aging as well as the early stages of dementia. The data provided demonstrates the ability of people with early-stage AD to relearn previously forgotten information or otherwise improve cognitive abilities following a cognition-focused intervention. Therefore the existence of compensatory processes is shown, even in the presence of dementia-related pathology.

As will be demonstrated, reprogramming the brain through sensory substitution devices and methods (including sonification, that is the conversion of data into sound signals that can be perceived by the human ear and interpreted by the brain), increases activation in certain brain areas and improve synaptic connectivity between parietal areas and the hippocampus (both of which are related to spatial and verbal memory), and between the peripheral visual navigation areas (which play a role in detecting landmarks and cues that are used for spatial navigation and processing) and other brain regions involved in spatial processing, including the posterior parietal cortex and the hippocampus.

As will be described, visual deprivation (by blindfolding) leads to rapid neuroplastic changes in the sighted, including a recruitment of peripheral visual navigation areas and the primary visual cortex for tactile and auditory processing.

The present invention thus comprises digital interventions based on multi-dimensional sonification (integrating verbal & spatial information and transmitting it through sound), which require the trainee to employ both spatial and verbal abilities while he or she is blindfolded, in various embodiments. These interventions aim to promote neuroplasticity and increase synaptic connectivity and activity in areas specifically impacted by neuro-degenerative diseases such as AD, particularly those related to spatial cognition, memory, and language, to prevent or delay dysconnectivity and cognitive decline associated with the disease. Examples will be provided throughout.

Mazes Integrated, Some of which are Integrated with Topo-Speech Algorithm ("TopoSpeech Mazes")

Cognitive-training mazes including auditory stimulants serving to convey spatial information about the maze, can activate brain areas related to navigation and spatial cognition. Examples of such mazes include Hebb-Williams and Morris water mazes. The present invention includes digital interventions aimed at treating patients with neuro-degenerative diseases such as AD, which are predicated, among other things, on these insights. FIGS. 1A-1B and FIGS. 2A-2D includes certain examples for digital maze screenshots and drawings of the mazes. FIG. 1A shows a screenshot from a mobile phone application where a user navigates through a maze from a starting point to a finishing point. In FIG. 1A the exit point is not visible whereas the floor, walls, and paintings on the walls are visible. Once the user navigates through the maze, the exit point is visible in FIG. 1B. As will become clear, a user navigating the mazes use visual and auditory cues. One of the methods employed is to increasingly rely less on visually seeing the maze, and more on auditory cues. As such, the user will navigate mazes of increasing complexity, eventually, by sound alone.

In addition to the use of virtual versions of mazes (or similar spatial challenges) along with auditory stimulants, the present invention utilizes in one of its embodiments the "TopoSpeech" algorithm, a novel sensory substitution method that conveys spatial information through language and auditory properties to the blind and visually impaired. The algorithm assigns a name to an object in space, such as a bottle or a laptop, and represents its location through auditory properties, with higher pitched sounds indicating higher objects and temporal properties determining the horizontal axis.

To maximize results with AD patients, digital interventions based on navigation through mazes (or similar spatial challenges) combined with auditory stimulants (including, in some instances, an application of the TopoSpeech algorithm) need to be operated on blindfolded subjects. As used herein, the subject using or undergoing the digital therapy interventions is referred to in a number of ways. For example, a "user" can also be referred to, and understood interchangeably, as a "patient", "individual", "subject", "participant", "recipient".

In one embodiment, TopoSpeech Mazes are carried out through a combination of all the elements described above: an integration of (x) spatial (non-verbal) information about the maze with (y) TopoSpeech (verbal) information, which is (z) administered to a blindfolded subject by the use of sonification techniques and sensory substitution. In order to solve the mazes, the trainee is expected to utilize both spatial and verbal clues, and thus use a combination of spatial and verbal skills, the two most important brain functions impaired in AD patients (both of which are in the hippocampus and connected brain structures). In various embodiments, the integration of the foregoing elements facilitates multisensory integration, and increase cortico-cortical connectivity in brain regions associated with Alzheimer's disease, such as the parietal areas and hippocampus, which are involved in both spatial perception and memory.

Example 1 below (also referred to herein as the "Ageing Trial" and "Study A") shows some aspects of the benefits of the claimed invention. As part of the Ageing Trial, a mobile application was employed with a sensory training program targeting cognitive abilities in aging participants (55-60). Over a two-week period, the effects of the digital egocentric navigation training was assessed, as facilitated by an app (based, in part, on Hebb Williams mazes combined with auditory stimulants and blindfolding). Study endpoints encompass, inter alia, brain functional and structural connectivity, psychological well-being, and certain biomarkers. Other results include, among other things, that measure the effect of the intervention on hormones and antibodies related to learning processes and stress.

Multi-Dimensional Memory Training

Another embodiment of the present invention, based on similar principles, consists of digital interventions that perform multi-dimensional memory training. An example for this type of digital intervention is a memory training that utilizes the TopoSpeech algorithm, where the subject must try remembering the order of words played to the subject before as well as their "location" in space. In various embodiments, this type of digital intervention is carried out on blindfolded subjects.

The digital intervention platform provides many different types of interventions that can be used individually, or a combination to achieve positive outcomes, as will be described.

In some modalities of the present invention the digital interventions described herein may be administered with other types of sensory stimulations, including tactile stimulations (e.g., through rotations of the phone), which would be integrated within the DTx.

Digital Interventions Directed at Modulating the Immune System

There is a strong connection between the immune system and neuro-degenerative diseases, including AD. The principle mechanisms by which the digital interventions affect AD apply, correspondingly, to other neuro-degenerative diseases, as will become clear.

In one aspect, the immune system exerts a significant influence in the clearance of beta-amyloid plaques within the brain, which, as explained above, are known to disrupt regular brain activity and exacerbate Alzheimer's disease (AD) symptoms. In one aspect, the clearance process is achieved via phagocytosis, where immune cells known as phagocytes, including microglia, infiltrate the brain and eliminate detrimental agents, including beta-amyloid plaques. In AD, the immune system and the brain interact in a complex and dynamic manner, which can have both beneficial and detrimental effects on disease progression. On the one hand, the immune system plays a critical role in clearing beta-amyloid plaques from the brain, and on the other hand, chronic activation of the immune system can lead to neuroinflammation, which has been linked to neuronal damage and cognitive decline in AD.

Figure 3:
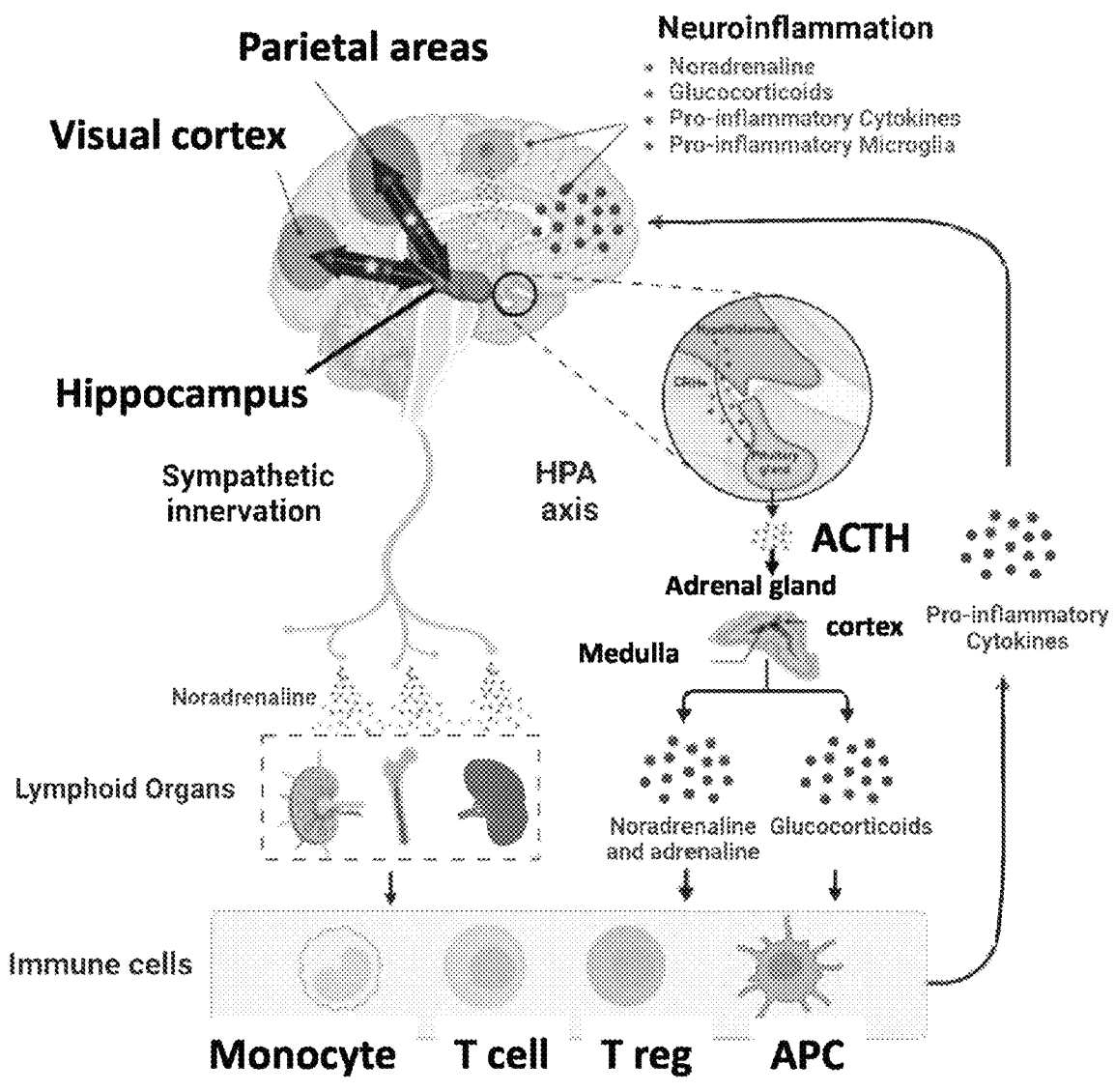
FIG. 3 is a schematic representation of the effects of digital therapy on neuroinflammation.

Neuroinflammation in AD is driven, in part, by the activation of microglia and other immune cells within the brain. These cells release pro-inflammatory molecules, such as cytokines and chemokines, which can attract more immune cells to the site of injury and promote further inflammation. Over time, this chronic neuroinflammation can lead to the accumulation of neurotoxic molecules and the loss of synapses and neurons, contributing to the cognitive decline seen in AD. FIG. 3 shows a schematic example of some of the related mechanisms involved.

With reference to FIG. 3, various pathways are shown wherein digital therapy positively affects a variety of processes and indicators. Digital therapy is shown to reduce neuroinflammation, noradrenaline and adrenaline, glucocorticoids and pro-inflammatory cytokines. As shown throughout, the digital interventions enhance synaptic connectivity and neuroplasticity and/or modulate the immune system.

Immunotherapy enhances effectiveness of phagocytes in clearing beta-amyloid plaques and decreasing neuroinflammation. Immunotherapy is a relatively new class of medications that treat disease by modulating a patient's own immune system to achieve an optimal response against the disease from which the patient suffers.

Immunotherapy, and specifically immune checkpoint inhibitors (ICIs), are a promising approach for treating Alzheimer's disease (AD) by modulating the immune system to enhance its ability to clear beta-amyloid plaques from the brain. Immune checkpoint inhibitors are a class of drugs that block the activity of molecules that dampen the immune response, such as programmed cell death protein 1 (PD-1) and cytotoxic T-lymphocyte-associated protein 4 (CTLA-4). By blocking these molecules, immune checkpoint inhibitors trigger the immune system and enhance the immune system's ability to clear beta-amyloid plaques from the brain. Additionally, immune checkpoint inhibitors can reduce neuroinflammation, a hallmark of AD, by inhibiting the activity of pro-inflammatory immune cells. A Empowering the peripheral immune system can augment the activity of T cells, resulting in increased availability of IFN-g, which activates the choroid plexus (CP) epithelium to express leukocyte trafficking molecules. The enhanced ability of the CP to express these molecules supports the recruitment of monocyte-derived macrophages and regulatory T cells to the brain. The monocyte-derived macrophages can directly, as well as indirectly, display multiple activities, including suppression of the inflammatory milieu of the brain via local production of IL-10, facilitating removal of amyloid-beta oligomers and plaques by expressing unique scavenger receptors (e.g., MSR1). Such an immune modulation is followed by enhanced neuronal survival, the rescue of synapses, and a more supportive environment for the functioning of the brain. These findings have significant implications for the development of new therapeutic strategies to prevent or treat Alzheimer's disease by targeting the peripheral immune system, which could offer a less invasive and more effective approach for combating this devastating condition.

It is noted that neuro-endocrine imbalance caused by physiological and psychological stressors, and the pro-inflammatory factors profile such imbalance creates, may adversely affect the immune response and produce unfavorable conditions which can potentially impair the success of immunotherapy and exacerbate the potential toxicity of immunotherapy drugs. Therefore, regaining the correct neuroendocrine balance is likely to allow patients to respond better to these drugs and increase their overall effectiveness (i.e., both their efficacy and safety).

Aside from the effect of stress on the immune system (and relatedly, on the effectiveness of immunotherapy), stress can directly impact the progression of neuro-degenerative diseases such as AD. Often, individuals with Alzheimer's disease (AD) have elevated levels of chronic stress mediators, such as cortisol and noradrenaline. These stress mediators, along with the proinflammatory agents they generate, can trigger the activation of microglia—which, as explained above, has a prominent role in the pathogenesis of AD—and induce the release of proinflammatory cytokines in the brain. This, in turn, can lead to neuroinflammation, causing neurotoxicity and exacerbating the process of neurodegeneration and the symptoms of AD. Furthermore, corticosteroids impair the entry of peripheral immunoregulatory cells into the brain, which is essential in restoring homeostasis and preventing stress-induced psychopathologies (see FIG. 3).

In view of the forgoing, the digital interventions of the present invention help induce psycho-physiological effects. As shown herein, various digital interventions reduce stress and induce psycho-physiological effects that facilitate the restoration of neuroendocrine and neuro-immunological balance in AD patients, thus slowing down the progression of the disease. These aspects, as well as other studies showing the deleterious effects of stress mediators on brain structures and their contribution to neurodegeneration, provides evidence that administrating the digital interventions included in this mode to reduce the stress of an AD patient significantly improves his/her state, at least in one of the many metrics used to define improvement. The digital interventions included in this mode of the present invention facilitate the restoration of neuroendocrine and neuro-immunological balance (evidenced by decreased IL-6 and increased CD4+ T cells and IFN-7 levels) and the reduction of neuroinflammation. In addition, these interventions reduce AD-specific distress and improve patients' quality of life (see FIG. 3).

This mode of the present invention thus comprises an apparatus, systems, and methods for treating an AD patient via digital interventions that lower stress and modulate the immune system. The digital interventions are designed to modulate specific brain areas like the pituitary gland and the hypothalamus, which can reduce the activation of the hypothalamic-pituitary-adrenal (HPA) axis. This, in turn, leads to a reduced secretion of stress mediators, including glucocorticoids (such as cortisol) from the adrenal cortex. In addition, the digital interventions also reduce the activation of the sympathetic nervous system (SNS), resulting in a decrease in the secretion of adrenergic factors such as adrenaline from the adrenal medulla and noradrenaline from sympathetic nerve endings. This helps towards achieving a neuro-endocrine balance.

Some forms of digital intervention utilize integrating sensory and multi-sensory stimulations (unique combinations of two or more senses) and immersive body-based interventions that enable the subject to experience the stimulation as embodied in their own body.

Combination with Drugs

As explained above, digital interventions of the types explored herein can be used on a standalone basis or in combination with a medicinal agent. Generally, an adjunctive medication is a supplementary therapeutic agent used in conjunction with primary treatment to optimize efficacy or address specific aspects of a medical condition, often enhancing overall therapeutic outcomes. The present invention provides many options of adjunctive medical agents, otherwise referred to as "non-digital medical interventions". As will become clear, any therapeutic agent that achieves this goal in a combination with the digital therapy of the invention is considered within the scope of the invention. For example, digital therapy interventions for neuro-degenerative diseases together with adjunctive medical agents for neuro-degenerative diseases can be used in combination. In one embodiment digital therapy interventions for improving the immune system together with adjunctive medical agents for improving the immune can be used in combination. As understood, any combination of digital therapy with another intervention that is non-digital is considered within the purview of the scope of the invention.

In addition to immunotherapy, which has been discussed above in connection with where one other type of drugs with which the digital interventions included in the present invention may work synergistically are drugs targeting neuroplasticity, including NMDA-mediated mechanisms. While such drugs are expected to provide an optimal biochemical balance necessary for neuroplasticity, which can enrich the environment in which the drugs operate with cognitive tasks promoting the development of synaptic connections relevant for spatial abilities, memory and other cognitive functions. In addition, certain digital interventions facilitate the rebalancing of the immune system, could further amplify the effect of such medications.

Drugs such as cholinesterase inhibitors or acetylcholinesterase inhibitors ("AChE Inhibitors") are also implemented in combined with digital therapy. These drugs act by inhibiting the enzyme acetylcholinesterase, which is responsible for the breakdown of the acetylcholine neurotransmitter, and thus increasing the levels of this enzyme in the neural synapse. Acetylcholine has a role in the peripheral and central nervous systems, is involved in memory and learning processes, and people with AD often have reduced levels of this neurotransmitter and the neural pathways in the brain that utilize it are compromised, which contributes to their cognitive impairment. By increasing the levels of acetylcholine, AChE Inhibitors can help to improve cognitive function and slow down the progression of AD. The combination of the digital interventions with AChE Inhibitors can result in a synergistic effect and significantly improve the condition of patients.

Anti-amyloid-beta drugs (e.g., the humanized monoclonal antibody Lecanemab) can be combined with the digital interventions described herein.

The digital interventions, combined with Lecanemab, work in at least two pathways. The first is through the interventions' direct effect on the brain, improving synaptic connectivity and neuroplasticity. Structural and functional changes related to the hippocampus and DMN are known to underlie age-related cognitive decline and are accompanied by the accumulation of Aβ. The Examples show an improved post-training connectivity in these areas. Thus, digital interventions can work together with Lecanemab, as it removes existing plaques, enhancing connectivity in these areas, possibly improving cognitive and functional status.

The second pathway by which the digital interventions described herein can work with Lecanemab is by restoring neuro-immunological balance and reducing neuroinflammation. The digital interventions described herein show reduced depression and stress scores, and can, in turn, reduce chronic inflammation, reduce proinflammatory cytokines, and prevent further neurodegeneration.

Donanemab is another example. It is an immunoglobulin G1 monoclonal antibody directed against insoluble, modified, N-terminal truncated form of β-amyloid present only in brain amyloid plaques. Donanemab binds to N-terminal truncated form of β-amyloid and aids plaque removal through microglia mediated phagocytosis.

In the same pathways described above for combination with Lecanemab, the digital interventions described herein can work with Donanemab and any other related anti-amyloid beta drugs.

SAGE-718 is an analog of the neurosteroid 24S-hydroxycholesterol, which acts as a positive allosteric modulator of the NMDA receptor. SAGE-718 administration shows improvement in executive functioning, learning and memory, which aligns with results provided in the Examples, showing increased connectivity between medial temporal lobe (MTL) memory-related areas and executive working memory frontal areas.

Semorinemab is an anti-tau humanized monoclonal IgG4 antibody that targets the N-terminal domain of tau and binds to all known isoforms of full-length tau, and effects connectivity and cognition.

In addition to the specific types of medications specifically mentioned above, the DTx described and claimed as part of the present invention may also work synergistically with other types of disease modifying drugs for AD, whether or not approved as of the date hereof.

While each mode of the invention can be employed separately, they can be employed in tandem and have a synergistic effect. The unique digital interventions described and claimed as part of this invention can also be combined with other computer-based cognitive training programs that help improve cognitive function in AD patients (e.g., exercises that target memory, attention, and other cognitive domains). Overall, the combination of different digital interventions and treatments for AD can provide a more comprehensive and effective approach to managing the disease and improving patient outcomes.

In various embodiments, the digital interventions are administered through the operation of a software application and may be delivered via any screen connected to the Internet (including, without limitation, Mobile, PC, TV, AR Glasses, VR headsets, smart watches, or other wearable devices) and/or any audio devices connected to the Internet (including, without limitation, headset, speakers) and/or any connected haptic devices (such as bracelet, watch, ring, sleeve, belt, wrist bands, vest and more) that can create tactile sensations of heat, cold, vibration, pressure, etc. and/or any smell releasing device and/or any other sensory stimulation devices.

The system may also include an interface that enables connecting to a variety of wearables (including, without limitation, smart watches and bracelets), sensors attached to the body (including, without limitation, scalp, finger, and earlobe sensors) and other devices capable of monitoring activity and detecting various measures of health and other information about the user's body such as temperature, heart rate (pulse), respiration rate, heart's rhythm, heart rate variability and electrical activity, blood glucose levels, muscle tension, sweat gland activity, measures related to quality of sleep and brain waves, as well as measures of the user's physical activity (including steps, calories burning, etc.). In addition, the system will track and assemble patient-reported outcome measures. Such data may then be used to personalize and optimize the digital component while it is being administered to the user (e.g., by way of techniques resembling biofeedback), while also serving as outcome measurements.

The user may communicate with the application through a speech recognition system (SRS) or via tapping/moving vibrating wrist bands (VWB), or writing on the screen during or after the completion of the digital interventions. The system can evaluate the participant's cognition level and personalize the digital interventions to his/her level. The system may continuously collect user data and input to improve and personalize the digital therapy component for the individual user, while continuously improving its general operation (while using AI tools, among other things). Thus, the system described herein will also serve as a data-generating apparatus. The ongoing operation of the system is expected to result in the creation of an ever-expanding improving database that can be used for a variety of purposes, including the development of personally adapted protocols for combination treatments.

Detection

The methods described for treatment of AD via digital tools can also be used as methods for diagnosing AD, alongside other existing methods of detecting AD. This could be done by using these digital interventions to test and evaluate the cognitive abilities of participants and detect breakdown in multisensory integration as a marker for AD that other methods may miss. For example, if a participant's performance of a TopoSpeech Maze deteriorates over time, it can indicate a decline in spatial cognition and serve as a marker for AD. Similarly, the digital interventions described above can be effective for memory testing.

Conditioning

In one embodiment the methods described herein further comprise conditioning. As used herein "conditioning" (or "conditioning stimulus") refers to the process of associating a particular cue or stimulus with the administration of a drug or medication in order to promote positive effects or outcomes. Conditioning can be carried out using sensory modality inputs. Those sensory modality inputs are selected from: visual, auditory, tactile, gustatory, olfactory, proprioceptive, and vestibular. As such, and in various embodiments, the digital methods disclosed herein further comprise a conditioning stimulus which is coupled with a particular drug.

One other aspect of the present invention includes methods of conditioning a patient's brain to enable a patient to enjoy the benefits of the DTx component during and in between treatment sessions and thus make its medication effect more prolonged. These methods are based on the Pavlovian classical conditioning and operant conditioning paradigms, which have been used, for example, to demonstrate that associating morphine with a neutral olfactory stimulus resulted in a morphine-like conditioned analgesic response to the olfactory stimulus. Based on similar principles, the present invention includes methods of pairing the digital therapy component (the unconditioned stimulus) to a "conditioned stimulus" so that the brain is ultimately conditioned to respond to the conditioned stimulus in a similar manner to which it responds to the DTx. This would enable patients to enjoy the positive effect of the DTx, at least to some degree, merely by administering the conditioned stimulus. The pairing and conditioning method described above is particularly beneficial in light of evidenced challenges in adherence to digital therapeutics.

In one embodiment the at least one digital intervention is administered together with a conditioning stimulus selected from: visual, auditory, tactile, or a combination thereof. In one embodiment the medicinal agent, the at least one digital intervention, or a combination thereof, is administered together with a conditioning stimulus selected from: visual, auditory, tactile, or a combination thereof. The conditioning stimulus for the digital intervention and the medicinal agent can be the same or different.

To secure the conditioning effect, at least some of the digital trainings and stimulations will be accompanied with a distinct "conditioned stimulus": for example, a fixed auditory theme (with slight variations), a distinct taste or smell that will be integrated in the digital component, or a multisensory theme ("MST"), i.e., a specific combination of sound, vibration and visuals or any other combination of sensory stimulations. The conditioned stimulus or some aspects of it may be personalized for each user. The conditioned stimulus will be linked in the user's mind to the positive effects of the digital treatment.

In modes of the invention that are based on combination of DTx with drugs, conditioning may also be employed so that the DTx (or the conditioned stimulus linked to the DTx) will gradually acquire some of the drugs' physiological effects, thus enhancing the effectiveness of the digital component.

Thus, the pairing here is between the digital therapy component (or the "conditioned stimulus" (see above) paired with it) and the drug component so that the brain is ultimately conditioned to respond to the digital therapy component in a similar manner to which it responds to the drug. While the digital therapeutics described in this application can be generally expected to have a positive effect on patients, the pairing and conditioning method described above can result in increased adherence to, and efficacy of, such digital therapeutics. This may ultimately facilitate an increased use of the digital component and a concomitant decrease in the weight of the drug component in treatment. In some cases, this may even enable using the digital therapy component as an alternative to the drug or in between drug intakes (thus, making the medication effect of the drug more prolonged). Reducing dosage of the drug component lessen its side effects as well as drug tolerance and associated user dependency.

In various embodiments, the conditioning effect works with respect to certain drugs. Generally speaking, the stronger and/or quicker the relief provided by the drug is, the easier it is to create the conditioning between the digital interventions and the drug.

The digital interventions provided to a patient via the software application (i.e., any of the digital interventions disclosed herein) may be varied on an ongoing basis in order to minimize the weariness effect and maximize adherence to, and efficacy of, the digital component. However, to secure the conditioning effect, at least some of the digital therapy training sessions and stimulations will be accompanied with a distinct "conditioned stimulus". The conditioned stimulus will be linked in the user's mind to the positive effects of the treatment.

In some of the modes for operating the method described herein, there will be an additional step, performed prior to, or in conjunction with, the administration of the drug and the digital interventions, designed to create an adrenaline boost or an emotional arousal in the patient. For the purposes of illustration, the patient may be prompted via a digital application to listen to a 3-minute adventure training, accompanied by 3D sounds, in which he or she is faced with dangerous stimuli (e.g., a lion or a gushing river). The use of such (or other) adrenaline boosters enhances the conditioning process since adrenaline enhances association and learning processes in the brain.

Some embodiments of the invention may also utilize the following (or other) methods of operative coupling: As the conditioning is stronger with better time-locked perceived causality between the conditioned-stimulus (the DTx) and the unconditioned-stimulus (the drug), a stronger connection can be established by implementing a technological protocol that strengthens the association and enforces a requirement to use the digital intervention in order to be able to take the drug immediately afterwards. For illustration purposes only, such protocols may consist of: (1) A requirement to scan the pills' packaging (scan a designated sticker of the digital drug amplifier on the packaging) in order to unlock the instructions for the pills/dose/sequence of the current treatment session. This can be artificially induced, for example when taking several pills, even if the order/sequence is not medically significant. It is also possible to use a dedicated pills' packaging, with a Bluetooth-operated lock, that requires the scan of the designated sticker in order to unlock the box and allow access to the pills. (2) A scan of the pills' packaging triggering a branded AR (augmented reality) holographic animation, as if coming out of the packaging, with the instructions for the pills/dose/sequence of the current treatment session, thus creating a visual association between the DTx and the drug. This visualization can also be designed so that it is used, in addition, to create an association with certain visual stimulations that are administered as part of the DTx (e.g., via VR).

In various embodiments conditioning comprises at least: 1) pairing between digital intervention & drug (so that using the digital intervention will trigger some of the benefits of the drug without actually taking it) and, 2) pairing between digital intervention & a conditioned stimulus (so that using the stimulus will trigger the benefits of the digital interventions).

In one embodiment the at least one digital intervention is administered together with a conditioning stimulus selected from: visual, auditory, tactile, or a combination thereof. In one embodiment the at least one digital intervention, at least one non-digital intervention, or a combination thereof, is administered together with a conditioning stimulus selected from: visual, auditory, tactile, or a combination thereof.

Parkinson's Disease (PD) and Digital Therapy

In various embodiments described herein, reference is made to individual diseases wherein the principle of a particular treatment applies to the broader category of diseases. It is understood that guiding principles that outline effective treatment for neuro-degenerative diseases in general apply correspondingly to other neuro-degenerative diseases as well. Thus, although not stated explicitly, when referring, for example, to treatment plans for Alzheimer's diseases, other corresponding treatments are understood to apply for other neuro-degenerative diseases.

Multiple lines of evidence indicate that immune system dysfunction, as well as neuro-connectivity considerations, has a role in Parkinson disease (PD); this evidence includes clinical and genetic associations between autoimmune disease and PD, impaired cellular and humoral immune responses in PD, imaging evidence of inflammatory cell activation and evidence of immune dysregulation in experimental models of PD. Many adjunctive medical agents and non-digital medical interventions can be used with the digital interventions of the present application.

For example, a central defect in PD is dopamine depletion from the basal ganglia. This results in major disruptions in the connections to the thalamus and motor cortex and results in the classic parkinsonian signs of bradykinesia and rigidity.

Various therapeutic interventions, such as medications, surgery, and rehabilitation, can effectively mitigate symptoms of PD. Among these, Levodopa/carbidopa, a combination medication designed to augment dopamine levels in the brain, stands as the most commonly prescribed for PD. As such, combinations such drugs in combination with digital therapy is shown to be effective against PD.

Levodopa serves as the precursor to dopamine, undergoing conversion in the brain. Simultaneously, carbidopa, acting as a dopamine decarboxylase inhibitor, impedes the peripheral conversion of levodopa to dopamine, facilitating more levodopa to traverse the blood-brain barrier (BBB). Once transformed into dopamine, it activates postsynaptic dopaminergic receptors, compensating for the diminished endogenous dopamine levels.

Levodopa is an effective agent for control of motor symptoms of PD but also requires the most frequent dosing and is associated with the highest risk of dopaminergic motor complications, such as "wearing off" and dyskinesia. (motor complications affect approximately 40 percent of patients with Parkinson disease (PD) after five or more years of levodopa therapy)

In select cases, initial treatment with a dopamine agonist (DA), monoamine oxidase type B (MAO B) inhibitor, or amantadine is a reasonable alternative to early levodopa. Most such patients progress to require levodopa within a few years.

Dopamine agonists work by directly stimulating dopamine receptors in the brain. Initiation of treatment with dopamine agonist monotherapy is now recommended in young patients to postpone therapy with levodopa.

MAO inhibitors are responsible for blocking the monoamine oxidase enzyme, which breaks down different types of neurotransmitters including dopamine. MAO-B inhibitors inhibit the breakdown of dopamine, increasing its available levels. MAO-B inhibitors may be used as early monotherapy or as an add-on to other medications, including levodopa, to reduce motor fluctuations.

Amantadine is an antiviral agent with mild antiparkinsonian activity. The mechanism of action of amantadine in PD is uncertain; it is known to increase dopamine release, inhibit dopamine reuptake, stimulate dopamine receptors, and possibly exert central anticholinergic effects. Amantadine monotherapy is an alternative to early levodopa in younger patients who are at risk for dyskinesia, particularly when tremor is prominent. Aside from use as monotherapy, amantadine can be useful for managing levodopa-induced dyskinesia and "off" time in patients with more advanced PD.

Patients with PD who experience motor complications interfering with quality of life can benefit from device-assisted treatment, including deep brain stimulation (DBS). DBS is the most frequently performed surgical procedure for the treatment of PD. There are two main targets for alleviating motor fluctuations and dyskinesia associated with advanced PD: the subthalamic nucleus (STN) or the internal globus pallidus (GPi).

The procedure for DBS involves stereotactic brain surgery for unilateral or bilateral electrode placement, which are connected to a pulse generator implanted in the chest wall. When turned on, the pulse generator delivers high-frequency electrical stimulation to the particular target (GPi or STN).

DBS for motor complications of PD works in the following hypothetical way: two downstream physiologic effects of the hallmark cellular degeneration of the substantia nigra and corresponding loss of dopamine production are excessive STN excitation of the GPi and excessive GPi inhibition of the thalamus. These, in turn, cause reduced thalamocortical activity, which is believed to mediate akinesia and rigidity. High-frequency DBS suppresses neuronal activity and also activates efferent fiber pathways leaving the targeted nucleus.

The Digital Interventions' Effects on Parkinson's Disease

The interventions described in detail above can benefit patients with PD either on a stand-alone basis or in combination with various drugs for PD.

Additional analysis of Study A (see Example 1) described above revealed that the multisensory psycho-cognitive training shows promise in enhancing the integrity of the basal-ganglia-thalamo-cortical circuit.

Figure 9A:
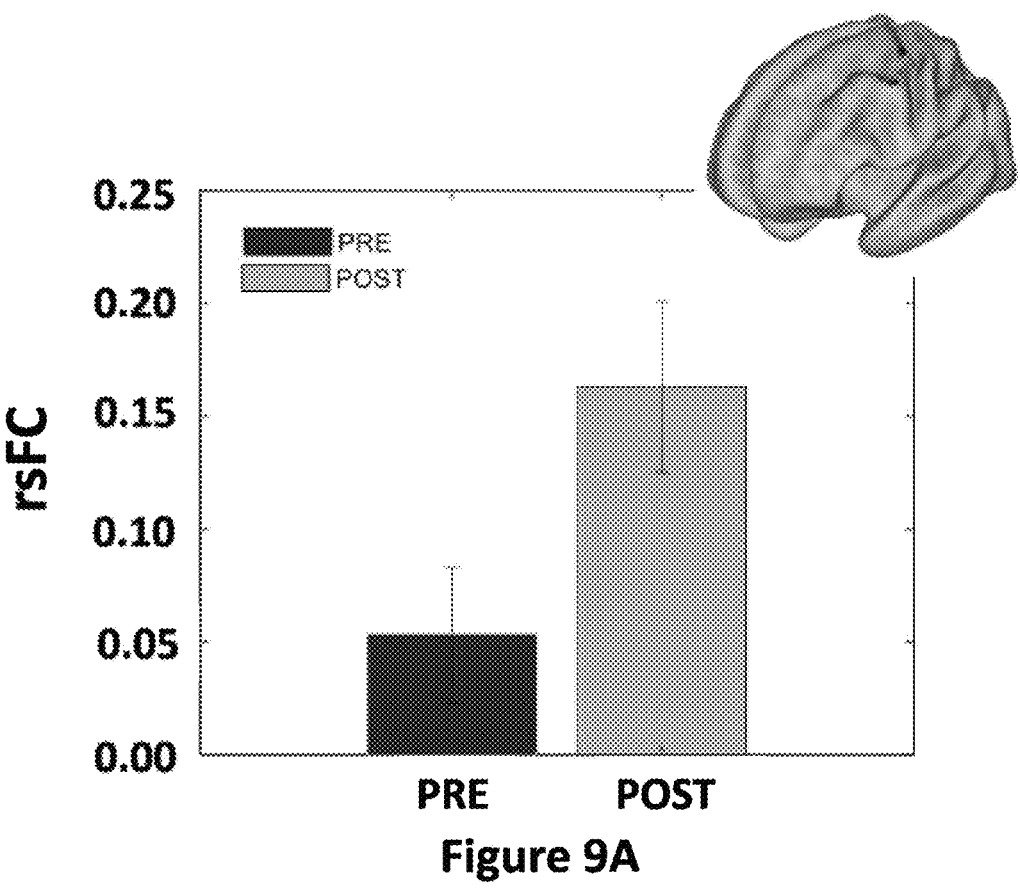
FIGS. 9A and 9B demonstrates results that show increased post training connectivity between Ventral Lateral Thalamus (VTL) and premotor cortex, and a correlation between the VTL/premotor cortex post-training connectivity to the subjects' time spent training.
Figure 9B:
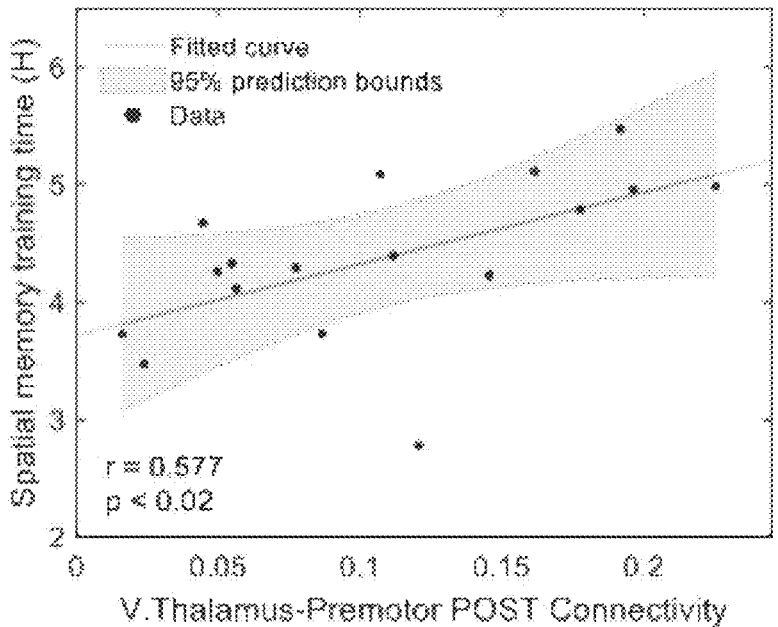

FIGS. 9A-9B shows increased post training connectivity between Ventral Lateral Thalamus (VTL) and premotor cortex, and a correlation between the VTL/premotor cortex post-training connectivity to the subjects' time spent training.

FIGS. 9C-9F shows improved cross talk between frontal areas (BA9) and basal ganglia (GPi). The GPi is one of the targets for DBS described above; it also shows improved connectivity within the basal ganglia network and between the somatosensory system.

An additional aspect involves the impact of the digital interventions described herein on depression scores and the enhancement of connectivity in brain regions associated with depression and immune function, as elaborated above in the description of Study A (and see also Study B, see Example 2, for depression scores and other beneficial psychological effects of the intervention). These effects can contribute significantly to the well-being of PD patients as well as change disease progression. Depression, prevalent among individuals with PD, adversely affects motor function and overall quality of life.

Herein using the interventions described above have shown the ability to restore immune system balance, or otherwise improve various immune system markers and indications. By integrating psychological modules, including components of CBT, with multisensory training, the present invention aims to enhance connectivity in brain areas known to be altered in both PD and depression. This holistic approach can synergistically benefit PD symptoms, improving overall function, mood, and quality of life for affected individuals.

Combinations of Digital Therapy with Drug Therapy

Dopaminergic therapy is the mainstay of pharmacologic treatment for PD. The drugs increase dopamine levels or act as agonists to dopamine receptors, and have been previously shown to modulate functional connectivity in the basal ganglia-thalamic-cortical circuit. Since the digital interventions described herein have shown to enhance functional connectivity in this circuit, combining them with drug therapy can have a synergistic effect.

Combining the present interventions with dopaminergic drugs such as Levedopa enhances their efficacy, leading to a lower dose and less frequent dose changes, and reduce adverse effects.

Alpha-synuclein is a protein which is abundant in dopamine producing nerve cells. In PD, alpha-synuclein misfolds and aggregates into clumps called Lewy Bodies, intracellular inclusions that are the pathologic hallmark of PD. Alpha-synuclein aggregates disturb dopaminergic transmission and induce presynaptic and postsynaptic dysfunctions. Immune response to alpha-synuclein misfolding contributes to disease progression—the presence of early inflammation in experimental models and PD patients, occurring before deposition and spreading of alpha-synuclein suggests a mechanistic link between inflammation and synaptic dysfunction. Examples include, but are not limited to: Prazinezumab, Buntanetap, etc.

These treatments that target alpha-synuclein can be combined with the interventions described herein to achieve better outcomes for PD patients, or other neuro-degenerative diseases.

EXAMPLES

Example 1

Effect of Digital Health Methods on Subjective Cognitive Decline (SCD) and other Neurodegenerative Conditions Two studies conducted by the present inventors will be described.

Summary of Study a and its Results:

The study subjects, aged 55-60 with subjective cognitive decline (SCD), followed a daily digital treatment protocol of 30 minutes during two weeks. Participants were evaluated using psychological questionnaires and resting state fMRI (rsfMRI) at baseline and post-intervention.

The treatment protocol included Maze navigation based on standardized Hebb-Williams mazes and psychological and cognitive interventions such as CBT, psychoeducation, and guided imagery. The digitized maze leverages a combination of map based (allocentric) and environment based (egocentric) navigation. The navigation was initially performed with eyes open, followed by blindfolded navigation assisted by an audio algorithm. This digitized maze experience was developed based on research of the present inventors showing increased brain plasticity following blindfolded navigation training.

Results:

The changes were tracked for behavioral scores and brain imaging measured pre-training and post 2 weeks of training. The main findings:

1. rsfMRI showed increased post-training connectivity between memory-related areas (hippocampal and parahippocampal areas in the medial temporal lobe, MTL) and executive working memory frontal areas (fronto-parietal network, FPN and the anterior and posterior cingulate cortex within the DMN) (p<0.05, FDR corrected).

2. The improvement in connectivity was significantly correlated with post-training maze-solving performance.

Increased rsFC between the MTL and frontal executive areas post intervention are observed.

Figure 8A:
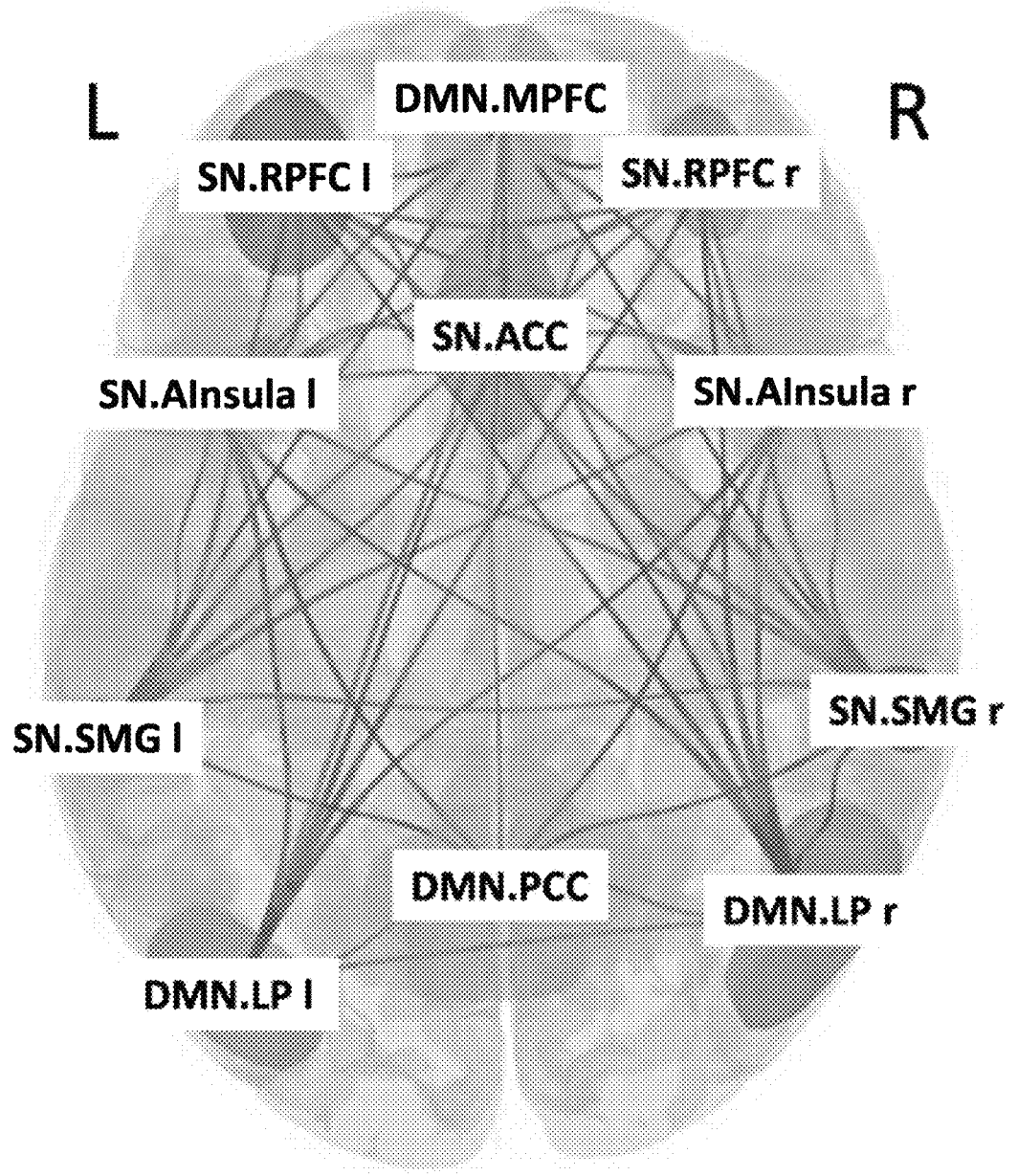
FIGS. 8A-8C shows DMN-SN ROI-to-ROI network connectivity.
Figure 8B:
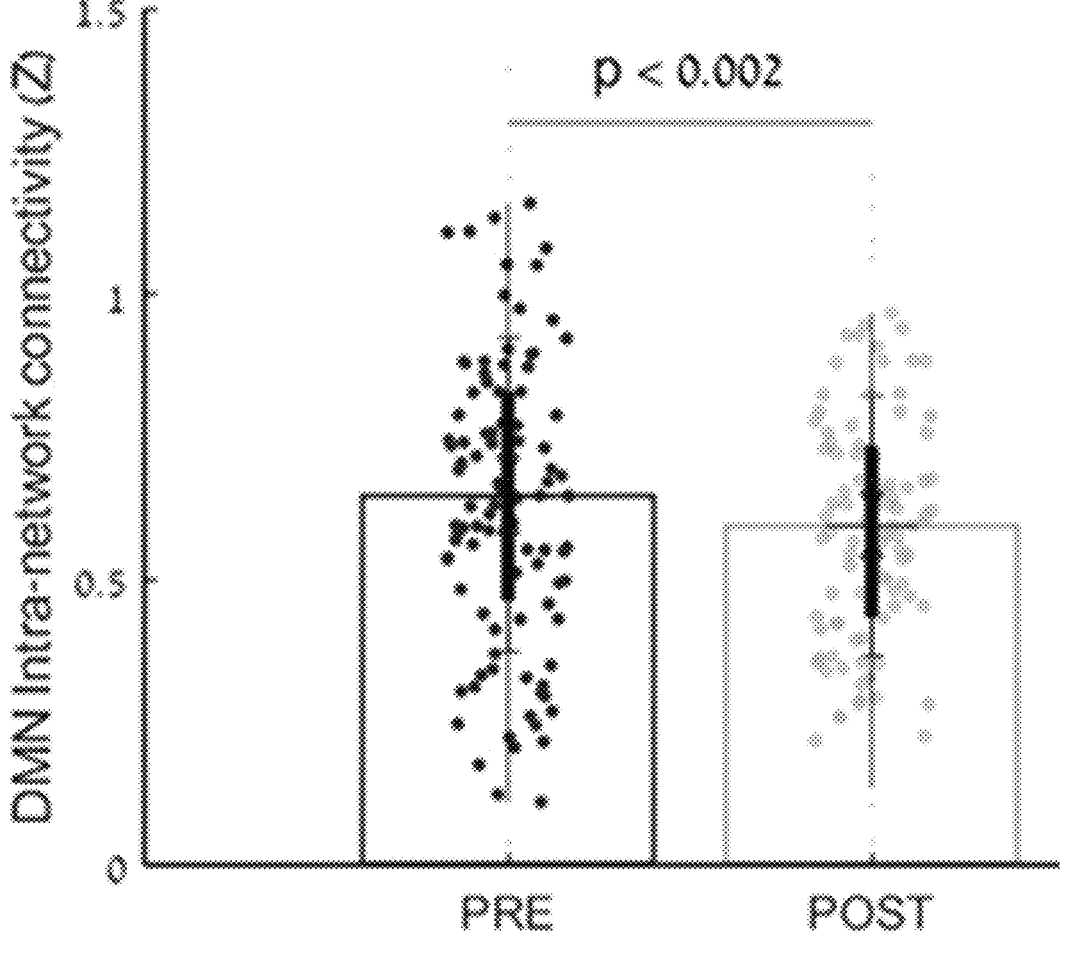
Figure 8C:
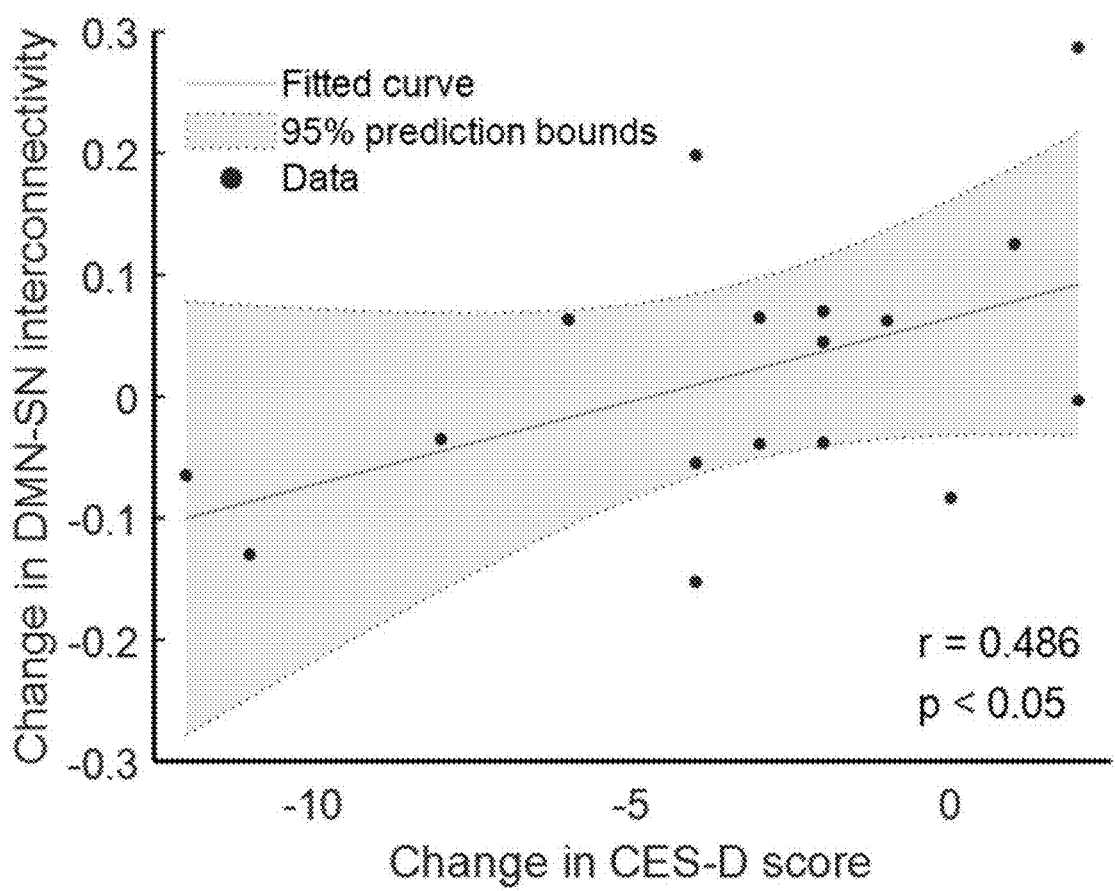

Seed-to-voxel based analysis revealed a significantly increased post-training rsFC between left and right hippocampal and parahippocampal areas within the medial temporal lobe (MTL), and the frontoparietal and the DMN networks (FIGS. 8B-8C).

Figure 4A:
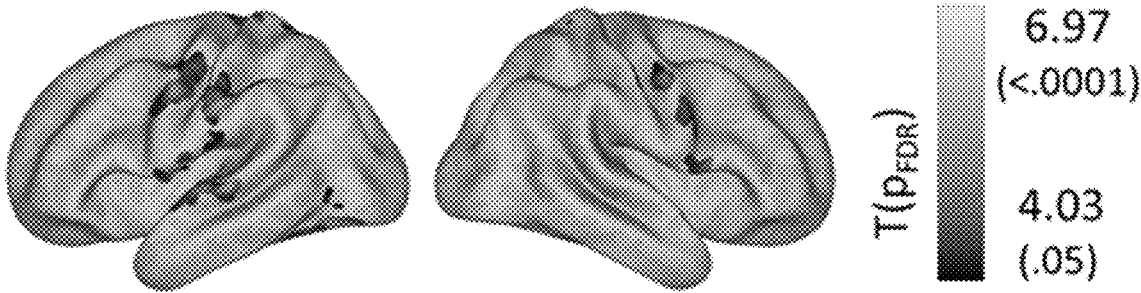
FIGS. 4A-4C shows seed-to-voxel connectivity maps of longitudinal differences.
Figure 4B:
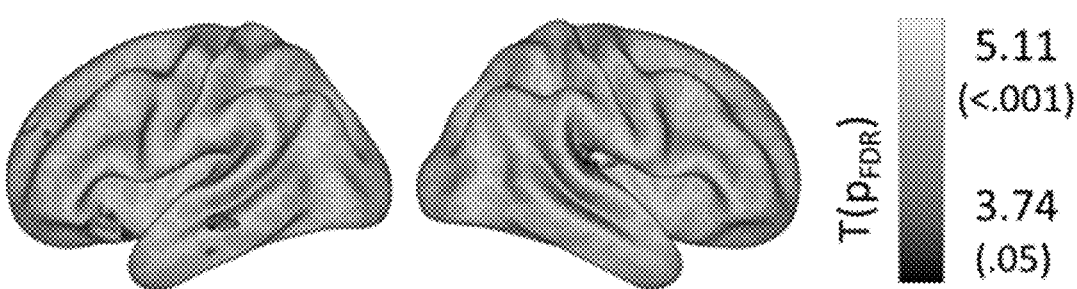

Most significant increases were demonstrated between the left hippocampus and the and posterior cingulate cortex (PCC, BA31_R, k=328, $P_{FDR}$<0.0001), inferior parietal cortex, IPC (BA40, k=305, $P_{FDR}$<0.0001) and posterior parietal cortex (BA5, k=356, $P_{FDR}$<0.0001) rsFC (FIG. 4A). Significant increases were demonstrated between the left parahippocampal area and the dorsal prefrontal cortex (PFC, BA9_L) rsFC (k=176, $P_{FDR}$=0.027). The right parahippocampal and the anterior prefrontal cortex and dorsal anterior cingulate cortex (dACC) rsFC (BA10_R, BA32_L; k=98, $P_{FDR}$=0.010, k=158, P=0.005 respectively) (FIG. 4B). Importantly, this increase was correlated with maze-solving performance (r=0.508, P=0.037), demonstrating the dynamic learning process (FIG. 4C).

Figure 4C:
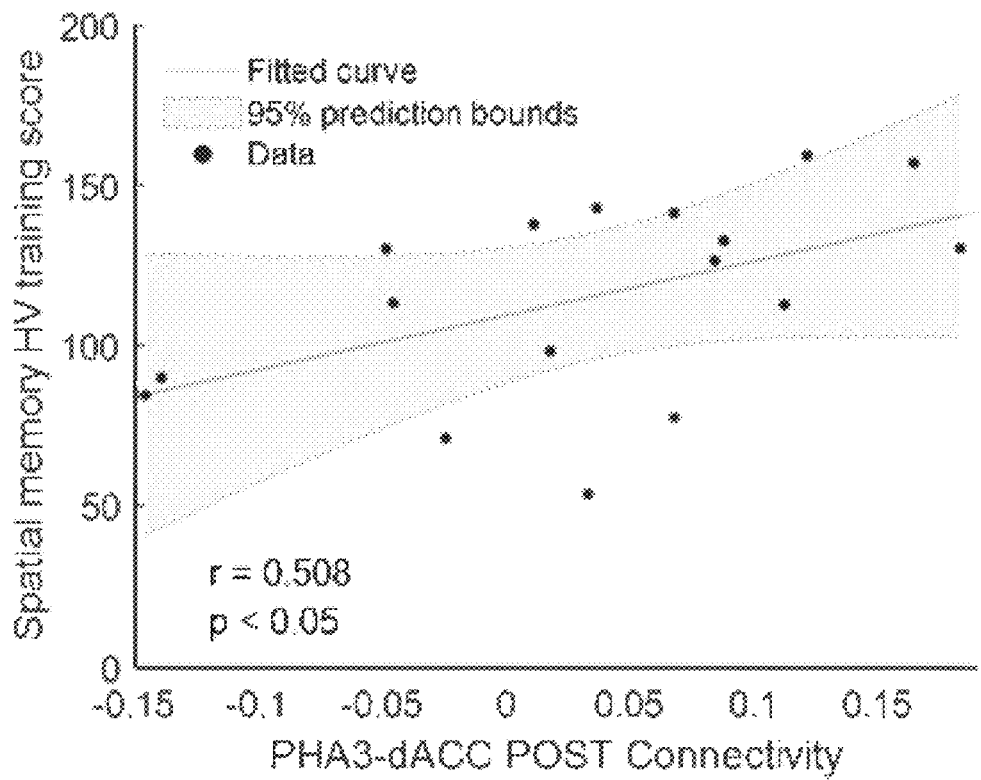

FIGS. 4A-4C shows seed connectivity maps of longitudinal differences. FIG. 4A shows seed: left hippocampus, FIG. 4B shows seed: right parahippocampus (POST>PRE-intervention of the resting state brain imaging data—group level. ADD n=17 to ALL figs etc. and descriptions and explanations), P<0.05, FDR corrected, parametric stats, two sided. FIG. 4C shows correlation between the changes in training score and increased PHA3-dACC post training connectivity. Parahippocampus, PHA, dorsal anterior cingulate cortex, dACC. Regarding FIGS. 4A-4C and FIG. 6 the interventions of the invention show Significantly increased post-training connectivity was found between hippocampal and parahippocampal areas and the frontoparietal network including executive working memory frontal areas (BA9, BA10), and the anterior and posterior cingulate cortex (PCC, BA31, ACC, BA32) within the DMN. Furthermore, there is significant correlation between changes in training score and brain post intervention connectivity in the MTL-Fronto parietal network. The Training score is the final Maze APP level/Total training time (Hours).

Results showed significantly improved post-training connectivity in allocentric and egocentric navigation brain areas, and between the insular cortex and these brain areas, reflecting healthier connectivity.

The intervention increased rsFC of areas correlated with ego-and-allo-centric navigation.

As the RSC integrates both egocentric and allocentric spatial information streams, there was demonstrated increased connectivity in this key area following the treatment. RsFC between the right RSC seed and right parietal cortex was increased (k=211, PFDR=0.0017), contributing to the egocentric navigation performance. Additionally, increased rsFC was demonstrated in the right anterior prefrontal cortex (BA10, k=175, $P_{FDR}$=0.0038), contributing to the allocentric navigation performance.

Figure 5A:
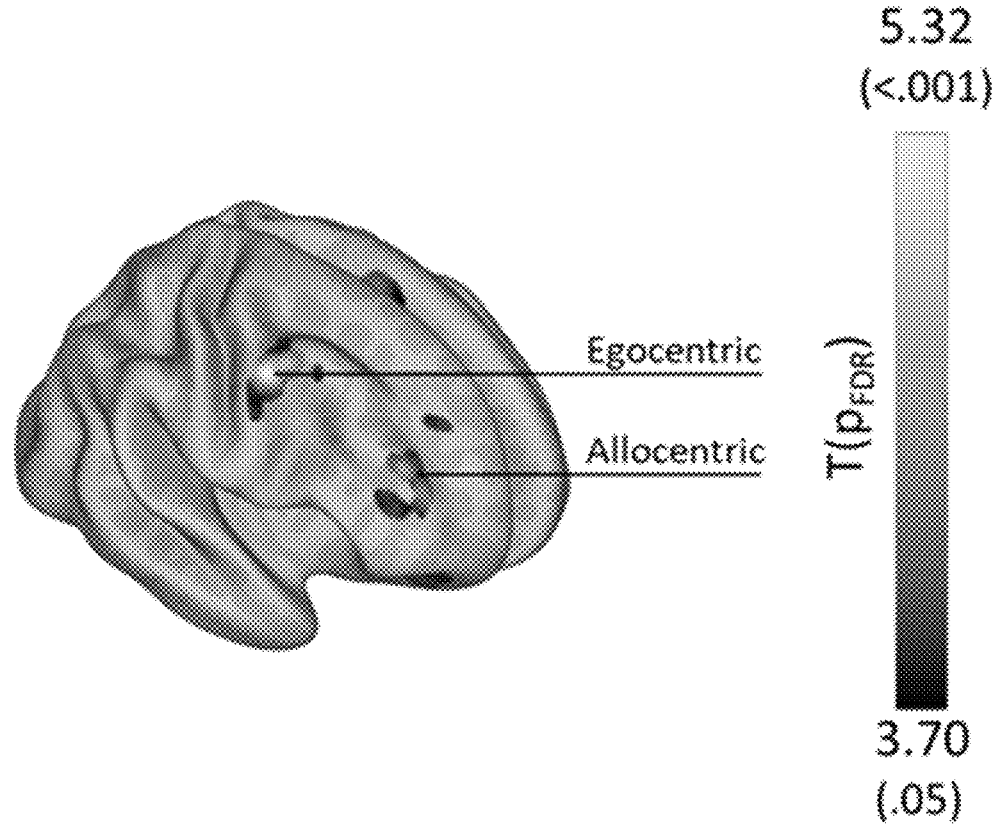
FIGS. 5A-5B shows seed-to-voxel connectivity maps of longitudinal differences.
Figure 5B:
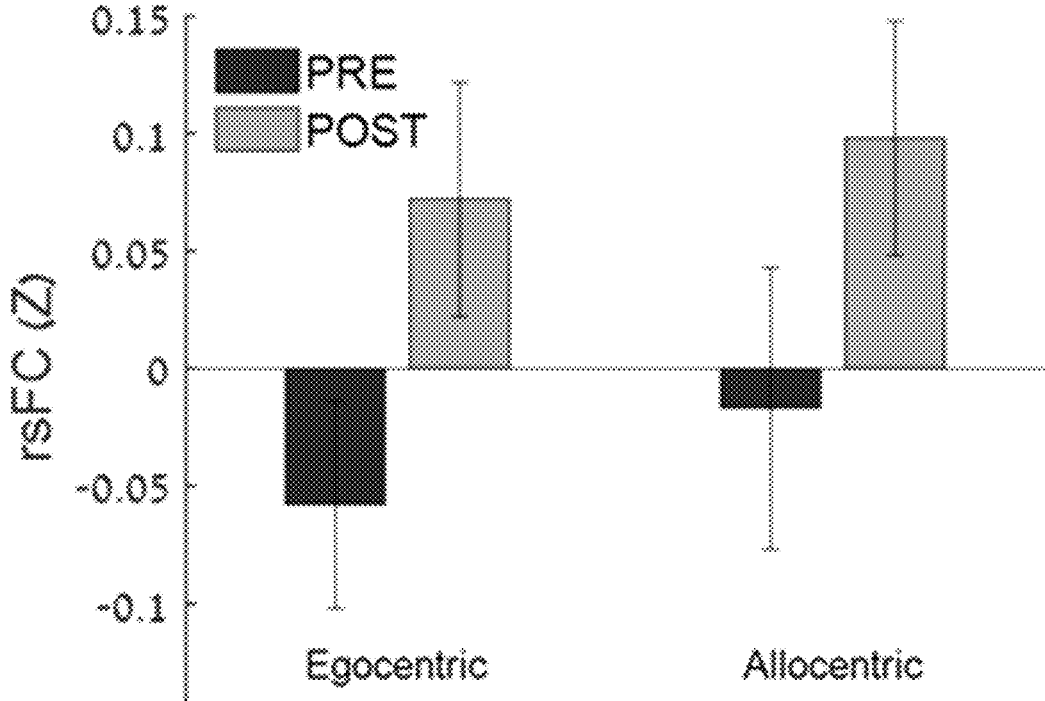

FIGS. 5A-5B shows seed-to-voxel connectivity maps of longitudinal differences. The retro splenial complex (RSC) integrates both egocentric and allocentric spatial information streams. Improved post-trinng rsFC was found in both egocentric and allocentric networks (k=211, $P_{FDR}$<0.002 and k=175, $P_{FDR}$<0.004 respectively) Seed: right RSC, (POST>PRE-intervention), parametric stats, two sided. Bar graphs of cluster Fisher's Z effect size connectivity values, error bars, CI. The intervention group shows significantly improved post-training connectivity within the Egocentric navigation network (RSC and Fronto parietal memory and executive network). The RSC is a key area connecting the egocentric and allocentric spatial memory network (P<0.05, FDR corrected).

The intervention increased rsFC between spatial navigation networks and the insula.

Seed-to-voxel based functional connectivity analysis revealed a significantly increased post-training rsFC between spatial navigation networks and the granular insular cortex seed (FIG. 6) Significant increases were demonstrated in the egocentric network key areas: precuneus (BA7, k=1172, $P_{FDR}$<0.0001), lingual gyrus (BA19, k=630, $P_{FDR}$<0.0001), and fusiform gyrus (BA37, k=111, $P_{FDR}$=0.017), and allocentric network key areas: medial prefrontal cortex, mPFC (BA32, k=101, $P_{FDR}$=0.01). These results may be linked to increased multisensory stimulus attention and self-awareness process. The results might also suggest the synergetic psychological and cognitive intervention increase the connectivity between areas that are dedicated to spatial and verbal memory (and are most tightly linked to age related degeneration) and limbic system structures such as the insula.

Figure 6:
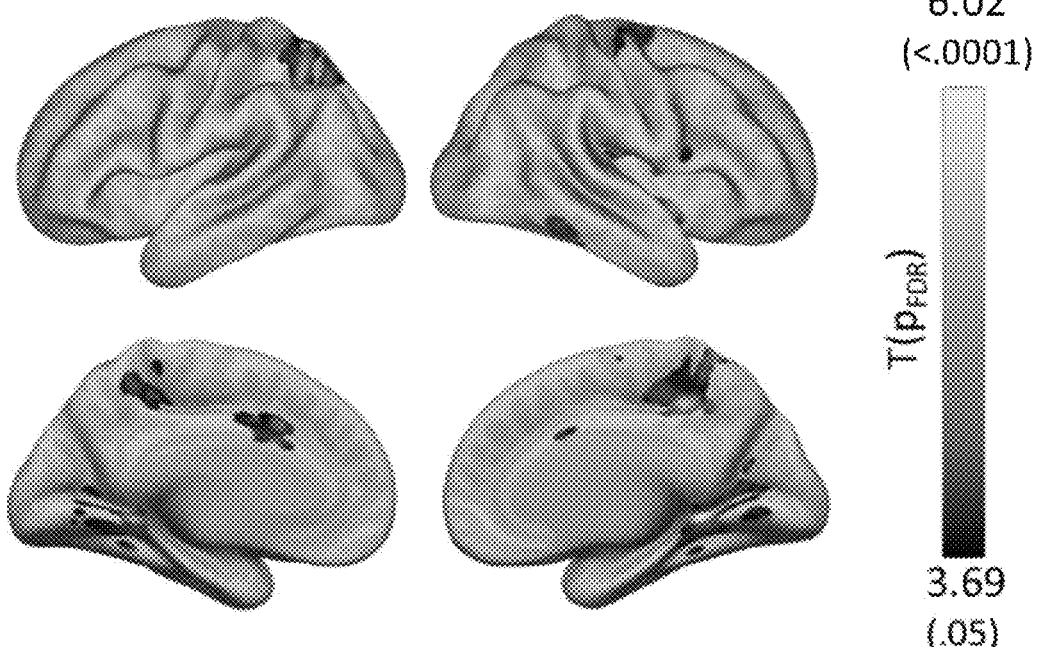
FIG. 6 shows seed-to-voxel connectivity maps of longitudinal differences. Increased post-training rsFC between spatial navigation networks and the left granular insular cortex seed (POST>PRE-intervention of the resting state brain imaging data—group level, n=17, $P_{FDR}$<0.05, parametric stats, two sided).

FIG. 6 shows seed-to-voxel connectivity maps of longitudinal differences. Increased post-training rsFC between spatial navigation networks and the insula. Seed: the left granular insular cortex. (POST>PRE-intervention), p<0.05, FDR corrected, parametric stats, two sided.

Post-training evaluation showed significant improvement in depression scores and a trend of improvement in anxiety scores (p=0.004 and 0.06 respectively).

The intervention significantly decreased self-reported depression. Following the intervention, CES-D (depression scale) score was reduced by 26.6% with a large effect size (d=-0.829, p=0.004). A trend toward improvement in the anxiety score (GAD7) was shown (p=0.063, d=-0.484).

FIG. 7A shows CES-D score changes. The intervention significantly decreased self-reported depression CES-D questionnaire. Following the intervention, CES-D (depression scale) score was reduced by 26.6% with a large effect size (d=-0.829, p=0.004). Data are presented in mean±SEM, P-value, paired student's t-test analysis. FIG. 7B shows significant reduction in depression score (CES-D) in the digital therapy intervention group (Remepy) vs. control group.

In depression, there is often increased activity and connectivity within the DMN and the salience network (SN). The study's analysis showed reduced DMN intra-network connectivity (p=0.002), and significant correlation was found between the changes in depression score and improved inter-network connectivity between the DMN and the SN (r=0.486, p=0.048), reflecting a healthier connectivity pattern.

The intervention improves DMN and SN networks interplay: The ROI-to-ROI analysis revealed decreased post-intervention intra-network connectivity (z-score: 0.64±0.28 to 0.59±0.23, P=0.002) within the DMN. No significant change was found within the SN (z-score: 0.62±0.27 to 0.60±0.27, P=0.169) (FIG. 8C). No significant internetwork was found (z-score: -0.165±0.22 to -0.160±0.21, P=0.126), however, a significant correlation was found between changes in internetwork rsFC and changes in CES-D score (r=0.486, P=0.048) following treatment, demonstrating that improvement in depression score is correlated with increased internetwork anticorrelation.

FIGS. 8A-8C shows DMN-SN ROI-to-ROI network connectivity. FIG. 8A shows the default mode network (DMN), and salience network (SN) are anticorrelated in the healthy non-depressed brain. Intra-network connections and internetwork connections are presented as lines. FIG. 8B shows the improved CES-D depression score (negative change mark improvement in the depression state for the post vs. pre assessment) was correlated with increased negative internetwork DMN-SN rsFC. This suggest correlation between how much individuals subjects improved in the depression and how much their connectivity pattern is healthier (i.e. reflect more anti-correlation between DMN and SN (as in depressed subjects this anticorrelation is lost).

The results of the study highlight the synergistic effect between the unique cognitive training and psychological interventions employed as part of the study.

DMN connectivity has been previously linked to psychological processes that influence inflammation, such as stress, anxiety, and depression, and some components of the DMN are known to regulate peripheral pathways moderating inflammation.

The study results also showed increased connectivity between the insular cortex and both egocentric and allocentric navigation networks following training.

Example 2

Follow-Up Study—"Study B" (Interim Analysis) for SCD Follow-Up Study—Study B (Interim Analysis)

A follow up study was conducted in adults with increased stress levels and SCD, with 102 participants who were randomized to either intervention or a waitlist control group. The intervention group followed a daily digital treatment protocol of 30 minutes during 3 weeks. The treatment protocol consisted of a modified combined intervention with more emphasis on stress-reducing psychological modules, in addition to the multisensory maze navigation training described above.

Participants were evaluated at baseline and post-intervention using psychological questionnaires, immune system biomarkers and fMRI. The intervention group was further evaluated 3 weeks post-intervention.

Figure 10A:
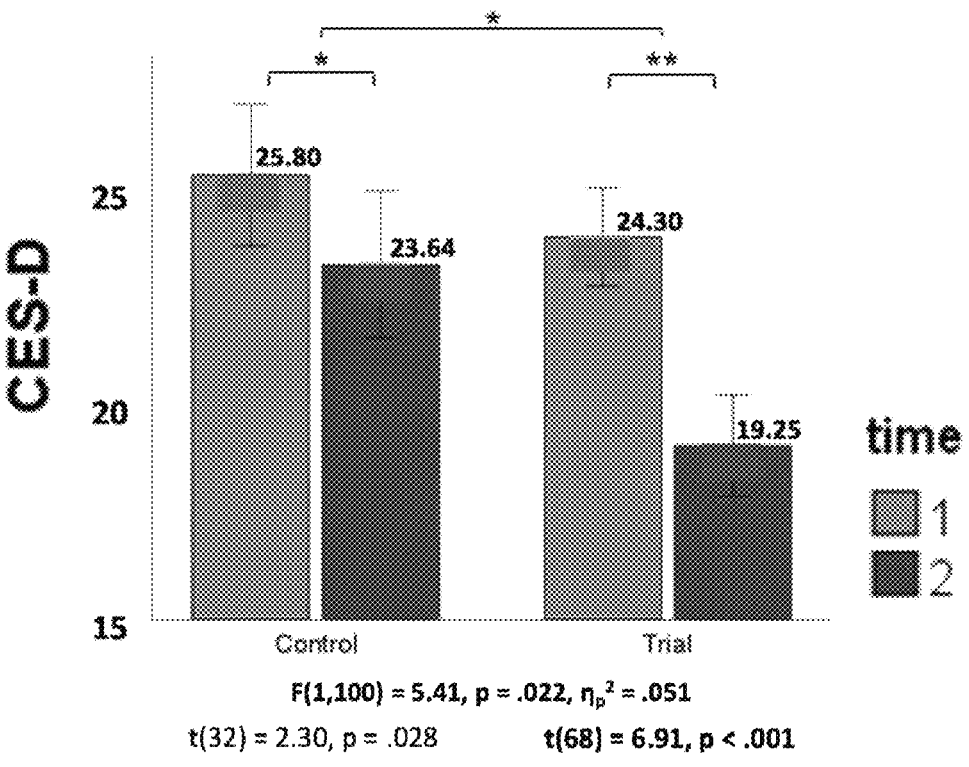
FIGS. 10A-10F shows results of psychological questionnaires: significantly improvement of scores of depression (CES-D, p=0.22, see FIG. 10A), stress/anxiety (STAI-S, p=0.028, see FIG. 10B), resilience (BRCS, p=0.025, see FIG. 10C) and emotional well-being (MHC-SF, p=0.043, see FIG. 10D), and marginally significant improvement of additional measures of stress and anxiety (PSS, see FIG. 10E, STAI-T, see FIG. 10F), in the intervention group compared with the control group.
Figure 10B:
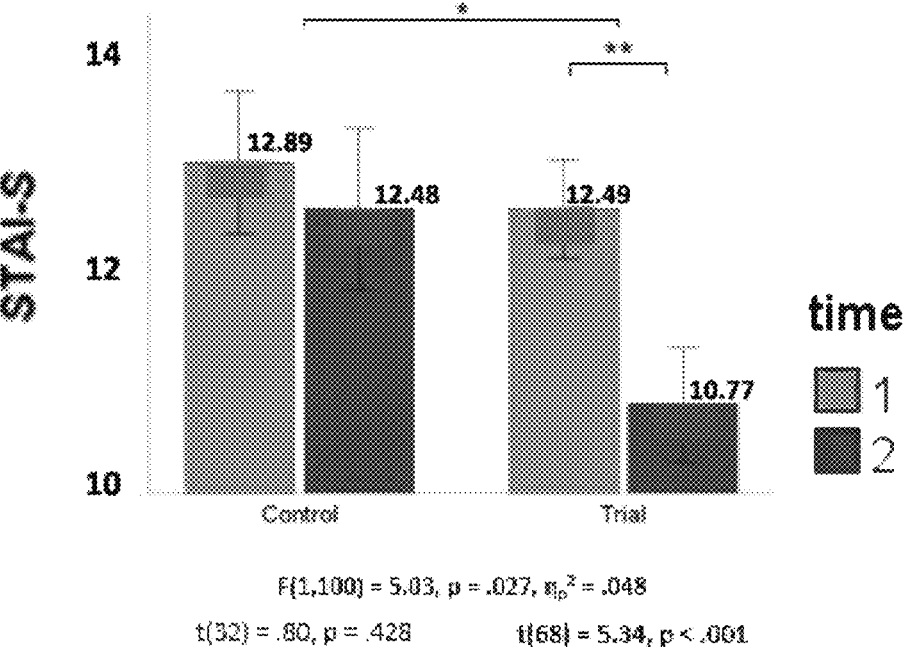
Figure 10C:
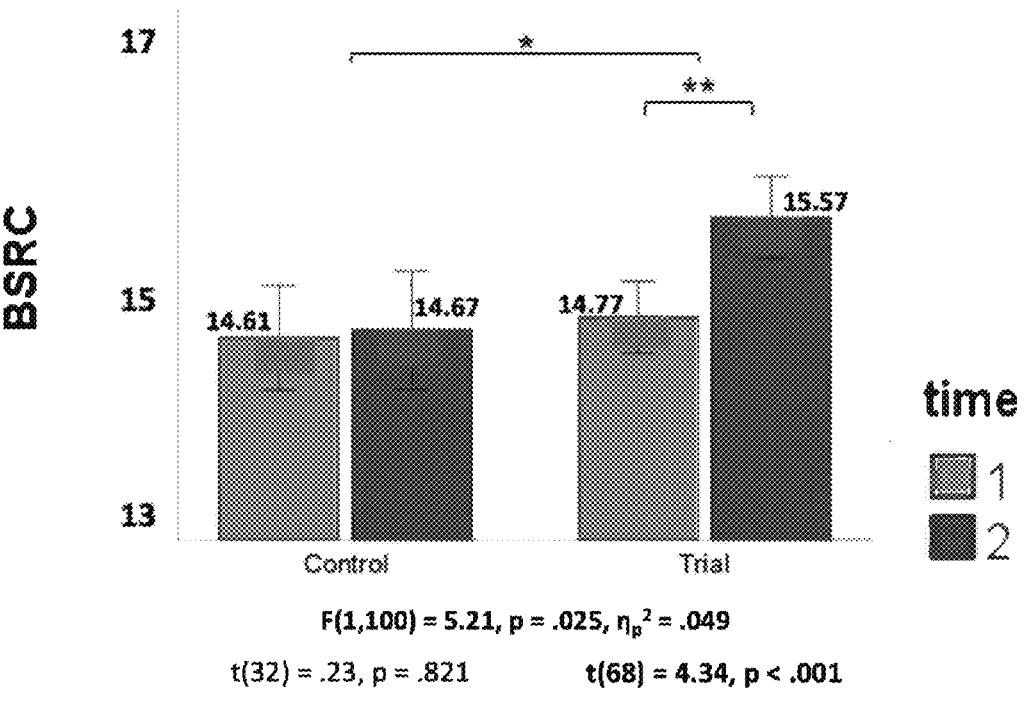
Figure 10D:
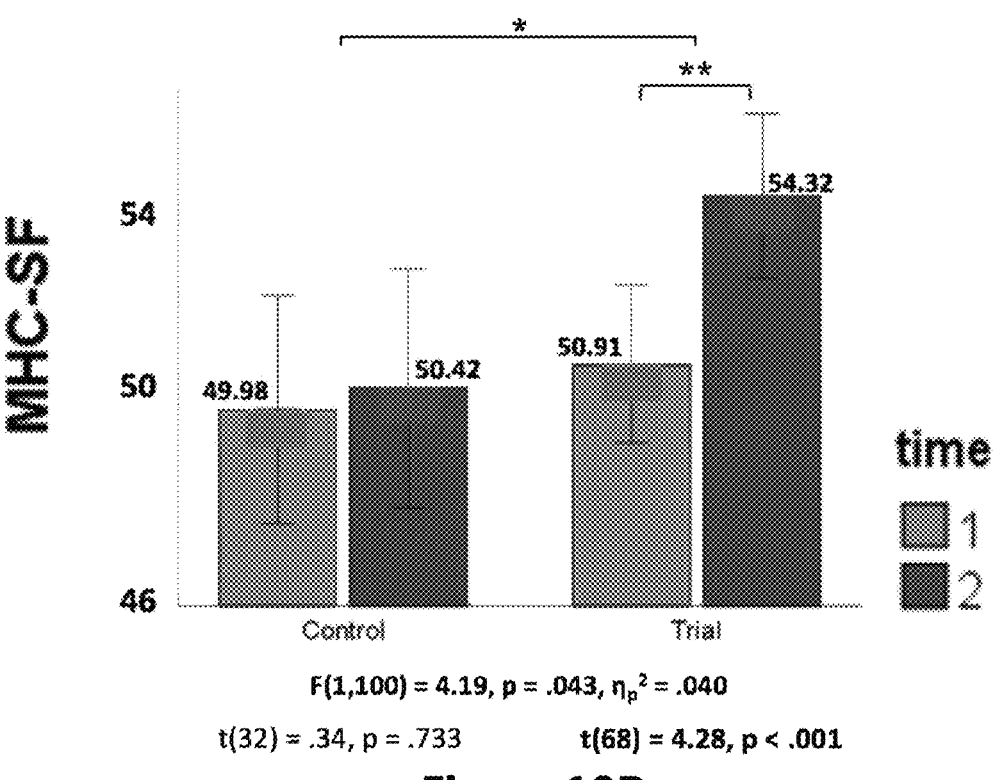
Figure 10E:
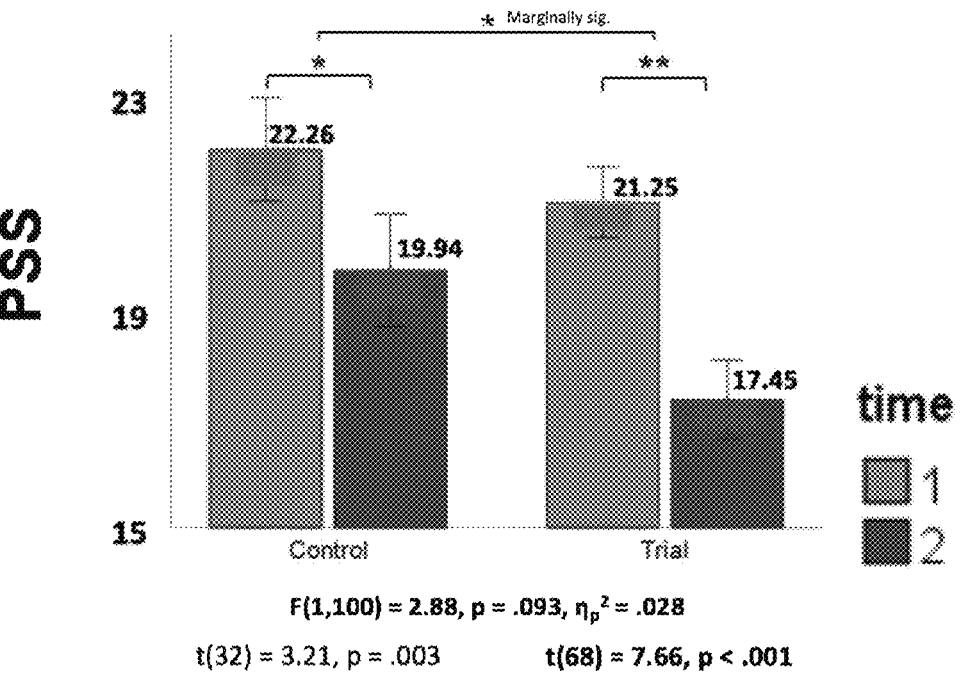
Figure 10F:
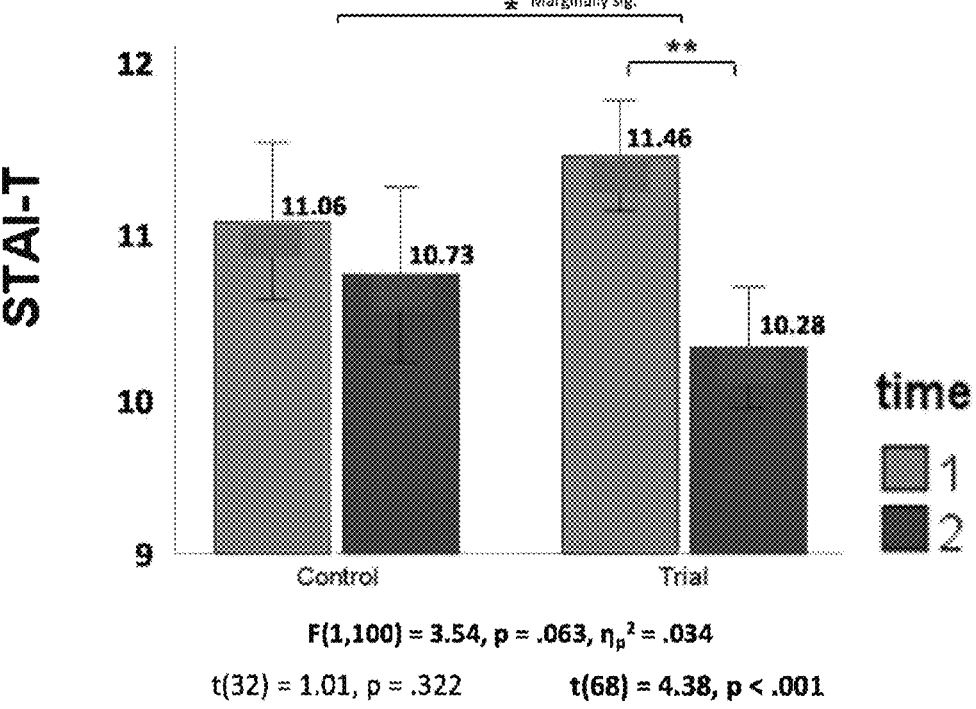
Figure 11A:
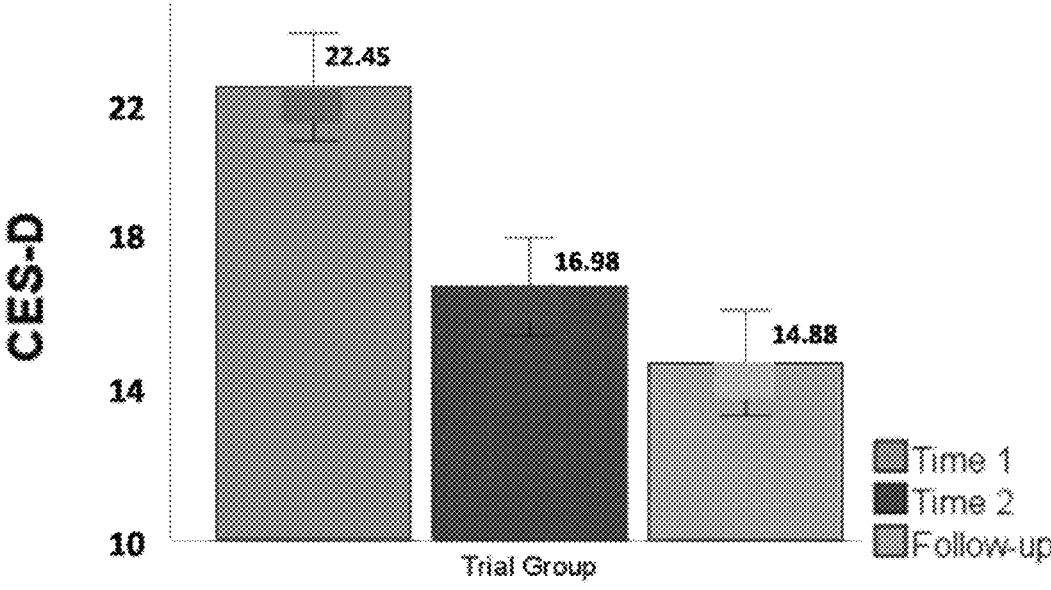
FIGS. 11A-11F shows bar charts recording the improvement in questionnaire scores preserved or even further improved in the intervention group when evaluated 3 weeks following the end of the daily use of the mobile application, emphasizing the lasting effect of the intervention. Charts are presented for scores of depression (CES-D, FIG. 11A), stress/anxiety (STAI-S, FIG. 11B), resilience (BRCS, FIG. 11C) and emotional well-being (MHC-SF, FIG. 11D), and improvements of additional measures of stress and anxiety (PSS, FIG. 11E, and STAI-T, FIG. 11F).
Figure 11B:
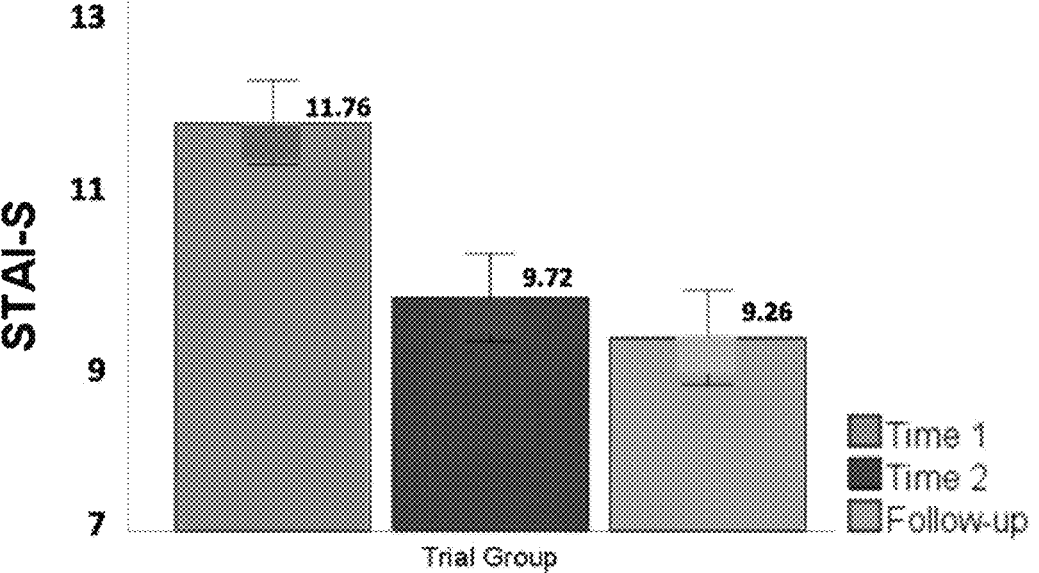
Figure 11C:
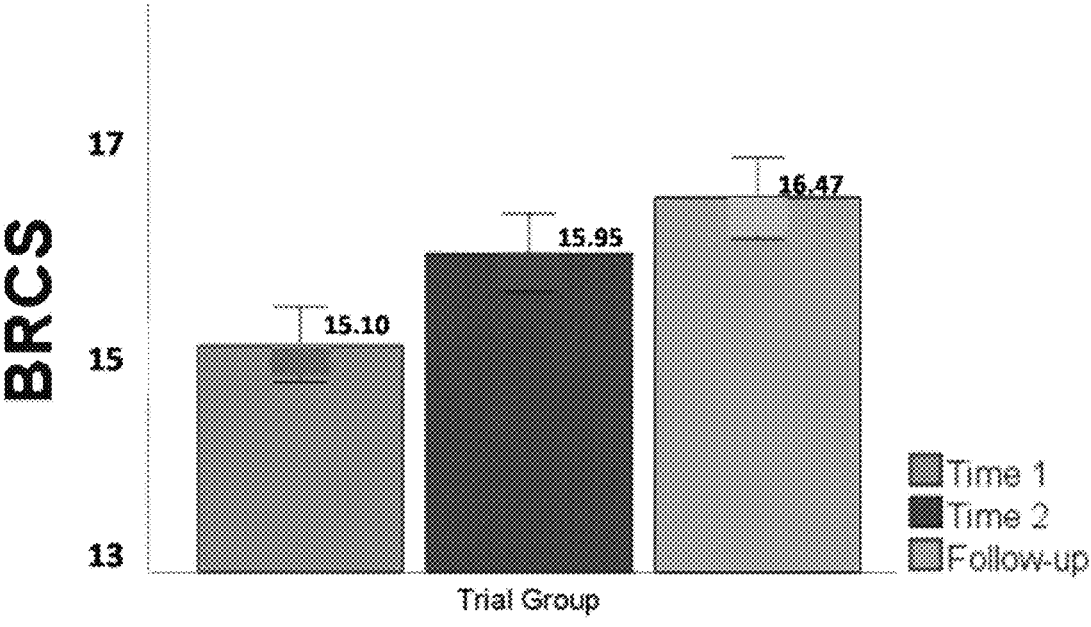
Figure 11D:
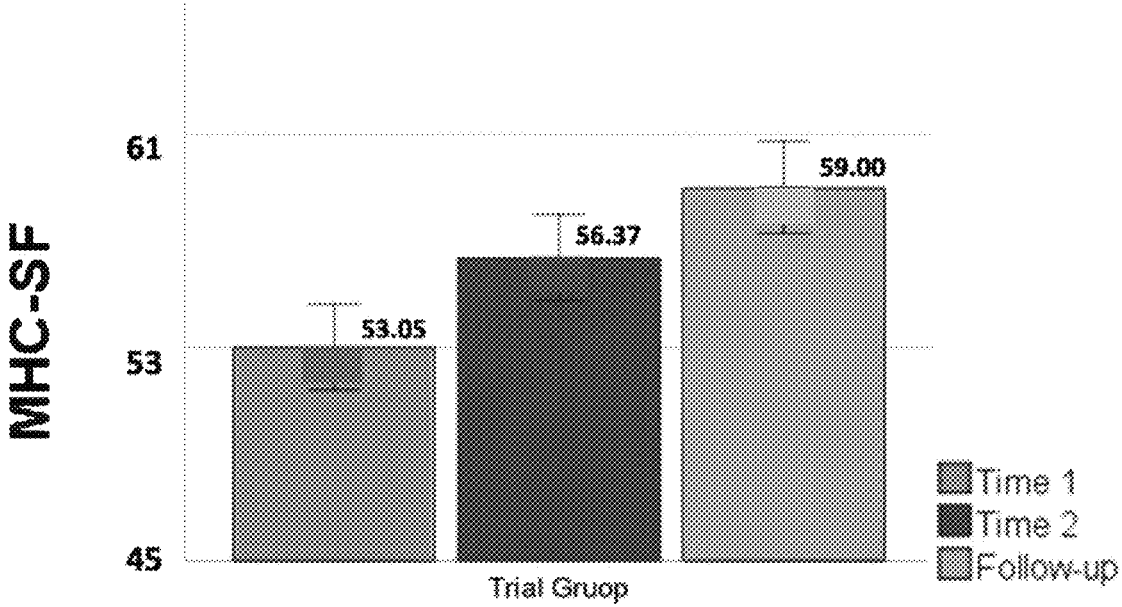
Figure 11E:
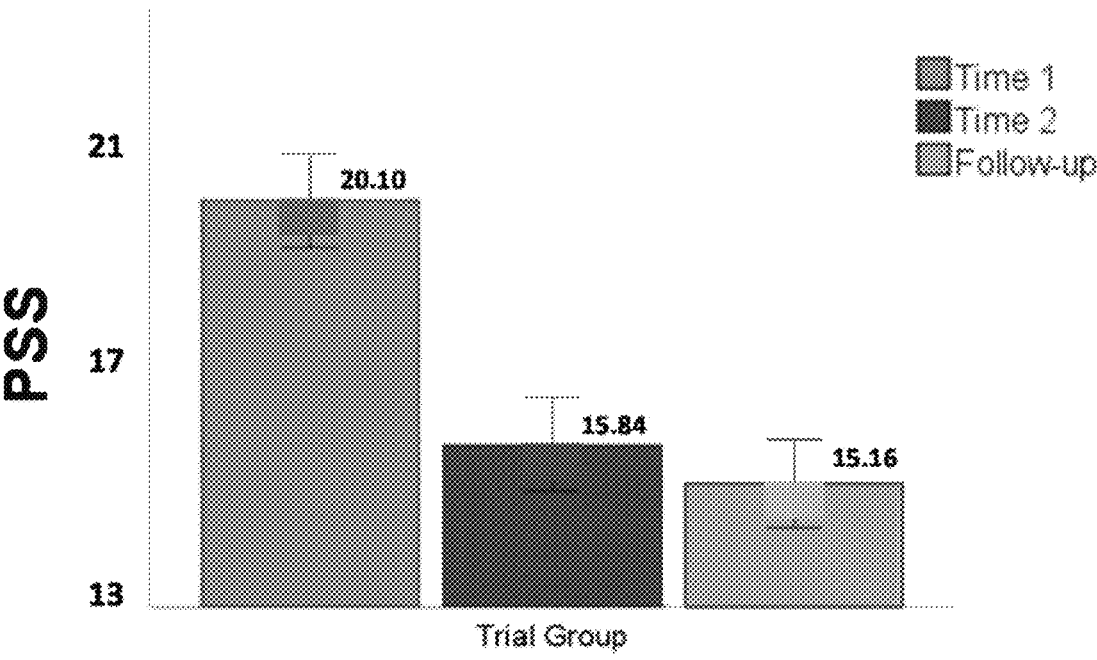
Figure 11F:
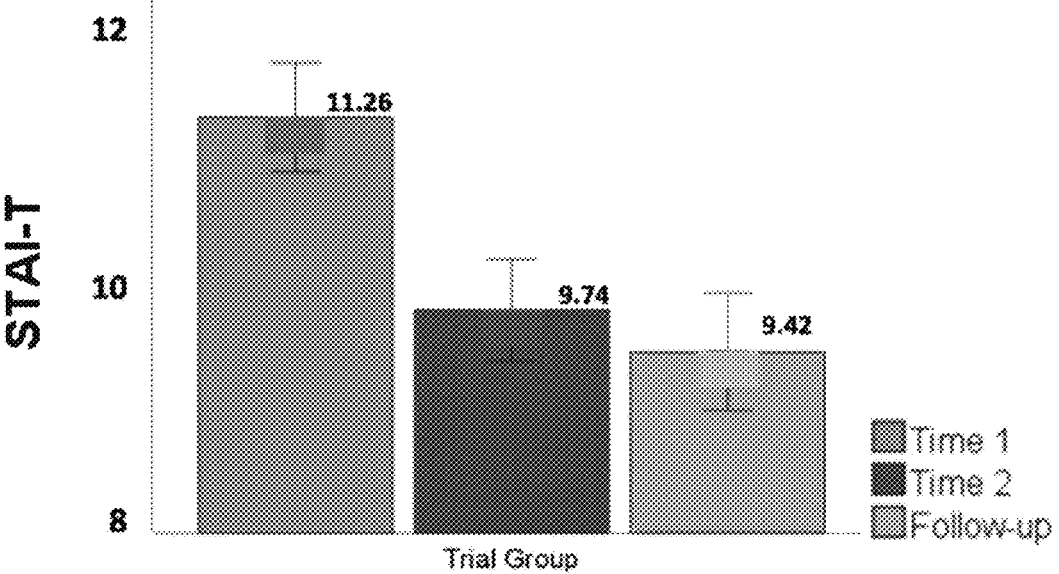

Results of psychological questionnaires show significantly improvement of scores of depression (CES-D, p=0.22, see FIG. 10A), stress/anxiety (STAI-S, p=0.028, see FIG. 10B), resilience (BRCS, p=0.025, see FIG. 10C) and emotional well-being (MHC-SF, p=0.043, see FIG. 10D), and marginally significant improvement of additional measures of stress and anxiety (PSS, see FIG. 10E, STAI-T, see FIG. 10F), in the intervention group compared with the control group.

The improvement in questionnaire scores was preserved or even further improved in the intervention group when evaluated 3 weeks following the end of the daily use of the mobile application, emphasizing the lasting effect of the intervention. FIGS. 11A-11F shows bar charts recording the improvement in questionnaire scores preserved or even further improved in the intervention group when evaluated 3 weeks following the end of the daily use of the mobile application, emphasizing the lasting effect of the intervention. A subgroup of participants from both intervention and control groups were assessed via rsfMRI at baseline and post-intervention to evaluate brain networks connectivity.

Neural and Behavioral Correlates of Training Aging Population Suffering from Subjective Cognitive Decline with a Novel Digital Spatial Memory and Digital Psychological Intervention The present example of digital training in both egocentric and allocentric navigation uses a protocol that shows enhanced brain plasticity—namely—using gradual blindfolding and enriched multisensory environments for navigation. The present example evaluated a comprehensive digital psycho-cognitive multisensory training's impact, focusing on behavior and resting-state functional connectivity (rsFC) in individuals with subjective cognitive decline (SCD). Participants engaged in a two-week intervention of daily half-hour digital navigation training sessions, featuring a specially tailored (with both allocentric (map based) and egocentric (person body point-of-view centered cues)) digital version of Hebb Williams (HW) based mazes, audiovisual navigation cues, gradual blindfolding protocol, and stress reduction psychological interventions. Study endpoints encompass brain rsFC, psychological well-being and depression standardized questionnaires, HW maze performance scores, and correlations between the various endpoint measures.

Key results include: (1) Significantly reduced clinical CES-D depression scores (27% average reduction), which were correlated with improved negative inter-network connectivity between the DMN (default mode network) and SN (salience network) and reduced inter-network connectivity within the DMN. Both these changes are consistent with patterns observed in the literature for brain states exhibiting less clinically depression symptoms. (2) Enhanced connectivity was found between middle temporal lobe (MTL) areas, particularly the hippocampus, and executive working memory frontal regions. This connectivity improvement was significantly correlated with enhanced spatial cognition performance (3) Significant increases in rsFC between egocentric and allocentric navigational areas and the insular cortex. The hippocampus and MTL are the structures that are most affected by aging and in Alzheimer's Disease (AD) and the above-mentioned changes following the training characterize brains that are less aged, or clinically less affected by memory loss. These findings suggest that the combined and unique psycho-cognitive intervention and spatial memory blindfolding method resulted in key changes to spatial memory, spatial cognition and emotional modulation areas and show key relevant correlations between behavioral changes and brain connectivity.

Study Highlights:

A stronger anti-correlation between DMN-SN connectivity post intervention was observed, indicating an improvement in mood regulation through better brain network functioning.

Improved CES-D depression scores post intervention were significantly correlated with the above-mentioned brain connectivity pattern.

Blindfolding spatial memory training protocol enhances functional connectivity in brain areas susceptible to aging and brain connectivity degeneration.

Improved spatial cognition performance is correlated with improved memory network connectivity including middle temporal lobe (MTL) and egocentric navigation areas.

Multisensory psycho-cognitive digital training positively affects the connectivity within spatial memory MTL and frontal executive-related networks.

Improved spatial memory Hebb-Williams (HW) multisensory and blindfold training scores correlated with connectivity enhancement of both allocentric and egocentric navigation-related brain areas.

A longitudinal study was conducted to assess the impact of a combined digital psycho-cognitive multisensory training on behavior and rsFC in aging individuals experiencing subjective cognitive decline (SCD). Additionally, correlations between the observed changes in rsFC and behavior were observed.

Brain regions supporting spatial and verbal cognition are susceptible to early damage during aging and neurodegenerative diseases. Egocentric and allocentric digital navigation training (sighted and blindfolded) is shown to improve brain plasticity. Neuroinflammation and chronic stress are crucial factors in brain degeneration during aging, MCI, and AD progression. Psychological interventions reduce inflammation and slows down neurodegenerative diseases. Multisensory psycho-cognitive digital training improves brain plasticity through, at least, a synergistic effect.

Trial Design

A pilot study, designed as a prospective, open-label trial, was undertaken at the Baruch Ivcher Institute for Brain, Cognition & Technology (BCT) within the School of Psychology at Reichman University, Israel. The study recruited healthy adults aged between 55 and 60 who exhibited signs of subjective cognitive decline (SCD), demonstrated a Montreal Cognitive Assessment (MoCA) score of 24 or higher, and scored 5 or above on the Perceived Stress Scale (PSS-10). Exclusion criteria included: any history of malignancy, traumatic brain injury, brain surgery, chronic subdural hemorrhages, epilepsy and other neurodegenerative diseases, any psychiatric disorder or pathological cognitive decline, and MRI contraindications. After signing an informed consent, participants were engaged in a two-week digital intervention using a mobile application, with supervised sessions on days 1, 7, and 14, supplemented by daily self-training at home. Participants were assessed for changes in the brain functional and structural connectivity, the MoCA cognitive assessment, well-being and psychological state. The study was approved by IDC Institutional Review Board (IRB) (No. P_2023138). The neuroimaging study protocol was reviewed and approved by the IRB of Sheba Medical Center (No. 8591-21-SMC). All participants signed an informed consent prior to their inclusion. All research was performed according to the relevant guidelines and regulations.

The Digital Intervention

The participants utilized a comprehensive training mobile application developed by Remepy (https://www.remepy.com), which incorporates unique methodologies based on, among other things, using digital mazes (similar to Hebb-Williams mazes). The virtual navigation training protocol employs an innovative, integrative approach to spatial memory and navigation training, designed to accelerate the learning process and induce sensory and cognitive network balance. The unique approach embedded in Remepy's app combines both egocentric and allocentric navigation strategies through a three-step blindfold training protocol, with progressively increasing navigation complexity: each new maze trial starts with a top view map of the maze followed by a sighted virtual 3D navigation experience. In the next step, navigation becomes more challenging as 50% of the maze is randomly masked, and in the final step, participants are asked to navigate the maze blindfolded, relying on spatial memory and auditory cues to convey crucial spatial information (FIGS. 17A-17E). While the main task was successful wayfinding, participants were instructed to find the fastest route to the exit while avoiding collisions with the walls.

The distance audio algorithm utilizes a sound frequency conversion where a higher frequency indicates proximity to a nearby wall, while a lower frequency signifies greater distance from the wall. Footstep sounds signal a clear passage. Participants guided their way by swiping their fingers across the touchscreen in 45-degree directions. The software automatically logged errors, time, and performance for each session.

Maze-solving performance value was calculated for each participant as the final maze level achieved, divided by the total training time. The training protocol scheme is provided in.

The application also included stress regulation techniques drawn from mindfulness, attention-focusing exercises, and cognitive behavioral therapy, delivered through video, audio, and interactive formats. Daily self-training lasted around 30 minutes and involved 20 minutes of navigation program engagement and 5-10 minutes of psychological training (FIG. 17E).

Figures 17A, 17B, 17C, 17D, 17E:
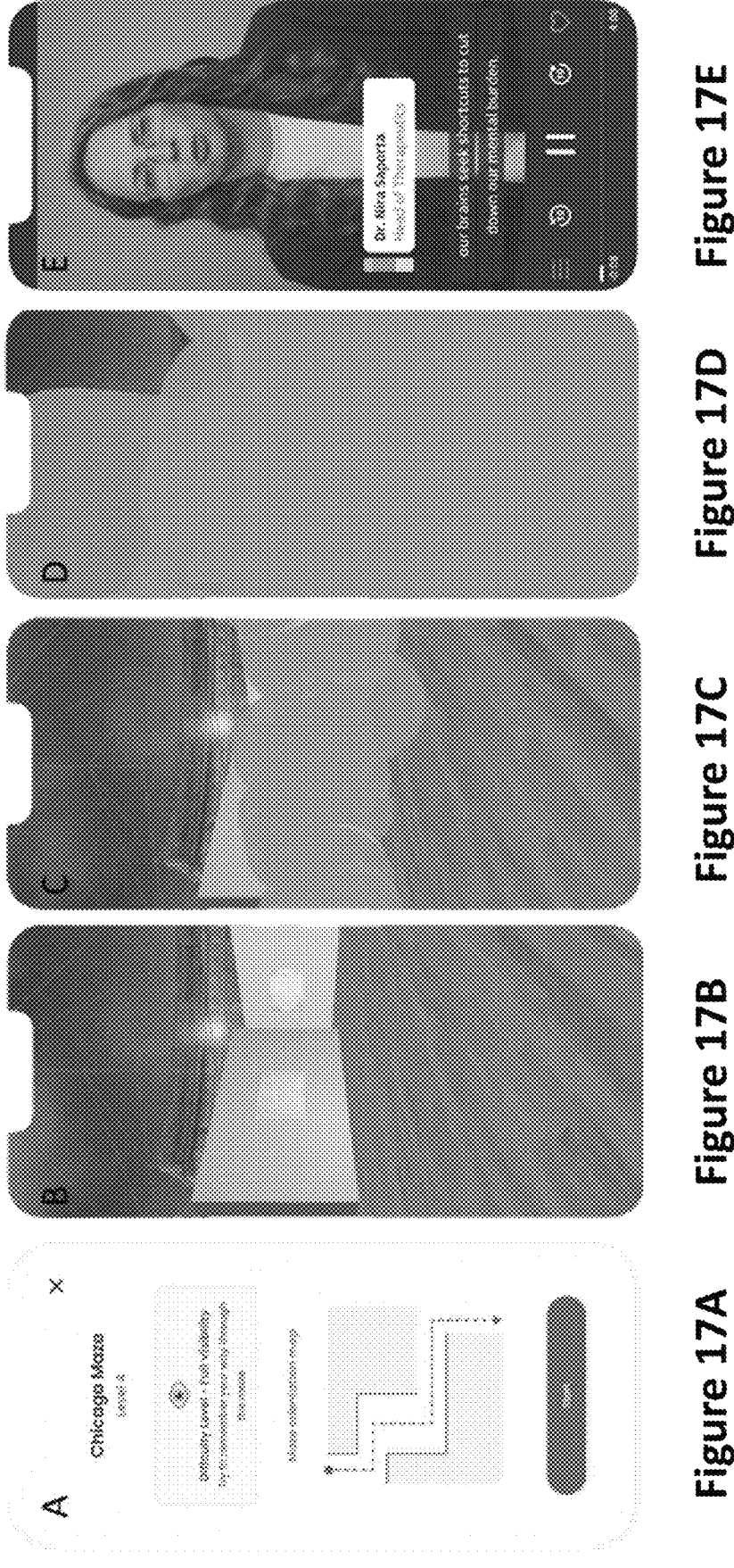
FIGS. 17A-17E shows screen shots from the digital therapy intervention application on a mobile computation device.

FIGS. 17A-17E demonstrates the Remepy APP comprehensive training mobile application. A top view map of HW maze used (FIG. 17A). Note, the app utilizes a special version of the digital maze which includes both an allocentric view that was introduced visually (FIG. 17A), and a digital 3D egocentric navigation view with visual and auditory input (FIG. 17B). This way subjects were encouraged to integrate both map-based allocentric navigation and egocentric navigation; 50% random screening masked—reducing half of the visual cues and encouraging subjects to integrate visual cues with the auditory cue (FIG. 17C); blindfolded navigation in which no visual cues were available (FIG. 17D); psychological interventions—video and audio aimed at chronic stress reduction, CBT, etc. (FIG. 17E).

Outcome Measures

Montreal Cognitive Assessment (MoCA)

The MoCA is a brief cognitive screening tool with high sensitivity and specificity for detecting MCI in patients. The maximum MoCA score is 30 points, with a 1-point scoring correction for individuals with 12 years of education or less. A score of 26 or above is considered normal and a score lower than 26 has been considered to be the optimal cutoff point for diagnosis of cognitive impairment.

Self-Reported Questionnaires

Changes in the subject's psychological state were assessed using the Mental Health Continuum Short Form (MHC-SF), General Anxiety Disorder-7 (GAD-7D), Center for Epidemiologic Studies Depression Scale (CES-D), and the 36-Item Short Form Survey (SF-36) validated questionnaires. These questionnaires were administered 3 times during the study (Days 0, 7, 14).

Brain Imaging

Brain imaging MRI scans were performed on MAGNETOM Prisma 3T Scanner, configured with a 64-channel receiver head coils (Siemens Healthcare, Erlangen, Germany), at the Ruth and Meir Rosental Brain Imaging Center (MRI), Reichman University. The MRI protocol included the following sequences: Two runs of 300 volumes (9:28 min) resting state fMRI scans were acquired using a multiband echo planar imaging sequence, CMRR EPI 2D. Scan parameters: TR: 1,870 ms, TE: 30 ms, flip angle: 75°, voxel size: 3.0×3.0×2.0 mm, FOV: 192, number of slices: 58 axial slices parallel to the AP-PC plane. During scanning, each participant was asked to remain still and relaxed, with their eyes fixated on a cross, and without thinking of anything deliberate. Foam pads and earplugs were employed to reduce head motion and scanning noise. Structural T1-weighted MRI scans were acquired for co-registration purposes using a T1-weighted 3D magnetization-prepared rapid gradient-echo (MPRAGE) sequence in a sagittal plane with 1 mm isotropic resolution. Sequence parameters: TR: 2,000 ms, TE: 1.9 ms, flip angle: 9°, TI: 920 ms, FOV: 256×256, and 176 contiguous slices. The MRI protocol also included T2-Fluid-attenuated inversion recovery (FLAIR), and susceptibility-weighted imaging (SWI) sequences, using standard parameters for clinical brain evaluation.

BOLD Data Preprocessing

Functional connectivity analysis was carried out using the CONN-fMRI toolbox v22a as implemented using statistical parametric mapping software SPM12 (http://www.fil.ion.ucl.ac.uk/spm). Functional volumes pre-processing pipeline included realignment with correction of susceptibility distortion interactions, slice timing correction, outlier detection, direct segmentation, and MNI-space normalization, with a resolution voxel size of 2.0×2.0×2.0 mm, and spatial smoothing (8 mm FWHM Gaussian kernel) steps. The preprocessing steps derived (1) the realignment covariate, containing the six rigid-body parameters characterizing the estimated subject motion, (2) the scrubbing covariate containing potential outlier scans performed with CONNs artifact detection tool (ART), and (3) the quality assurance (QA) covariate based on global signal change (>3 standard deviations from the mean image intensity) and framewise displacement (FD) scan-to-scan head-motion. Age and sex were also used as group (second level) covariates. A component-based noise correction procedure (CompCor) approach was used to identify additional confounding temporal factors controlling for physiological noise, BOLD signal present in white matter, and head motion effects.

Finally, residual BOLD time series were then bandpass-filtered at a frequency range of 0.01-0.009 Hz. Individual connectivity maps were generated using the seed-to-voxel approach. We examined rsFC using a priori seeds derived from the extended HCP-MMP atlas (HCPex), a modified and extended version of the Human Connectome Project-MultiModal Parcellation atlas (HCP-MMP), which provides the surface-based of 360 human cortical areas. Bivariate correlation analysis was used to determine the linear association of the BOLD time series between the seed and significant voxel clusters. Fisher's Z transformation was applied to the correlation coefficients to satisfy normality assumptions. Then, functional connectivity maps were thresholded at P<0.05 false discovery rate (FDR) corrected for multiple comparisons. ROI-to-ROI network analysis was focused on depression-related commonly reported large-scale brain networks, which included: default mode (DMN), and salience (SN). Inter-network and intra-network connectivity values were calculated producing a symmetrical nodes connectivity matrix using MATLAB R2021b (MathWorks, Natick, MA). Finally, participants with head motions of >2 mm in any direction between volumes, rotations of >2° in any axis during scanning, or mean FD of >0.5 in either the pre- or post-treatment maps were excluded from the dataset.

Statistical Analysis—Descriptive Statistics

The demographics and clinical continuous data are expressed as means±standard deviations (SD). Two-tailed independent t-tests were performed to compare variables between groups when a normality assumption was held according to a Kolmogorov-Smirnov test. Categorical data were expressed in numbers and percentages. To evaluate the intervention's effect, the student's t-test was used to compare post-treatment and pre-treatment data. The effect size was evaluated using Cohen's d method. Data analysis was performed using MATLAB R2021b (MathWorks, Natick, MA) statistics and machine learning toolbox.

Imaging Analysis Statistic

At the group level, seed-to-voxel resting-state functional connectivity (rsFC) was analyzed using a repeated measure model to test the intervention's effect. The analysis was implemented in SPM software (version 12, UCL, London, UK) with a parametric analysis approach across the entire brain volume. RsFC was considered significant at joint-probability thresholds of 0.001 at the voxel level, and $p<0.05$ false discovery rate using the Benjamini-Hochberg FDR procedure corrected for multiple comparisons across the whole brain at the cluster level, with a minimum cluster size of 50 voxels. The REX toolbox was used to extract cluster connectivity statistical values. Spearman rank correlations were used to test for associations with cognitive and behavioral scores.

Results

Participants Demographic and Recruitment

Out of the twenty individuals assessed for eligibility, two were excluded due to claustrophobia, and one opted out by withdrawing consent. Consequently, the study proceeded with seventeen participants.

Decreased Self-Reported Depression

Figure 7:
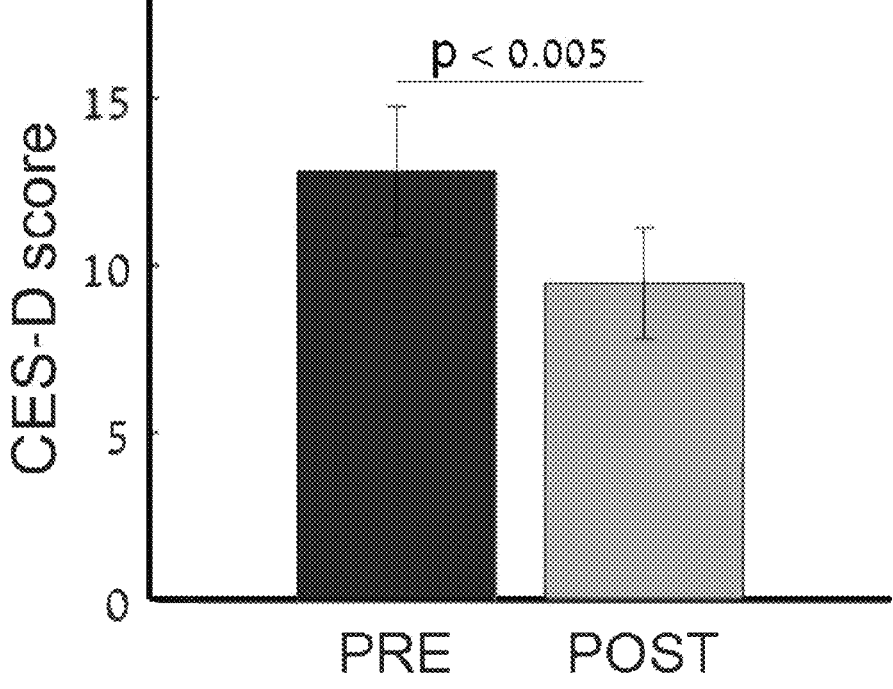
FIG. 7 shows CES-D score changes. The intervention significantly decreased self-reported depression CES-D questionnaire. Following the intervention, CES-D (depression scale) score was reduced by 26.6% with a large effect size (d=−0.829, p=0.004). Data are presented in mean±SEM, P-value, paired student's t-test analysis.

Questionnaire analysis is summarized in Table 1. Following the intervention, CES-D (depression scale) score was reduced by 26.6% with a large effect size (d=−0.829, p=0.004) (FIG. 7). A trend toward improvement in the anxiety score (GAD7) was shown (p=0.063, d=−0.484). No significant changes were observed in quality of life and well-being measures.

FIG. 7 shows CES-D score changes. The intervention significantly decreased self-reported depression CES-D questionnaire. Following the intervention, CES-D (depression scale) score was reduced by 26.6% with a large effect size (d=−0.829, p=0.004). Data are presented in mean±SEM, p-value, paired student's t-test analysis.

TABLE 1

| | | | | | Effect |
| Questionnaire analysis | | | | | |
| | PRE | POST | Change | p-value | size* |
|---|---|---|---|---|---|
| N | | | 17 | | |
| SF-36 | | | | | |
| Physical functioning | 83.5 ± 24.6 | 87.9 ± 21.3 | 4.4 ± 32.0 | 0.577 | 0.138 |
| Physical limitations | 79.4 ± 32.4 | 89.7 ± 17.3 | 10.3 ± 31.9 | 0.203 | 0.322 |
| Emotional limitations | 68.6 ± 42.0 | 80.4 ± 30.4 | 11.8 ± 42.4 | 0.269 | 0.278 |
| Energy | 62.1 ± 19.6 | 62.9 ± 22.1 | 0.9 ± 21.9 | 0.870 | 0.040 |
| Emotional wellbeing | 73.2 ± 14.2 | 70.4 ± 20.0 | -2.8 ± 20.9 | 0.586 | −0.135 |
| Social function | 86.8 ± 18.9 | 93.4 ± 16.7 | 6.6 ± 16.6 | 0.120 | 0.399 |
| Pain Domain | 83.2 ± 15.8 | 85.0 ± 14.6 | 1.8 ± 8.9 | 0.427 | 0.198 |
| General Health Domain | 76.8 ± 14.3 | 79.7 ± 19.1 | 2.9 ± 16.1 | 0.463 | 0.183 |

TABLE 1-continued

| | | | | | Effect |
| Questionnaire analysis | | | | | |
| | PRE | POST | Change | p-value | size* |
|---|---|---|---|---|---|
| MHC_SF | | | | | |
| Total | 45.9 ± 10.1 | 47.5 ± 10.2 | 1.5 ± 6.6 | 0.356 | 0.231 |
| Emotional well-being | 10.3 ± 2.7 | 10.8 ± 2.6 | 0.5 ± 2.2 | 0.326 | 0.246 |
| Social well-being | 12.8 ± 4.1 | 13.1 ± 4.6 | 0.3 ± 4.3 | 0.779 | 0.069 |
| Psychological well-being | 22.8 ± 4.9 | 23.5 ± 4.5 | 0.7 ± 2.9 | 0.332 | 0.243 |
| CES-D | 12.8 ± 7.7 | 9.5 ± 6.6 | −3.4 ± 4.0 | 0.004 | −0.829 |
| GAD7 | 4.7 ± 4.4 | 3.3 ± 3.1 | −1.4 ± 2.9 | 0.063 | −0.484 |

*Effect size, The paired Cohen's d effect size

SF-36, the 36-Item Short Form Survey, MHC-SF, Mental Health Continuum Short Form, CES-D, Center for Epidemiologic Studies Depression Scale, GAD-7, General Anxiety Disorder-7.

Improved DMN and SN Networks Interplay

The ROJ-to-ROJ network analysis disclosed a reduction in post-intervention intra-network connectivity within the DMN, with z-scores diminishing from 0.64±0.28 to 0.59±0.23, achieving statistical significance (p<0.002, FIG. 8B). Conversely, no significant changes were observed in the SN connectivity, where z-scores slightly changed from 0.62±0.27 to 0.60±0.27, not reaching statistical significance (p=0.169). Furthermore, the analysis did not reveal significant changes in the inter-network connectivity between the DMN and SN, with z-scores marginally adjusting from −0.165±0.22 to −0.160±0.21 (p=0.126), however, a significant correlation was found between changes in inter-network rsFC and changes in CES-D score (r 0.486, p<0.05) following treatment, demonstrating that improvement in depression score is correlated with increased internetwork anticorrelation.

FIGS. 8A-8C shows DMN-SN ROI-to-ROI network connectivity. The default mode network (DMN), and salience network (SN) are anticorrelated in the healthy non-depressed brain. Intra-network connections and internetwork connections are presented as lines. Decreased post-intervention intra-network connectivity (z-score: 0.64±0.28 to 0.59±0.23, p<0.002) within the DMN. The improved CES-D depression score (negative change mark improvement in the depression state for the post vs. pre assessment) was correlated with increased negative internetwork DMN-SN rsFC. This suggest correlation between the extent in which individuals subjects improved in the depression and the extent in which their connectivity pattern became healthier (i.e. reflect de-segregation between DMN and SN (as in depressed subjects this anticorrelation is lost).

Increased rsFC Between the MTL and Frontal Executive Areas Post Intervention.

Seed-to-voxel based analysis revealed a significantly increased post-training rsFC between left and right hippocampal and parahippocampal areas within the medial temporal lobe (MTL), and between the frontoparietal and the DMN networks (FIGS. 8A-8C).

Most significant increases in rsFC were demonstrated between the left hippocampus and the posterior cingulate cortex (PCC, BA31_R, k=328, $p_{FDR}<0.0001$), inferior parietal cortex, IPC (BA40, k=305, $p_{FDR}<0.0001$) and posterior parietal cortex (BA5, k=356, $p_{FDR}<0.0001$) (FIG. 4A). Significant increases in rsFC were also demonstrated between the left parahippocampal area and the dorsal pre-frontal cortex (PFC, BA9_L) rsFC (k=176, $p_{FDR}$0.027). and between the right parahippocampal and the anterior prefrontal cortex and dorsal anterior cingulate cortex (dACC) (BA10_R, BA32_L; k=98, $p_{FDR}$=0.010, k=158, $p_{FDR}$=0.005 respectively) (FIG. 4B). Importantly, this increase was correlated with maze-solving performance (r=0.508, p<0.05), demonstrating the dynamic learning process (FIG. 4C).

FIGS. 4A-4C shows seed connectivity maps of longitudinal differences. Seed: left hippocampus. Seed: right para-hippocampus. POST>PRE-intervention of the resting state brain imaging data—group level. n=17, p<0.05, FDR corrected, parametric stats, two sided. FIG. 4C shows a correlation between the changes in training score and increased PHA3-dACC post training connectivity. Parahippocampus, PHA, dorsal anterior cingulate cortex, dACC.

Increased rsFC of Areas Correlated with Ego-and-Allo-Centric Navigation

As the Retrosplenial cortex (RSC) integrates both ego-centric and allocentric spatial information streams, there was demonstrated increased connectivity in this key area following the treatment. RsFC between the right RSC seed and right parietal cortex was increased (k=211, $p_{FDR}$<0.002), potentially contributing to the egocentric navigation performance. Additionally, increased rsFC was demonstrated in the right anterior prefrontal cortex (BA10, k=175, $p_{FDR}$<0.004), potentially contributing to the allocentric navigation performance (FIG. 5). n=17, p<0.05, FDR corrected, parametric stats, two sided.

FIGS. 5A-5B shows seed-to-voxel connectivity maps of longitudinal differences. The retro splenial complex (RSC) integrates both egocentric and allocentric spatial information streams. Improved post-training rsFC was found in both egocentric and allocentric networks (k=211, $p_{FDR}$<0.002 and k=175, $p_{FDR}$<0.004 respectively) Seed: right RSC, n=17, POST>PRE-intervention, parametric stats, two sided. Bar graphs of cluster Fisher's Z effect size connectivity values, error bars, CI.

Increased rsFC Between Spatial Navigation Networks and the Insula

Seed-to-voxel based functional connectivity analysis revealed a significantly increased post-training rsFC between spatial navigation networks and the granular insular cortex seed (FIG. 6). Significant increases were demonstrated in the egocentric network key areas: precuneus (BA7, k=1172, $p_{FDR}$<0.0001), lingual gyrus (BA19, k=630, $p_{FDR}$<0.0001), and fusiform gyrus (BA37, k=111, $p_{FDR}$<0.02), and allocentric network key areas: medial prefrontal cortex, mPFC (BA32, k=101, $p_{FDR}$<0.01). These results may be linked to increased multisensory stimulus attention and self-awareness process. The results might also suggest the synergetic psychological and cognitive intervention increase the connectivity between areas that are dedicated to spatial and verbal memory (and are most tightly linked to age related degeneration) and limbic system structures such as the insula.

FIG. 6 shows seed-to-voxel connectivity maps of longitudinal differences. Increased post-training rsFC between spatial navigation networks and the insula. Seed: the left granular insular cortex. n=17, POST>PRE-intervention, parametric stats, two sided.

Discussion

In this proof-of-concept study, the impact of a dual-faceted intervention was assessed utilizing psychological strategies targeted at chronic stress and neuroplasticity-enhancing spatial memory training can impact related psychological outcomes and the brain areas associated with these functions. This intervention uniquely incorporated both allocentric and egocentric navigation techniques through digital HW mazes, employing an innovative protocol that transitions from visual to auditory cues, mimicking the effects of blindfolding.

Participants followed a two-week protocol of daily half-hour digital intervention and were evaluated before and after the training using psychological questionnaires and rsFC. Key results showed:
1. A positive impact on clinical depression scores (FIG. 7);
2. Improved (healthier/less depressed) DMN intra-network connectivity (FIG. 8B);
3. A correlation between the changes in depression scores and increased negative inter-network connectivity between the DMN and the SN (FIG. 8C);
4. An increase in connectivity between the MTL memory-related areas and executive working memory frontal areas, which was also correlated with the spatial memory HW maze-solving total performance index (FIG. 4C).

Finally, a significant increase in connectivity was found between the allocentric and egocentric navigation areas (FIG. 5). Taken together, these results suggest that a synergetic psycho-cognitive intervention, paired with a blindfolding protocol, significantly affects specific brain plasticity and behavioral changes. The results demonstrate that digital interventions can drive positive changes in both psycho-cognitive abilities and connectivity in areas of the brain that support spatial and verbal memory, most susceptible to aging and early AD.

This study employed functional neuroimaging to gauge the specific large-scale modulation of synaptic connectivity and neuroplasticity to identify changes in visuospatial performance and changes in psychological state by employing a battery of psychological questionnaires. The present study, conducted on participants aged 55-60 with self-reported SCD employed virtual unique versions of multisensory enriched environment protocol of the classical Hebb Williams mazes. This protocol aimed to induce rapid neuroplasticity and increase connectivity, such as that seen in sensory substitution studies and studies in the blind and sensory deprived.

Firstly, the findings provide an empirical proof-of-concept for the hypothesis that short exposure to virtual HB mazes, within a multisensory enriched environment, combined with a gradual blindfold protocol integrating both allocentric and egocentric cues, along with complementary stress reduction psychological interventions, effectively promotes neuroplasticity and enhances psychological well-being in a very specific and predictive way. This produces a synergistic effect, the integration of digital psychological and cognitive multisensory training provides a platform for enhancing brain plasticity across the lifespan. The approach can be used on individuals with neurodegenerative processes within the aging brain, since this combined strategy may exert a specifically target and modulate brain regions particularly vulnerable to aging, such as the MTL and the DMN, as well as their connectivity with other brain areas.

In conclusion, the present disclosure shows that the integration of a combined psycho-cognitive chronic stress reduction interventions with a gradual cross modal blind-folded navigation approach, which incorporates both ego-centric and allocentric strategies, produces a synergy that is impacts the aging brain, if maintained. These outcomes—both behavioral and connectivity patterns, offers support for combined intervention to mitigate inflammation and decelerate the progression of degenerative brain diseases. More-over, by pushing the boundaries of critical periods theory for brain plasticity in aging individuals, the study suggests that relatively short (weeks), daily digital interventions via a self-training protocol can elicit quite dramatic alterations in brain connectivity within regions crucial for spatial and verbal memory, areas often susceptible in the early stages of AD.

Example 3

Digital Interventions

Further examples (non-exhaustive) of additional digital interventions are provided i.e., interventions that directly affect the brain, improve spatial and verbal memory, cognition, etc.

Sound and vibration sequences: In a particular order, each one of your ears will receive a unique sound and each one of your wrists will vibrate in a different form. Your goal is to remember the longest signals sequence possible. This digital intervention is based on "Simon Memory Game" with a slight change: instead of using the auditory and visual perceptions, the participant will use the auditory and haptic perceptions. The sequence will begin with a single signal—which the participant will be asked to repeat. After a correct answer, the first signal will be followed by another one. The speech recognition system will enable the app to follow the participant's answers.

3D music: After listening to music, the participant is asked to point in the direction of each instrument with his hands. The participant will not only need to identify the direction of each instrument but also to remember the direction until the end of the song.

Examples (non-exhaustive) of digital interventions used i.e., interventions that modulate the immune system, are described herein.

Mindful breathing. The participant is guided to breathe deeply (diaphragmatic breathing) using sounds that accompany the breathing. Inclusion of feedback from measured respiration rate, heart rate, etc. is also possible. Mindful breathing involves paying focused attention to the sensations of the breath as it enters and leaves the body, without judgment or distraction. For example, one might sit comfortably, close their eyes, and consciously observe the rise and fall of their abdomen with each inhale and exhale, while gently returning attention to the breath whenever the mind wanders.

Medication-specific guided imagery. The participant will be guided to imagine the operation of the medication in their body. Various sensory cues are provided to the participant to help him anticipate the operation e.g., to help manage expectations, reduce anxiety. It can be implemented by vivid mental imagery to enhance the effectiveness of medication by visualizing it positively impacting the body's healing processes. For example, a patient prescribed antibiotics might close their eyes, imagine the medication as a powerful army, fighting and eliminating harmful bacteria, while feeling a sense of relief and restoration in the affected areas. This can also be coupled to a specific digital intervention relating a similar emotion to the participant.

Body scanning. The participant is guided to conduct systematic body scanning (perhaps focused more on parts of the body that hurt in particular). The training may be accompanied by any sensory cue such as sounds coming from the body part that we are asking to focus on or by AR/VR visuals directing to that specific body part. For example, a person practicing body scanning might start at their feet, gradually moving upward, paying close attention to sensations such as warmth, tingling, or tension, and gently releasing any areas of tightness or discomfort as they become aware of them. Digital platforms can be implemented to perform body scanning.

Progressive muscle relaxation. Similar to body scanning, but with progressive muscle relaxation. The focus may range from small muscle groups to larger body parts. A participant might start by tensing the muscles in their feet for a few seconds, then releasing the tension while focusing on the sensation of relaxation spreading through your feet and toes.

5-4-3-2-1 exercise. The participant is instructed to focus on five things that can be seen, four things you can be heard, three things that can be felt, two things that can be smelled and one thing that can be tasted.

Attention training technique. This generally involves exercises designed to enhance focus and concentration by directing attention to specific stimuli or tasks while minimizing distractions. For example, the participant is presented with distinct soundscapes (e.g.—a waterfall, or an owl) that move around in space. The participant will be instructed to focus their attention on a specific soundscape and follow it for some time (e.g., 90 seconds), after which the participant may be instructed to focus on a different soundscape.

Value training. Based on value checklist training performed before, a reminder of this value, and then focusing on that value and what you would like to do to get you closer to it. Employing this specific digital intervention via VR could potentially utilize a visual experience of the value (e.g.—family, friends, etc.). Value Checklist Training: Select values that are important to you (those that you choose "get closer" with the sounds). Then select one. Then think about an area in your life in which you would like to express this value more.

Psychoeducation. Various psychoeducation modules on the chronic condition and the symptoms associated with it, including physiological explanations about the neurodegenerative disease, drug therapy (e.g., immunotherapy), the role of thoughts and other top-down processes in creating symptoms, and the ways mental interventions can help. In addition, modules on the way the digital interventions and their combination with the medication operates. For some modules, VR visualizations may be used as well.

Maladaptive thought patterns identification exercise. An exercise in which the patient needs to identify maladaptive thought patterns.

Example 4

Effect on Immune System Biomarkers

The present disclosure shows the effect of digital therapy interventions on immune system biomarkers.

Figure 12A:
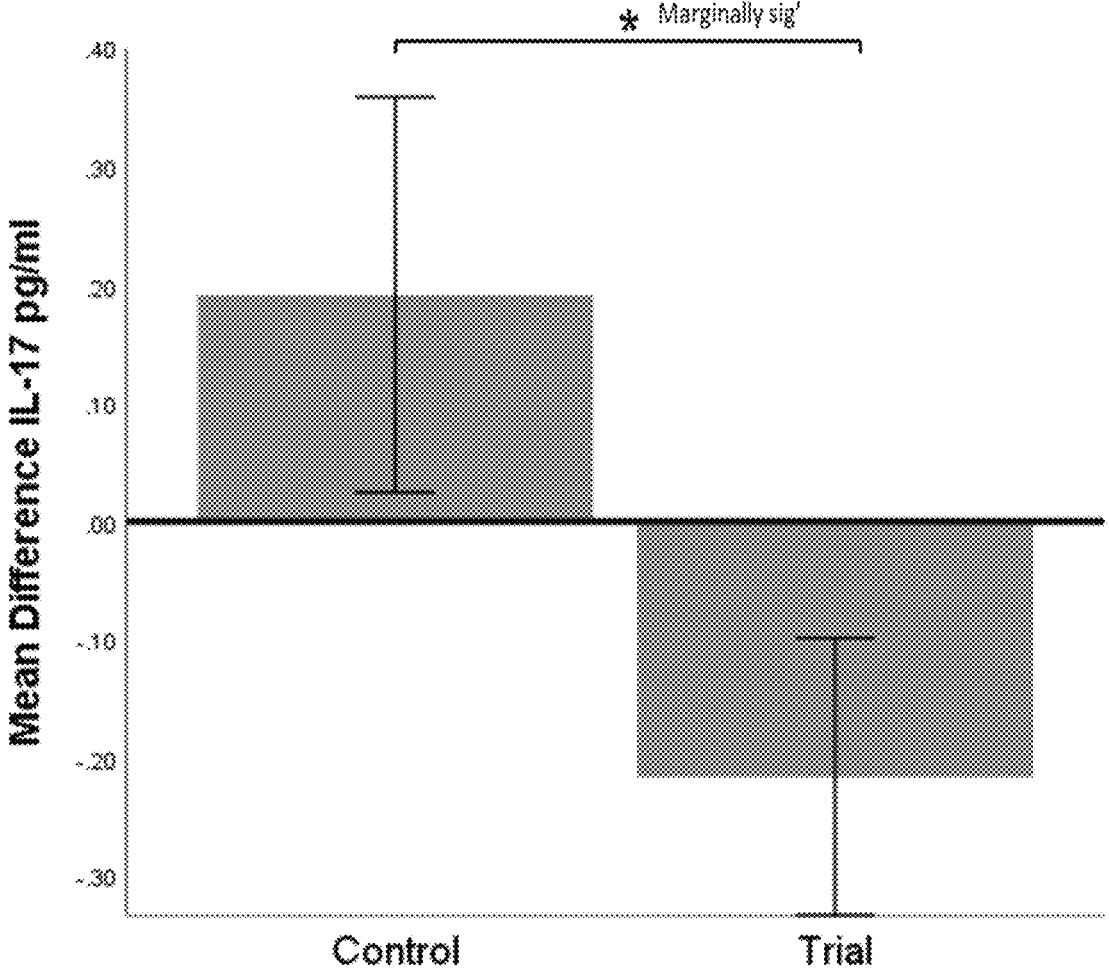
FIGS. 12A-12B shows the effect of digital interventions on immune system biomarkers.

FIG. 12A shows the effect of digital interventions on IL-17. IL-17 has been linked to depression and may be a biomarker for reduced response to antidepressants and clinical trials are currently underway examining the efficacy and safety of monoclonal antibodies to IL-17 and in treatment resistant depression (e.g., chronic stress, neuroinflammation, and depression: an overview of pathophysiological mechanisms and emerging anti-inflammatories), as shown in FIG. 12A. IL-17 can upregulate PD-1 expression, decreasing response and mediating resistance to PD-1 blockade. IL-17 inhibitor and PD-1 blockade jointly establish anti-tumor.

Figure 12B:
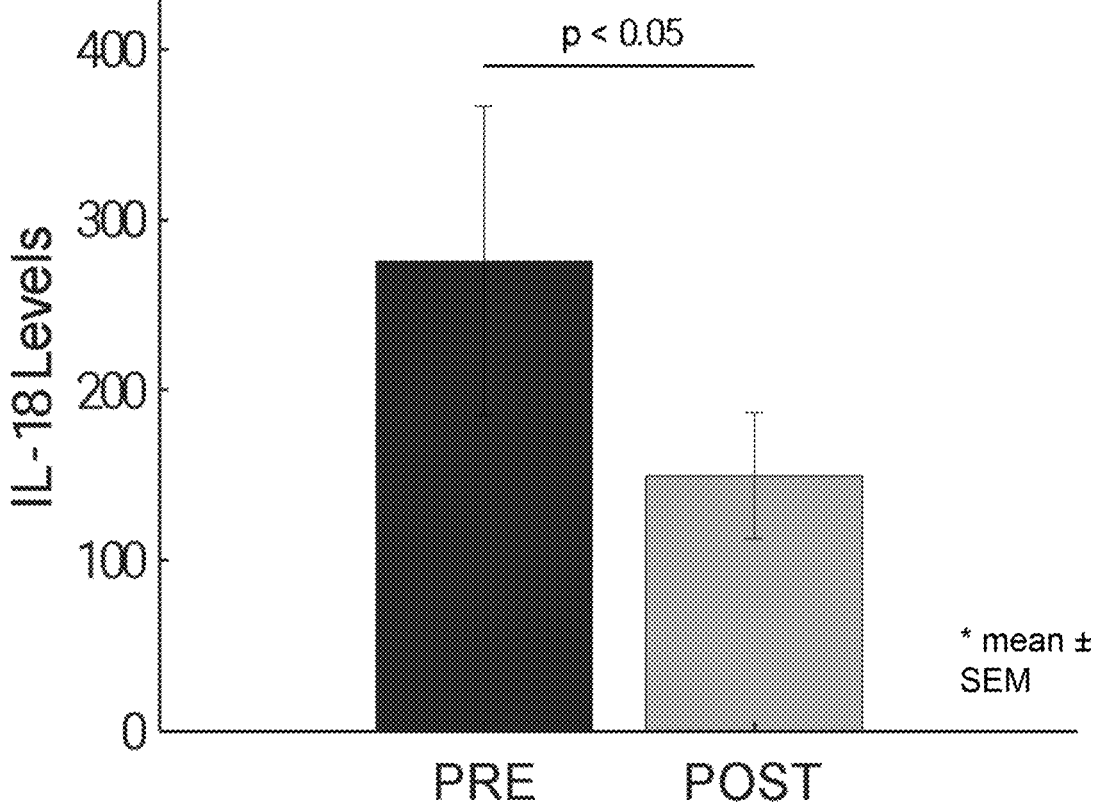
Figure 13A:
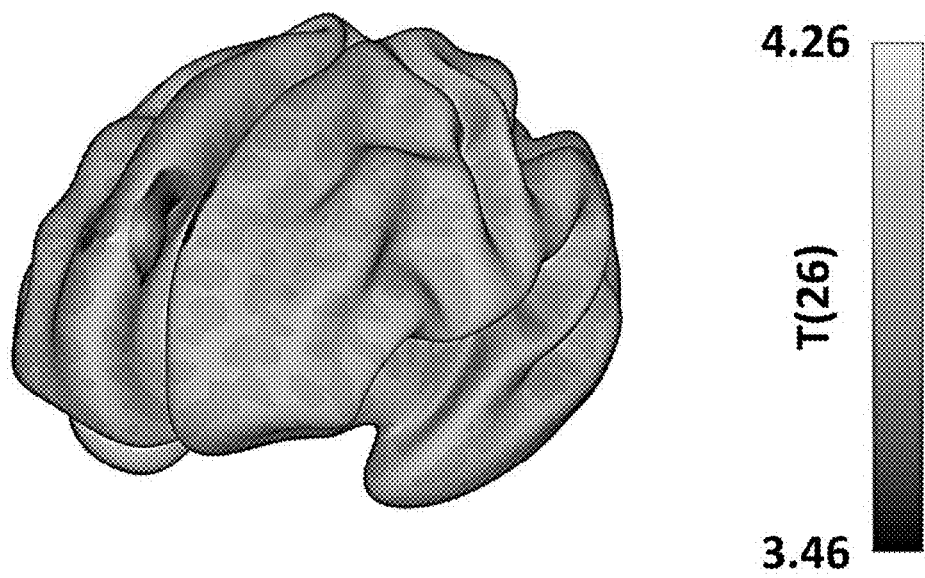
FIGS. 13A-13F shows significant functional connectivity changes, in correlation with psychological improvement.
Figure 13B:
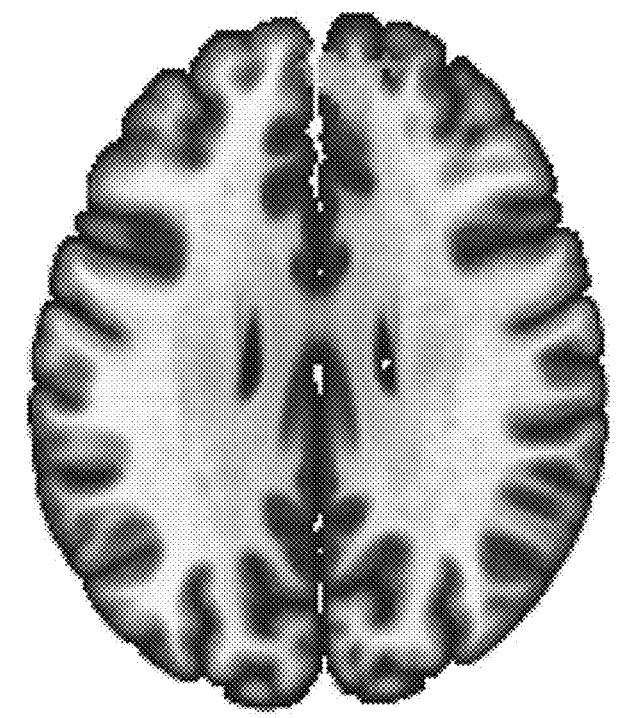
Figures 13C, 13D:
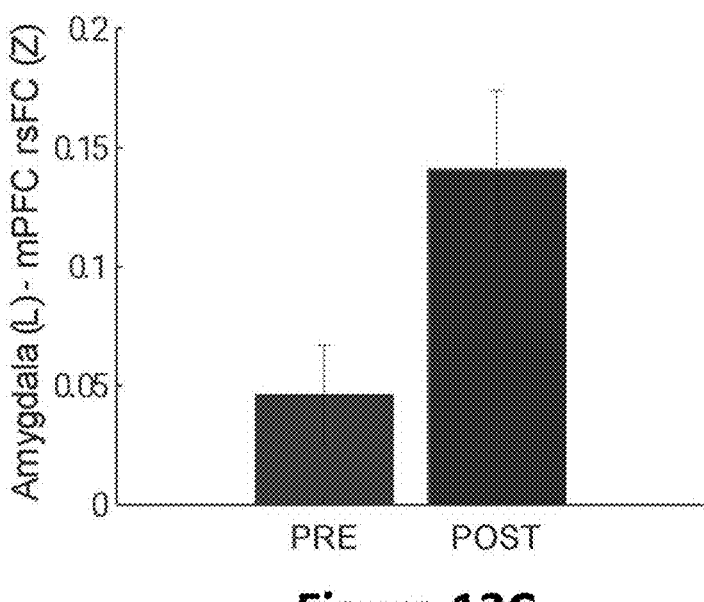
Figure 13E:
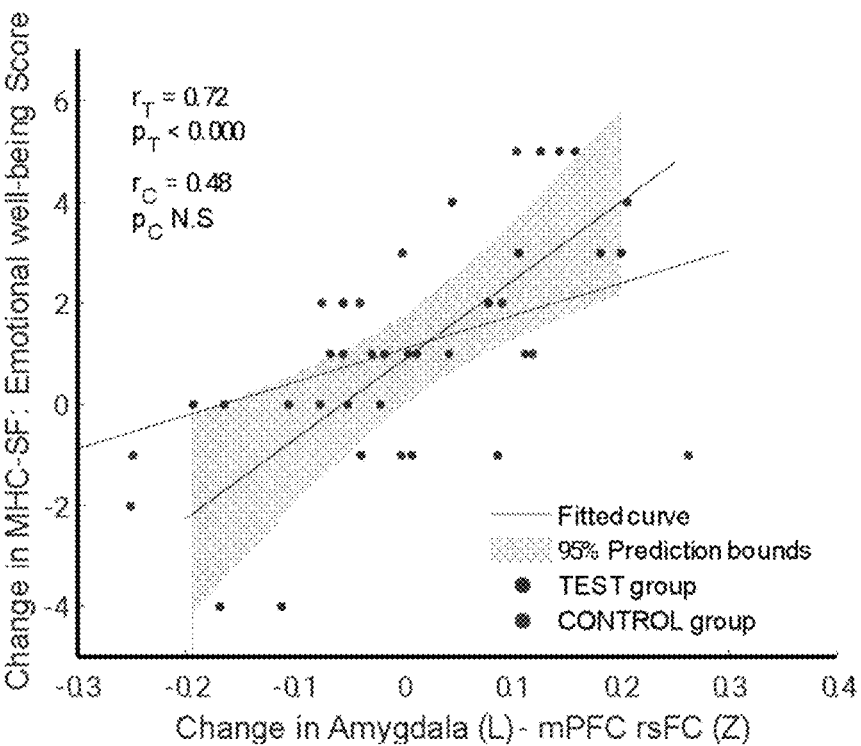
Figure 13F:
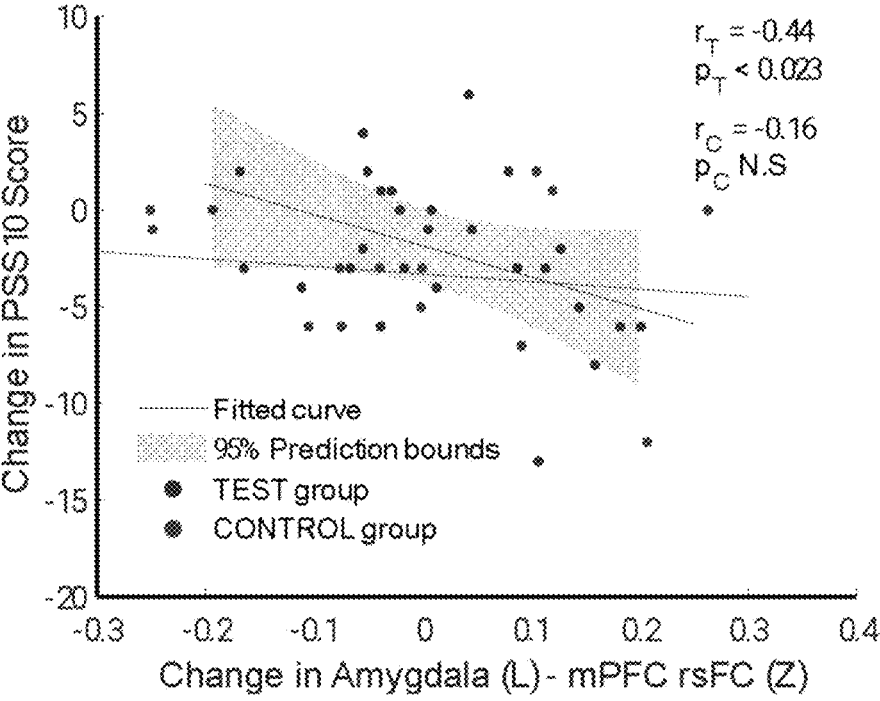
Figure 14D:
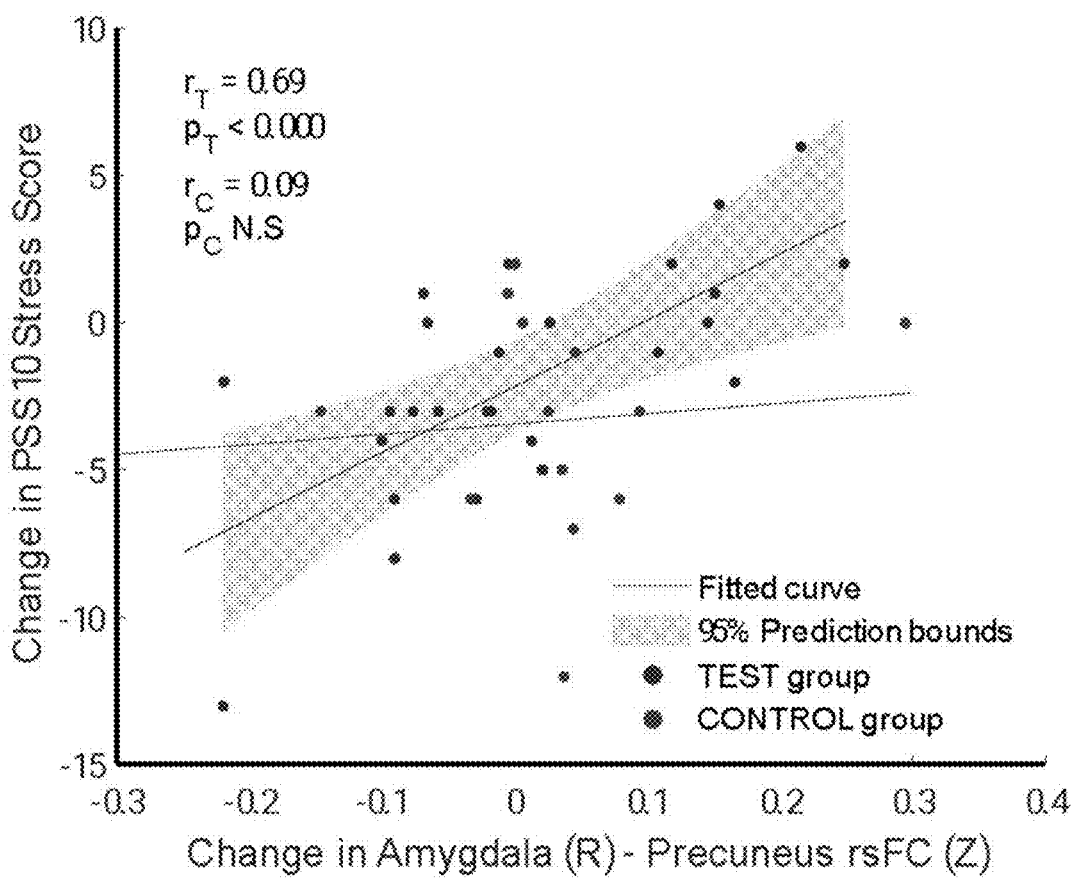
Figure 15A:
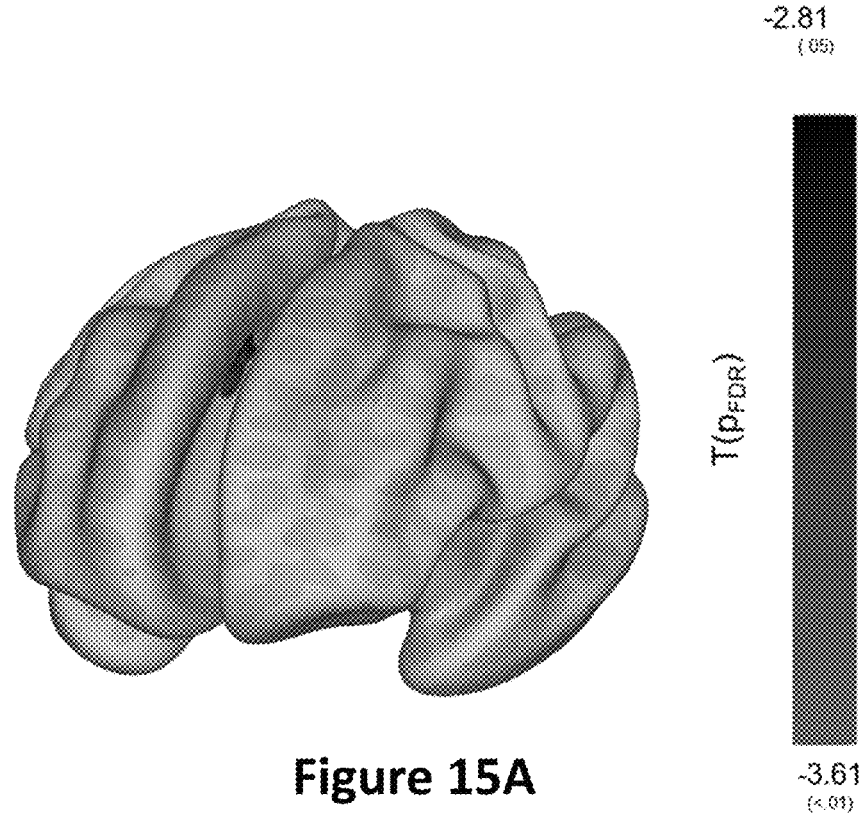
FIGS. 15A-15D shows correlation of functional connectivity changes with reduction in IL-18 level with digital therapy interventions.
Figure 15B:
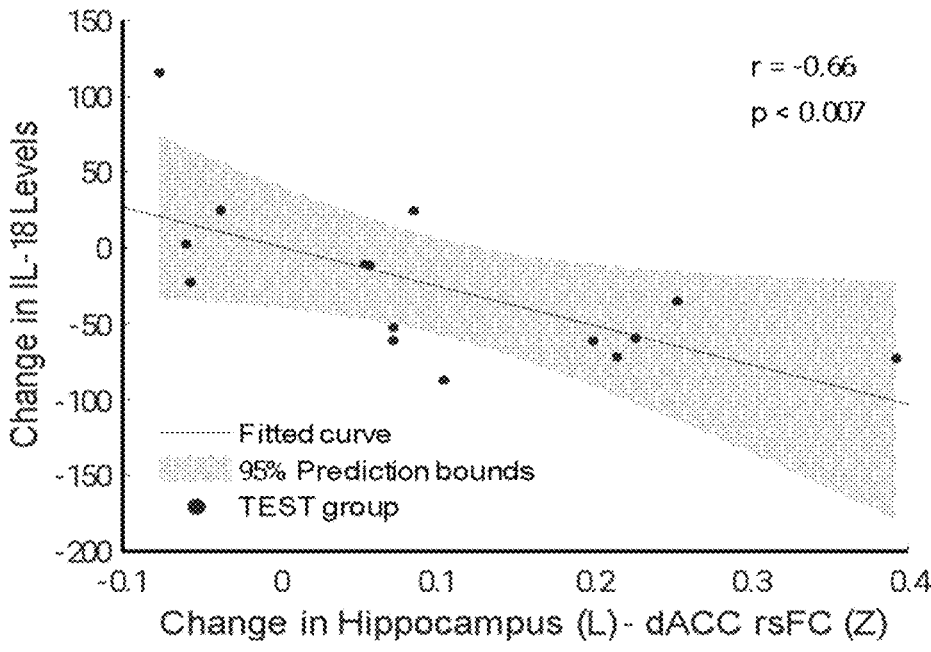
Figure 15C:
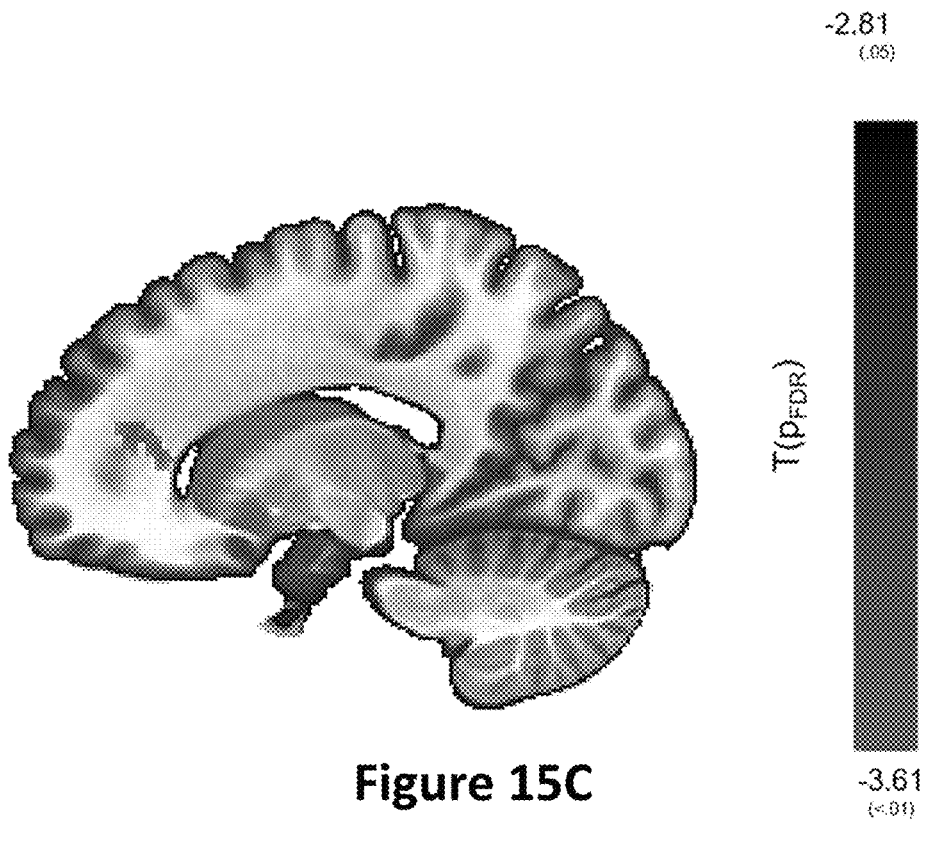
Figure 15D:
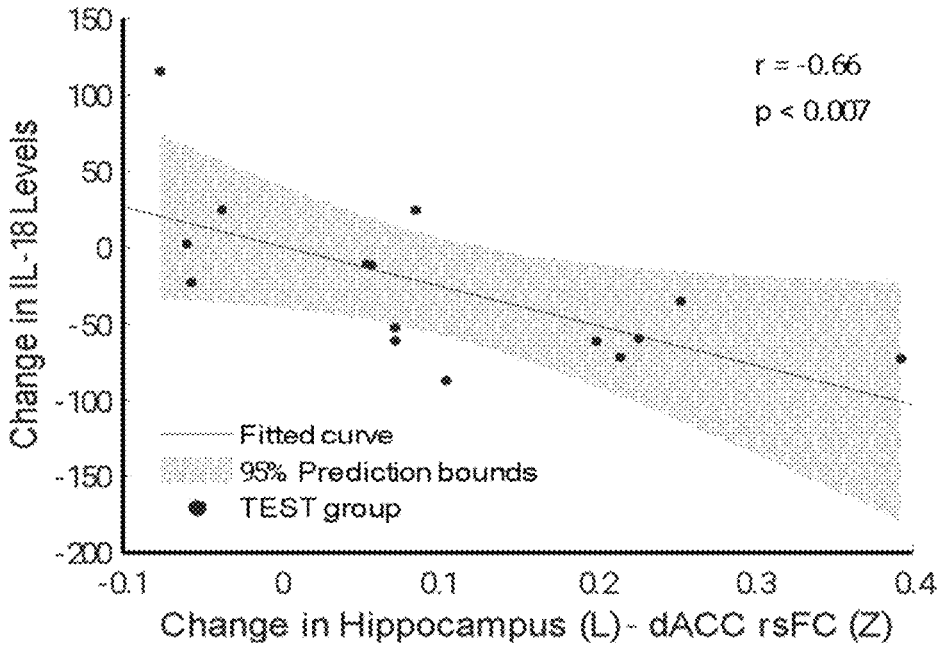
Figure 16B:
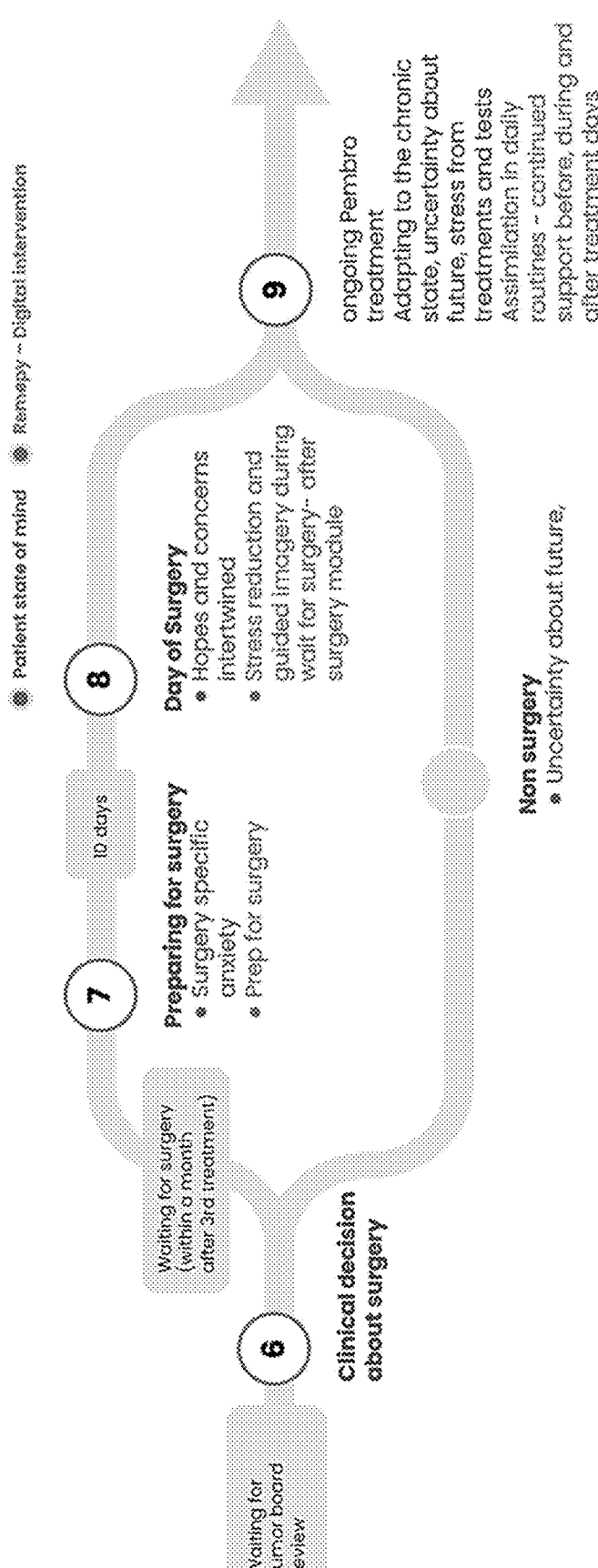

IL-18 has been linked to inflammation and depression, it stimulates the production of IFN-7 and pro-inflammatory cytokines and affects neural networks that modulate motivation and reward processing in depression. FIG. 12B shows the reduction of levels of IL-18 following the digital therapy interventions of the present invention. Interleukin-18, is a pro-inflammatory cytokine, which induces IFN-7. Higher levels of IL-18 are associated with heart failure, ischemic heart disease, and type 1 diabetes in patients, and in the AD brain. Robust evidence shows that IL-18 is a mediator of inflammation and associated with the aging process.

In one embodiment, the term "a" or "one" or "an" refers to at least one. In one embodiment the phrase "two or more" may be of any denomination, which will suit a particular purpose. In one embodiment, "about" or "approximately" may comprise a deviance from the indicated term of +1%, or in some embodiments, −1%, or in some embodiments, ±2.5%, or in some embodiments, ±5%, or in some embodiments, ±7.5%, or in some embodiments, ±10%, or in some embodiments, ±15%, or in some embodiments, ±20%, or in some embodiments, ±25%.

Those skilled in the art to which this invention pertains will readily appreciate that numerous changes, variations, and modifications can be made without departing from the scope of the presently disclosed subject matter, mutatis mutandis.

What is claimed is:

1. A computer-implemented method for digital therapy for an individual carried out on a personal electronic device, said method comprising:

receiving data related to the individual;

generating a digital therapy intervention plan based on the data wherein the digital therapy intervention plan comprises at least one digital maze as part of a sequence of digital mazes, to the individual;

providing sensory modality inputs to the individual selected from visual, auditory, tactile, or a combination thereof, for navigation in each digital maze;

detecting interactions by the individual thereby updating the position of the individual within the digital maze;

detecting maze navigation parameters based on the interactions by the individual and generating a performance score;

implementing the same digital maze to the individual until a predetermined condition is detected;

wherein the implementation of each digital maze further comprises modifying at least one sensory modality input on the personal electronic device during implementation of each digital maze, presenting it to the individual and monitoring the responses of the individual, thereby implementing sensory inhibition, sensory substitution, sensory integration, or a combination thereof;

wherein the sensory inhibition comprises at least partial reduction of at least one sensory modality input, wherein the at least one sensory modality input is selected from: visual, auditory, and tactile;

wherein the sensory substitution comprises at least partial replacement of at least one sensory modality input with at least one other sensory modality input selected from:

visual to auditory and/or tactile;

auditory to visual and/or tactile; and tactile to visual and/or auditory;

wherein the sensory integration comprises at least partial combination of at least two sensory modality inputs, wherein said at least two sensory modalities inputs are selected from: visual, auditory, and tactile.

2. The method of claim 1 wherein said generating a digital therapy intervention plan for the at least one digital maze comprises incorporating at least one obstacle selected from:

outer wall, inner wall, dead end, object, turn, interconnected paths, or a combination thereof.

3. The method of claim 2 wherein said sensory modality inputs are provided to assist said individual in completing said at least one digital maze in the shortest time, shortest path, with fewest obstacle impacts, or a combination thereof.

4. The method of claim 1 wherein the performance score is determined by evaluating the following maze navigation parameters: the time taken to complete the digital maze, path taken to complete the digital maze, the number of obstacle impacts, or a combination thereof.

5. The method of claim 1 wherein the predetermined condition is a threshold performance score for said digital maze, above which the individual is no longer presented with the digital maze to complete.

6. The method of claim 1 wherein an increase in sensory substitution is exhibited for each digital maze in the sequence of digital mazes, following the completion of each digital maze and/or said predetermined condition is detected; and wherein said sensory substitution comprises the at least partial substitution of at least one of said sensory modality inputs with at least one other of said sensory modality inputs.

7. The method of claim 6 further comprising the complete substitution of one of said sensory modality inputs with at least one other of said sensory modality inputs selected from:

visual to auditory and/or tactile;

auditory to visual and/or tactile;

tactile to visual and/or auditory.

8. The method of claim 1 wherein the interactions by the individual are selected from: touch gesture, motion gesture, voice commands, text input, camera and media interaction, sensor-based interactions, or a combination thereof.

9. The method of claim 4 further comprising generating and displaying a digital maze of increasing difficulty in the sequence of digital mazes, following the detection of said predetermined condition, for each digital maze.

10. The method of claim 9 further comprising generating and displaying a digital maze of increasing difficulty in the sequence of digital mazes wherein an increase in sensory substitution is exhibited;

wherein said sensory substitution comprises the at least partial substitution of at least one of said sensory modality inputs with at least one other of said sensory modality inputs.

11. The method of claim 10 further comprising the complete substitution of one of said sensory modality inputs with at least one other of said sensory modality inputs selected from:

visual to auditory and/or tactile;

auditory to visual and/or tactile;

tactile to visual and/or auditory.

12. The method of claim 9 wherein said increasing difficulty is achieved by: randomly generating a digital maze of a different structure, increasing the path length, increasing the number of turns, increasing the number of obstacles, diversifying the types of obstacles, decreasing the path width, incorporating a time challenge, increasing the performance threshold, changing the sensory modality inputs, adding interactive elements, incorporating distractions, incorporating tasks, incorporating moving obstacles, or a combination thereof.

13. The method of claim 2 wherein said generating and displaying the digital maze comprises creating between 1 and 1,000,000,000 obstacles, wherein said obstacles are configured to be stationary, moving, or a combination thereof.

14. The method of claim 1 further comprising providing feedback to said individual before, during, after, or a combination thereof, navigation in said digital maze, the feedback being determined by the user interactions and maze navigation parameters.

15. The method of claim 1 wherein said personal electronic device is selected from: smartphones, tablets, wearable device, smart TVs, computers, laptops, E-readers, gaming consoles, smartwatches, fitness trackers, portable media players, digital cameras, virtual reality (VR) headsets, augmented reality (AR) device, portable GPS devices, portable Bluetooth devices, portable digital assistant, smart glasses and, audio device or any combinations thereof.

16. A digital therapy system for digital therapy for an individual, the system comprising:

a graphical user interface (GUI) configured to provide visual sensory modality input to the individual;

speakers configured to provide auditory sensory modality input to the individual;

a haptic feedback system configured to provide tactile sensory modality input to the individual;

at least one processor configured to implement a software application for the digital therapy;

wherein the at least one processor is further configured to generate and display a digital maze on a personal electronic device to the individual;

wherein the at least one processor is further configured to implement: sensory inhibition, sensory substitution, sensory integration, or a combination thereof, for the digital maze;

wherein the at least one processor is further configured to:

generate and display at least one digital maze to an individual;

provide sensory modality inputs to the individual selected from visual, auditory, tactile, or a combination thereof, for navigation in the digital maze;

detect user interactions of the individual and generating a performance score;

display the same digital maze to the individual until a threshold performance score is detected;

generate and display an adapted digital maze to the individual after a threshold performance score is detected for each digital maze, wherein the sensory modality inputs for each subsequent adapted digital maze is changed, thereby implementing sensory inhibition, sensory substitution, sensory integration, or a combination thereof.

* * * * *